(12) United States Patent
Fan et al.

(10) Patent No.: US 8,673,558 B2
(45) Date of Patent: Mar. 18, 2014

(54) LUCIFERASE BIOSENSOR

(75) Inventors: Frank Fan, Madison, WI (US); Martin Ken Lewis, Madison, WI (US); John W. Shultz, Verona, WI (US); Keith V. Wood, Mt. Horeb, WI (US); Braeden Butler, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 13/454,464

(22) Filed: Apr. 24, 2012

(65) Prior Publication Data

US 2012/0214677 A1    Aug. 23, 2012

Related U.S. Application Data

(62) Division of application No. 10/957,433, filed on Oct. 1, 2004, now Pat. No. 8,183,036.

(60) Provisional application No. 60/510,187, filed on Oct. 10, 2003.

(51) Int. Cl.
    *C12Q 1/66*       (2006.01)
(52) U.S. Cl.
    USPC .................. 435/6.1; 435/7.8; 435/8; 435/189
(58) Field of Classification Search
    None
    See application file for complete search history.

(56) References Cited

U.S. PATENT DOCUMENTS

| | | | |
|---|---|---|---|
| 5,097,026 A | 3/1992 | Jahnsen | |
| 6,251,667 B1 | 6/2001 | Habener et al. | |
| 6,270,964 B1 | 8/2001 | Michnick et al. | |
| 6,294,330 B1 | 9/2001 | Michnick et al. | |
| 6,406,856 B1 | 6/2002 | Glover et al. | |
| 6,428,951 B1 | 8/2002 | Michnick et al. | |
| 6,573,059 B1 | 6/2003 | Reymond | |
| 6,602,677 B1 | 8/2003 | Wood et al. | |
| 6,762,026 B1 | 7/2004 | Sugiyama | |
| 6,808,874 B2 | 10/2004 | Griffiths | |
| 6,890,745 B1 | 5/2005 | Leng | |
| 7,083,911 B2 | 8/2006 | Wood et al. | |
| 7,241,584 B2 | 7/2007 | Wood et al. | |
| 7,452,663 B2 | 11/2008 | Wood et al. | |
| 7,700,310 B2 | 4/2010 | Somberg et al. | |
| 7,732,128 B2 | 6/2010 | Wood et al. | |
| 7,741,067 B2 | 6/2010 | Hawkins et al. | |
| 8,030,017 B2 | 10/2011 | Wood et al. | |
| 8,183,036 B2 | 5/2012 | Fan et al. | |
| 8,227,572 B2 | 7/2012 | Leitch et al. | |
| 2002/0022220 A1 | 2/2002 | Izevbigie | |
| 2002/0150885 A1 | 10/2002 | Weber et al. | |
| 2002/0151014 A1 | 10/2002 | Campbell | |
| 2003/0003506 A1 | 1/2003 | Umezawa et al. | |
| 2003/0068801 A1 | 4/2003 | Wood et al. | |
| 2003/0104507 A1 | 6/2003 | Wood et al. | |
| 2003/0170850 A1 | 9/2003 | Cardone et al. | |
| 2003/0203407 A1 | 10/2003 | Craig et al. | |
| 2003/0232404 A1 | 12/2003 | Wood et al. | |
| 2004/0101922 A1 | 5/2004 | Somberg et al. | |
| 2004/0157272 A1 | 8/2004 | Cardone et al. | |
| 2005/0026171 A1 | 2/2005 | Hawkins et al. | |
| 2005/0054573 A1 | 3/2005 | Werner et al. | |
| 2005/0170442 A1 | 8/2005 | Kupcho et al. | |
| 2005/0176071 A1 | 8/2005 | Nikiforov et al. | |
| 2005/0181452 A1 | 8/2005 | Westwick et al. | |
| 2006/0048592 A1 | 3/2006 | Wood et al. | |
| 2006/0183212 A1 | 8/2006 | Wood et al. | |
| 2008/0206798 A1 | 8/2008 | Wood et al. | |
| 2009/0137019 A1 | 5/2009 | Wood et al. | |
| 2009/0253131 A1 | 10/2009 | Wigdal et al. | |
| 2009/0286299 A1 | 11/2009 | Ronaghi et al. | |
| 2009/0305280 A1 | 12/2009 | Binkowski et al. | |
| 2009/0311769 A1 | 12/2009 | Wood et al. | |
| 2010/0021949 A1 | 1/2010 | Somberg et al. | |
| 2011/0039257 A1 | 2/2011 | Binkowski et al. | |
| 2011/0283373 A1 | 11/2011 | Binkowski et al. | |
| 2012/0009647 A1 | 1/2012 | Wood et al. | |
| 2012/0214677 A1 | 8/2012 | Fan et al. | |

FOREIGN PATENT DOCUMENTS

| | | |
|---|---|---|
| EP | 1 097 992 A2 * | 5/2001 |
| EP | 1229330 | 8/2002 |
| JP | 5501862 | 4/1993 |
| JP | 2002315589 | 10/2002 |
| JP | 2012/090635 | 5/2012 |
| WO | WO 95/18853 | 7/1995 |
| WO | WO 00/14267 | 3/2000 |
| WO | WO 00/24768 | 5/2000 |
| WO | WO 00/75332 | 12/2000 |
| WO | WO 01/20002 | 3/2001 |
| WO | WO 02/06458 | 1/2002 |
| WO | WO 02/08766 | 1/2002 |
| WO | WO 02/16944 | 2/2002 |
| WO | WO 02/059262 | 8/2002 |
| WO | WO 03/066883 | 8/2003 |
| WO | WO 2004/027094 | 4/2004 |
| WO | WO 2004/038039 | 5/2004 |
| WO | WO 2004/043992 | 5/2004 |
| WO | WO 2004/059294 | 7/2004 |
| WO | WO 2004/081189 | 9/2004 |
| WO | WO 2005/015161 | 2/2005 |
| WO | WO 2005/038029 | 4/2005 |

(Continued)

OTHER PUBLICATIONS

Goodsell, "PDB Molecule of the Month: Estrogen Receptor," http://www.rcsb.org/pdb/molecules/pdb45_1.html, (observed Dec. 8, 2003) 2 pages.

(Continued)

*Primary Examiner* — Jim Ketter

(74) *Attorney, Agent, or Firm* — Michael Best & Friedrich LLP

(57) ABSTRACT

A modified beetle luciferase protein which is an environmentally sensitive reporter protein is provided.

17 Claims, 35 Drawing Sheets

(56) References Cited

FOREIGN PATENT DOCUMENTS

| WO | WO 2005/052186 | 6/2005 |
|---|---|---|
| WO | WO 2006/023972 | 3/2006 |
| WO | WO 2007/120522 | 10/2007 |
| WO | WO 2009/142735 | 11/2009 |
| WO | WO 2011/143339 | 11/2011 |
| WO | WO 2013/071237 | 5/2013 |

OTHER PUBLICATIONS

Baird, G.S. et al., "Circular permutation and receptor insertion within green fuorescent proteins," Proc. Natl. Acad. Sci. USA (1999) 96:11241-11246.

Berman, H.M.et al., "The cAMP binding domain: an ancient signaling module," Proc. Natl. Acad. Sci. USA (2000) 102(1):45-50.

Binkowski et al., Engineered luciferases for molecular sensing in living cells, Current Opinion in Biotechnology, vol. 20, Iss. 1, Feb. 2009, pp. 14-18.

Bos, J.L., "Epac: a new cAMP target and new avenues in cAMP research," Nat. Rev. Mol. Cell. Biol. (2003) 4:733-738.

Burbelo, P.D. et al., "Detecting protein-protein interactions using renilla luciferase fusion proteins," Biotech. (2002) 33(5):1044-1049.

Chong, S. et al., "Single-column purification of free recombinant proteins using a self-cleavable affinity tag derived from a protein splicing element," Gene (1997) 192:271-281.

Daugherty et al., "Quantitative analysis of the effect of the mutation frequency on the affinity maturation of single chain Fv antibodies," PNAS USA 97(5):2029-2034 (2000).

Dremier, S. et al., "Search for new cyclic AMP-binding proteins," FEBS Lett. (2003) 546:103-107.

Fan, F. et al., "Novel genetically encoded biosensors using firefly luciferase," ACS Chemical Biology (2008) 3(6):346-351.

Genbank Accession No. AF115480, Sequence ID No. 123, "*Mus musculus* cAMP-dependent Rap1 guanine-nucleotide exchange factor mRNA, complete cds" (1999) 2 pages.

Genbank Accession No. AF192755, Seq. ID No. 125, "Trypanosoma brucei cyclic nucleotide phophodiesterase (PDE) gene, complete cds" (2002) 2 pages.

Genbank Accession No. M124921, "Rat type II cAMP-dependent protein kinase regulatory subunit mRNA, 3' end" (2002) 2 pages.

Genbank Accession No. NM_002734, "*Homo sapiens* protein kinase, cAMP-dependent, regulatory, type I, alpha (tissue specific extinguisher1), (PRKAR1A), transcript variant 1, mRNA," (2010) 5 pages.

Graf, R. et al., "Random circular permutation of genes and expressed polypeptide chains: application of the method to the catalytic chains of aspartate transcarbamoylase," Proc. Natl. Acad. Sci. USA (1996) 93:11591-11596.

Greer, L.F. et al., "Imaging of light emission from the expression of luciferases in living cells and organisms: a review," Luminescence (2002) 17(1):43-74.

Hanks, S.K. et al., "The eukaryotic protein kinase super family: kinase (catalytic) domain structure and classification," FASEB J. (1995) 9:576-596.

Heinemann, U. et al., "Circular permutation of polypeptide chains: implications for protein folding and stability," Prog. Biophys. Mol. Biol. (1995) 64(2-3):121-143.

Kaihara, A. et al., "Locating a protein-protein interaction in living cells via split renilla luciferase complementation," Anal. Chem. (2003) 75(16):4176-4181.

Kim et al., Circularly permutated bioluminescent probes for illuminating ligand-activated protein dynamics, Bioconjugate Chem, 2008, 19, pp. 2480-2486.

Kunkel, "Rapid and efficient site-specific mutagenesis without phenotypic selection," PNAS USA 82(2):488-492 (1985).

Laxman, B. et al., "Noninvasive real-time imaging of apoptosis," Proc. Natl. Acad. Sci. USA (2002) 99(26):16551-16555.

Leclerc, G.M. et al., "Development of a destabilized firefly luciferase enzyme for measurement of gene expression," BioTech. (2000) 29(3):590-601.

Lee, J-C., "Development of a cell-based assay for monitoring specific hepatitis C virus NS3/4A protease activity in mammalian cells," Anal. Biochem. (2003) 316(2):162-170.

Li, I.T. et al., "Protein biosensors based on the principle of fluorescene resonance energy transfer for monitoring cellular dynamics," Biotech. Lett. (2006) 28(24):1971-1982.

Littlewood, T.D. et al., "A modified oestrogen receptor ligand-binding domain as an improved switch for the regulation of heterologous proteins," Nucl. Acids Res. (1995) 23(10):1686-1690.

Lorenz, W. et al., "Isolation and expression of a cDNA encoding renilla reniformis luciferase," Proc. Natl. Academ. Sci. USA, May 1991, vol. 88, pp. 4438-4442.

Luker, K.E. et al., "Kinetics of regulated protein-protein interactions revealed with firefly luciferase complementation imaging in cells and living animals," Proc. Natl. Acad. Sci. USA (2004) 101(33):12288-12293.

Lykens et al., "Perforin is a critical physiologic regulator of T-cell activation," Blood, 118:618-626 (2011).

Maldonado, F. et al., "A cDNA clone encoding human cAMP-dependent protein kinase catalytic subunit calpha," Nucl. Acids Res. (1988) 16(16):8189-8190.

Massoud, T.F. et al., "Molecular imaging of homodimeric protein-protein interactions in living subjects," The FASEB Journal (2004) 18:1105-1107.

Mayer, B.J. et al., "Signalling through SH2 and SH3 domains," Trends Cell Biol. (1993) 3:8-13.

Michel, P. et al., "Expression and purification of polyhistidine-tagged firefly luciferase in insect cells—a potential alternative for process scale-up," J. Biotech., Short Technical Reports (2001) 85(1):49-56.

Murray et al., "Codon usage in plant genes" NAR 17: 477-498 (1989).

Nagai, T. et al., "Development of a GFP variant with fast and efficient maturation properties," (2002) 42(6):305-308.

Nagai, T. et al., Circularly permuted green fluorescent proteins engineered to sense Ca2+, Proc. Natl. Acad. Sci. USA, 2001, 98, pp. 3197-3202.

Nikolaev, V.O. et al., "Novel single chain cAMP sensors for receptor-induced signal propagation," J. Biol. Chem. (2004) 279(36):37215-37218.

Niles, A.L. et al., "Caspase activity assays," Meth. Mol. Biol. (2008) 414:137-150.

Øyen, O. et al., "Human testis cDNA for the regulatory subunit R1 1α of cAMP-dependent protein kinase encodes an alternative amino-terminal region," FEBS Lett. (1989) 246(1-2):57-64.

Ozawa, T. et al., "Split luciferase as an optical probe for detecting protein-protein interactions in mammalian cells based on protein splicing," Anal. Chem. (2001) 73(11):2516-2521.

Paulmurugan, R. et al., "An intramolecular folding sensor for imaging estrogen receptor-ligand interactions," Proc. Natl. Acad. Sci. USA (2006) 103(43):15883-15888.

Paulmurugan, R. et al., "Molecular imaging of drug-modulated protein-protein interactions in living subjects," Cancer Res. (2004) 64:2113-2119.

Paulmurugan, R. et al., "Monitoring protein-protein interactions using split synthetic renilla luciferase protein-fragment-assisted complementation," Anal. Chem. (2003) 75(7):1584-1589.

Paulmurugan, R. et al., "Novel fusion protein approach for efficient high-throughput screening of small molecule-mediating protein-protein interactions in cells in living animals," Cancer Res. (2005) 65(16):7413-7420.

Paulmurugan, R. eta l., "Noninvasive imaging of protein-protein interactions in living subjects by using reporter protein complementation and reconsittution strategies," Proc. Natl. Acad. Sci. USA (2002) 99(24):15608-15613.

Plainkum, P. et al., "Creation of a zymogen," Nature Structural Biology (2003) 10(2):115-119.

Qian, Z. et al., "Improving the catalytic activity of candida antartica lipase B by circular permutation," J. Am. Chem. Soc. (2005) 127:13466-13467.

Sadowski, I. et al., "A noncatalytic domain conserved among cytoplasmic protein-tyrosine kinases modifies the kinase function and transforming activity of fujinami sarcoma virus P130 gaag-fps," Mol. Cell. Biol. (1986) 6:4396-4408.

(56) References Cited

OTHER PUBLICATIONS

Sala-Newby, G., "Engineering a bioluminescent indicator for cyclic AMP-dependent protein kinase," Biochem. J. (1991) 279(Part 3):727-732.
Sala-Newby, G., "Engineering firefly luciferase as an indicator of cyclic AMP-dependent protein kinase in living cells," FEBS Letters (1992) 307(2):241-244.
Siehler, S., "Cell-based assays in GPCR drug discovery," Biotechnol. J. (2008) 3:471-483.
Spotts, J.M. et al., "Time-lapse imaging of a dynamic phosphorylation-dependent protein-protein interaction in mammalian cells," Proc. Natl Acad. Sci. USA (2002) 99(23):15142-15147.
Tanenbaum, D.M. et al., "Crystallographic comparison of the estrogen and progesterone receptor's ligand binding domains," Proc. Natl. Acad. Sci. USA (1998) 95:5998-6003.
Umezawa, Y., "Assay and screening methods for bioactive substances based on cellular signalling pathways," Reviews in Mol. Biotech. (2001) 82:357-370.
Wada et al., "Codon usage tabulated from the GenBank genetic sequence data" NAR 18: 2367-2411 (1990).
Wang, X. et al., "Effect of removal of the N-terminal amino acid residues on the activity and conformation of firefly luciferase," Intl. J. Biochem. Cell Biol. (2002) 34(8):983-991.
Waud, J.P. et al., "Engineering the C-terminus of firefly luciferase as an indicator of covalent modification of proteins," Biochim. Biophys. Acta (1996) 1292(1):89-98.
Wigdal, S.S. et al., "A novel bioluminescent protease assay using engineered firefly luciferase," Curr. Chem. Genomics (2008) 2(1):16-28.
Wiley, S.R. et al., "Identification and characterization of a new member of the TNF family that induces apoptosis," Immunity (1995) 3(6):673-682.
Ye, L. et al., "Cloning and sequencing of a cDNA for firefly luciferase from photuris pennsylvanica," Biochimica et Biophysica Acta (1997) 1339:39-52.
Zagotta, W.N. et al., "Structural basis for modulation and agonist specificity of HCN pacemaker channels," Nature (2003) 425:200-205.
Zako, T. et al., "Luminescent and substrate binding activities of firefly luciferase N-terminal domain," Biochim. Biophys. Acta—Proteins & Proteomics (2003) 1649(2):183-189.
Zhang et al., "A Simple Statistical Parameter for Use in Evaluation and Validation of High Throughput Screening Assays," Biomol Screen. 4:67-73 (1999).
Zhang, J. et al., "Creating new fluorescent probes for cell biology," Mol. Cell Biol. (2002) 3:906-918.
Zhao, H. et al., "Emission spectra of bioluminescent reporters and interaction with mammalian tissue determine the sensitivity of detection in vivo," J. Biomed. Optics (2005) 10(4):041230-1-041230-9.
Canadian Patent Office Action for Application No. 2648263 dated Feb. 8, 2011 (4 pages).
Chinese Patent Office Action for Application No. 200780020577.7 dated Jun. 4, 2010 (9 pages) with translation.
European Patent Office Action for Application No. 07754666.1 dated Jan. 11, 2010 (3 pages).
European Patent Office Action for Application No. 07754666.1 dated Feb. 13, 2009 (6 pages).
European Patent Office Action for Application No. 07754666.1 dated Aug. 19, 2011 (4 pages).
European Patent Office Partial Search Report for Application No. 11155576.9 dated May 3, 2011 (7 pages).
European Patent Office Action for Application No. 11155576.9 dated Sep. 9, 2011 (12 pages).
European Patent Office Action for Application No. 07754666.1 dated Jun. 11, 2012 (4 pages).
European Patent Office Action for Application No. 07754666.1 dated Mar. 25, 2013 (4 pages).
European Patent Office Action for Application No. 11155576.9 dated Jul. 13, 2012 (4 pages).
European Patent Office Action for Application No. 04809862.8 dated Mar. 19, 2007 (3 pages).
European Patent Office Examination Report for Application No. 04809862.8 dated Dec. 28, 2007 (3 pages).
European Patent Office Action for Application No. 04809862.8 dated Apr. 8, 2009 (4 pages).
European Patent Office Examination Report for Application No. 04809862.8 dated Dec. 23, 2009 (4 pages).
European Patent Office Action for Application No. 04809862.8 dated Dec. 1, 2010 (4 pages).
European Patent Office Action for Application No. 10182746.7 dated Feb. 10, 2011 (7 pages).
European Patent Office Action for Application No. 10182746.7 dated Jan. 17, 2013 (4 pages).
European Patent Office Action for Application No. 10182742.6 dated Jan. 10, 2013 (5 pages).
European Patent Office Action for Application No. 09750966.5 dated Apr. 19, 2011 (3 pages).
International Search Report and Written Opinion for Application No. PCT/US2007/008176 dated Dec. 27, 2007 (18 pages).
Invitation to Pay Additional Fees and Partial Search Report for Application No. PCT/US2007/008176 dated Feb. 10, 2007 (7 pages).
International Search Report and Written Opinion for Application No. PCT/US2004/032705 dated Dec. 9, 2005 (20 pages).
Invitation to Pay Additional Fees and Partial Search Report for Application No. PCT/US2004/032705 dated May 19, 2005 (9 pages).
International Search Report and Written Opinion for Application No. PCT/US2009/003132 dated Nov. 12, 2009 (10 pages).
International Search Report and Written Opinion for Application No. PCT/US2011/036110 dated Jul. 28, 2011 (15 pages).
PCT/US2012/064675 Invitation to Pay Additional Fees and International Search Report dated Jan. 31, 2013 (9 pages).
PCT/US2012/064675 International Search Report and Written Opinion dated Apr. 3, 2013 (19 pages).
Japanese Patent Office Action for Application No. 2006-534242 dated Sep. 1, 2010 (9 pages).
Japanese Patent Office Action for Application No. 2006-534242 dated Dec. 15, 2011 (6 pages) with English translation.
Japanese Patent Office Action for Application No. 2011-43966 dated May 1, 2013 (6 pages) English translation.
Japanese Patent Office Action for Application No. 2009-504249 dated Jun. 9, 2011 (10 pages).
Japanese Patent Office Action for Application No. 2011-269846 dated May 14, 2012 (Original and English Translation, 8 pages).
Japanese Patent Office Action for Application No. 2009-504249 dated May 10, 2012 (English Translation Only, 4 pages).
Japanese Patent Office Action for Application No. 2009-504249 dated Feb. 7, 2013 (Original and English Translation, 7 pages).
Singapore Patent Office Search Report and Written Opinion for Application No. 200807470-0 dated Jan. 29, 2010 (17 pages).
United States Patent Office Action for U.S. Appl. No. 10/957,433 dated Jan. 7, 2010 (6 pages).
United States Patent Office Action for U.S. Appl. No. 10/957,433 dated Jul. 21, 2009 (8 pages).
United States Patent Office Action for U.S. Appl. No. 10/957,433 dated Feb. 12, 2009 (5 pages).
United States Patent Office Action for U.S. Appl. No. 10/957,433 dated Sep. 4, 2008 (7 pages).
United States Patent Office Action for U.S. Appl. No. 10/957,433 dated Mar. 21, 2008 (10 pages).
United States Patent Office Action for U.S. Appl. No. 10/957,433 dated Oct. 12, 2007 (9 pages).
United States Patent Office Action for U.S. Appl. No. 10/957,433 dated Mar. 11, 2011 (6 pages).
United States Patent Office Action for U.S. Appl. No. 10/957,433 dated Jan. 31, 2012 (3 pages).
United States Patent Office Action for U.S. Appl. No. 13/454,464 dated Apr. 30, 2013 (8 pages).
United States Patent Office Action for U.S. Appl. No. 11/732,105 dated Jun. 7, 2011 (22 pages).
United States Patent Office Action for U.S. Appl. No. 11/732,105 dated Nov. 23, 2011 (19 pages).

(56) References Cited

OTHER PUBLICATIONS

United States Patent Office Action for U.S. Appl. No. 12/454,643 dated Jan. 31, 2012 (13 pages).
United States Patent Office Final Rejection for U.S. Appl. No. 12/454,643 dated Jun. 15, 2012 (9 pages).
United States Patent Office Action for U.S. Appl. No. 13/105,648 dated Jun. 20, 2013 (14 pages).
De Wet, J.R., et al., 1987, "Firefly luciferase gene: structure and expression in mammalian cells", Molecular and Cellular Biology, vol. 7, No. 2, pp. 725-737.
Tatsumi, H., et al., 1992, "Molecular cloning and expression in *Escherichia coli* of a eDNA clone encoding luciferase of a firefly, Lucio la lateralis", Biochimica et Biophysica Acta, vol. 1131, pp. 161-165.
Devine, J.H., et al., 1993, "Luciferase from the East European firefly Luciola mingrelica: cloning and nucleotide sequence of the eDNA, overexpression in *Escherichia coli* and purification of the enzyme", Biochimica et Biophysica Acta, vol. 1173, pp. 121-132.
Sala-Newby, G.B., et al., 1996, "Sequence and biochemical similarities between the luciferases of the glow-worm *Lampyris noctiluca* and the firefly *Photinus pyralis*", Biochemical Journal, vol. 313, pp. 761-767.
Alipour B.S., et al., 2004, "Molecular cloning, sequence analysis, and expression of a eDNA encoding the luciferase from the glow-worm, *Lampyris turkestanicus*", Biochemical and Biophysical Research Communications, vol. 325, pp. 215-222.

Viviani, V. R., et al., 2004, "Cloning and characterization of the eDNA for the Brazilian *Cratomorphus distinctus* larval firefly luciferase: similarities with European *Lampyris noctiluca* and Asiatic *Pyrocoelia luciferases*", Comparative Biochemistry and Physiology, Part B, vol. 139, pp. 151-156.
Li, X., et al., 2006, "Phylogenetic relationship of the firefly, *Diaphanes pectineal* is based on the DNA sequence and gene structure of luciferase", Dong Wu Xue Za Zhi [Zoological Research], vol. 27, No. 4, pp. 367-374.
Oba, Y., et al., 2010, "Identification and characterization of a luciferase isotype in the Japanese firefly, *Luciola cruciata*, involving in the dim glow of firefly eggs", Biochemistry, vol. 49, pp. 10788-10795.
European Patent Office Action for Application No. 10182742.6 dated Oct. 15, 2013 (4 pages).
Japanese Patent Office Action for Application No. 2011-510512 dated Nov. 25, 2013 (Original, 5 pages).
United States Patent Office Notice of Allowance for U.S. Appl. No. 13/105,648 dated Jan. 10, 2014 (12 pages).
European Patent Office Action for Application No. 11155576.9 dated Nov. 20, 2013 (4 pages).
United States Patent Office Action for U.S. Appl. No. 11/732,105 dated Sep. 4, 2013 (10 pages).
European Patent Office Action for Application No. 11720279.6 dated Sep. 24, 2013 (7 pages).

\* cited by examiner

Figure 3

```
  1  MVKREKNVIYGPEPLHPLEDLTAGEMLFRALRKHSHLPQALVDVVGDESL
 51  SYKEFFEATVLLAQSLHNCGYKMNDVVSICAENNTRFFIPVIAAWYIGMI
101  VAPVNESYIPDELCKVMGISKPQIVFTTKNILNKVLEVQSRTNFIKRIII
151  LDTVENIHGCESLPNFISRYSDGNIANFKPLHFDPVEQVAAILCSSGTTG
201  LPKGVMQTHQNICVRLIHALDPRVGTQLIPGVTVLVLPFFHAFGFSITL
251  GYFMVGLRVIMFRRFDQEAFLKAIQDYEVRSVINVPSVILFLSKSPLVDK
301  YDLSSLRELCCGAAPLAKEVAEVAAKRLNLPGIRCGFGLTESTSANIHSL
351  RDEFKSGSLGRVTPLMAAKIADRETGKALGPNQVGELCIKGPMVSKGYVN
401  NVEATKEAIDDDGWLHSGDFGYYDEDEHFYVVDRYKELIKYKGSQVAPAE
451  LEEILLKNPCIRDVAVVGIPDLEAGELPSAFVVKQPGKEITAKEVYDYLA
501  ERVSHTKYLRGGVRFVDSIPRNVTGKITRKELLKQLLEKAGG
```

The most active linker mutants have insertions at Val399 and Asn401

| clone# | location (nt) | location (aa) | activity 1 | activity 2 |
|---|---|---|---|---|
| 1 | 1125 | Thr376 | 166 | 195 |
| 3 | 1217 | Lys406 | 239 | 422 |
| 6 | 73 | Gly25 | 103 | 170 |
| 8 | 1205 | Val402 | 130 | 259 |
| 9 | 1219 | Glu407 | 190 | 333 |
| 10 | 1216 | Lys406 | 261 | 344 |
| 11 | 72 | Glu25 | 141 | 180 |
| 12 | 1191 | Tyr398 | 126 | 200 |
| 13 | 1193 | Tyr398 | 221 | 230 |
| 14 | 1215 | Thr405 | 242 | 336 |
| 16 | 1217 | Lys406 | 311 | 376 |
| 20 | 1201 | Asn401 | 574 | 538 |
| 23 | 1125 | Thr376 | 122 | 96 |
| 24 | 1193 | Tyr398 | 174 | 143 |
| 25 | 1468 | Ile490 | 131 | 160 |
| 26 | 1071 | Ser358 | 316 | 271 |
| 27 | 1201 | Asn401 | 618 | 621 |
| 30 | 1224 | Ile409 | 166 | 129 |
| 31 | 1199 | Asn400 | 204 | 143 |
| 34 | 73 | Glu25 | 119 | 141 |
| 35 | 63 | Leu21 | 106 | 156 |
| 36 | 1135 | Leu379 | 138 | 98 |
| 38 | 351 | Met117 | 177 | 239 |
| 43 | 1196 | Val399 | 500 | 587 |
| 45 | 1207 | Glu403 | 193 | 196 |
| 50 | 1071 | Ser358 | 244 | 234 |
| 54 | 1219 | Glu407 | 214 | 153 |
| positive control | | | 27000 | 29000 |
| negative control | | | 20 | 27 |

2% of wt activity
20-fold > background

|  | | % activity |
|---|---|---|
| Wt | 398YVNNVEATKEAI409 | 50% |
| ss | YVNNVEATKEAV | 100% |
| 6His | YVNHHHHHHNVEATKEAV | 27% |
| Flag | YVNDYKDDDDKNVEATKEAV | 12% |
| DEVD | YVNDEVDNVEATKEAV | 20% |
| Pka | YVNLRRASLGNVEATKEAV | 12% |
| SgfPme | YAIASLNV | 10% |

Figure 6C

|  |  | % activity* |
|---|---|---|
| Wt | 398YVNNVEATKEAI409 | 50% |
| ss | YVNNVEATKEAV | 100% |
| SARS1 | YSITSAVLQSGFRKMAV | 38% |
| SARS2 | YTSAVLQSGFRV | 19% |
| SARS3 | YVNTSAVLQSGFRNVEATKEAV | 64% |
| SARS4 | YQCSGVTFQGKFKKIVV | 36% |
| SARS5 | YSGVTFQGKFKV | 1% |
| SARS6 | YVNSGVTFQGKFKNVEATKEAV | 50% |

```
  1    MEDAKNIKKG  PAPFYPLEDG  TAGEQLHKAM  KRYALVPGTI  AFTDAHIEVD

51    ITYAEYFEMS  VRLAEAMKRY  GLNTNHRIVV  CSENSLQFFM  PVLGALFIGV

101    AVAPANDIYN  ERELLNSMGI  SQPTVVFVSK  KGLQKILNVQ  KKLPIIQKII

151    IMDSKTDYQG  FQSMYTFVTS  HLPPGFNEYD  FVPESFDRDK  TIALIMNSSG

201    STGLPKGVAL  PHRTACVRFS  HARDPIFGNQ  IIPDTAILSV  VPFHHGFGMF

251    TTLGYLICGF  RVVLMYRFEE  ELFLRSLQDY  KIQSALLVPT  LFSFFAKSTL

301    IDKYDLSNLH  EIASGGAPLS  KEVGEAVAKR  FHLPGIRQGY  GLTETTSAIL

351    ITPEGDDKPG  AVGKVVPFFE  AKVVDLDTGK  TLGVNQRGEL  CVRGPMIMSG

401    YVNNPEATNA  LIDKDGWLHS  GDIAYWDEDE  HFFIVDRLKS  LIKYKGYQVA

451    PAELESILLQ  HPNIFDAGVA  GLPDDDAGEL  PAAVVVLEHG  KTMTEKEIVD

501    YVASQVTTAK  KLRGGVVFVD  EVPKGLTGKL  DARKIREILI  KAKKGGKIAV
```

Figure 7A

Figure 15
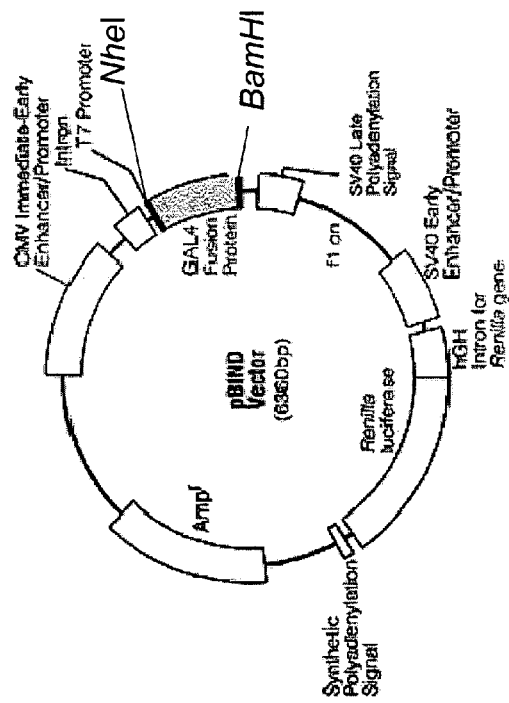
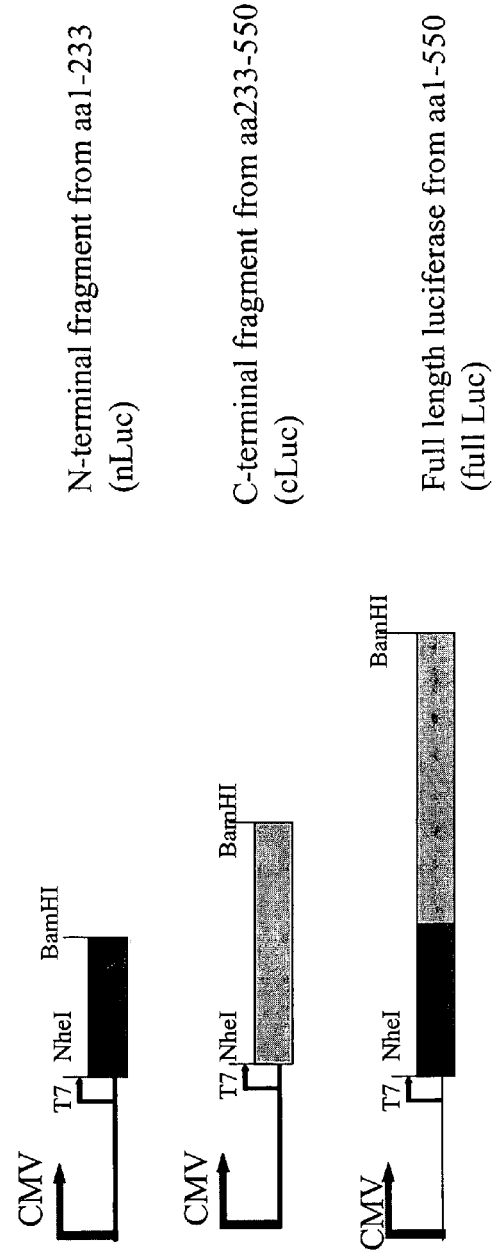
Replace GAL4 region (NheI-BamHI) with luc fragments
N-terminal fragment from aa1-233 (nLuc)
C-terminal fragment from aa233-550 (cLuc)
Full length luciferase from aa1-550 (full Luc)

LUCIFERASE BIOSENSOR

CROSS-REFERENCE TO RELATED APPLICATIONS

This application is a divisional of U.S. application Ser. No. 10/957,433, filed Oct. 1, 2004, now U.S. Pat. No. 8,183,036, which claims priority to U.S. Provisional Application No. 60/510,187, filed Oct. 10, 2003, the disclosures of which are both incorporated by reference herein.

SEQUENCE LISTING

The instant application contains a Sequence Listing which the computer readable form was transferred from U.S. application Ser. No. 10/957,433 on May 11, 2012 to the instant application and is hereby incorporated by reference in its entirety.

FIELD OF THE INVENTION

This invention relates to the field of biochemical assays and reagents. More specifically, this invention relates to modified reporter proteins, e.g., luminescent reporter proteins, and to methods for their use.

BACKGROUND

Luciferases are enzymes that catalyze the oxidation of a substrate (e.g., luciferin) with the concomitant release of photons of light. Luciferases have been isolated from numerous species, including Coleopteran arthropods and many sea creatures. Because it is easily detectable and its activity can be quantified with high precision, luciferase/substrate pairs have been used widely to study gene expression and protein localization. Unlike another reporter protein, green fluorescent protein (GFP), which requires up to 30 minutes to form chromophore, the products of luciferases can be detected immediately upon completion of synthesis of the polypeptide chain (if substrate and oxygen are also present). In addition, no post-translational modifications are required for enzymatic activity, and the enzyme contains no prosthetic groups, bound cofactors, or disulfide bonds. Luciferase is a useful reporter in numerous species and in a wide variety of cells.

Luciferases possess additional features that render them particularly useful as reporter molecule's for biosensing, i.e., molecules which reveal properties of a biological system. Signal transduction in biosensors (sensors which comprise a biological component) generally involves a two-step process: signal generation through a biological component, and signal transduction and amplification through an electrical component. Signal generation is typically achieved through binding or catalysis. Conversion of these biochemical events into an electrical signal is typically based on electrochemical or caloric detection methods, which are limited by the free energy change of the biochemical reactions. For most reactions, this is less than the energy of hydrolysis for two molecules of ATP, or about 70 kJ/mole. However, the luminescence elicited by luciferases has a much higher energy content. For instance, the reaction catalyzed by firefly luciferase (560 nm) emits 214 kJ/mole of energy. Furthermore, the reaction catalyzed by luciferase is one of the most efficient bioluminescent reactions known, having a quantum yield of nearly 0.9. Luciferase is thus an extremely efficient transducer of chemical energy.

Luciferase biosensors have been described. For example, Sala-Newby et al. (1991) disclose that a *Photinus pyralis* luciferase cDNA was amplified in vitro to generate cyclic AMP-dependent protein kinase phosphorylation sites. In particular, a valine at position 217 was mutated to arginine to generate a site, RRFS, and the heptapeptide kemptide, the phosphorylation site of the porcine pyruvate kinase, was added at the N- or C-terminus of the luciferase. Sala-Newby et al. relate that the proteins carrying phosphorylation sites were characterized for their specific activity, pI, effect of pH on the color of the light emitted, and effect of the catalytic subunit of protein kinase A in the presence of ATP. They found that only one of the recombinant proteins (RRFS) was significantly different from wild-type luciferase and that the RRFS mutant had a lower specific activity, lower pH optimum, emitted greener light at low pH and, when phosphorylated, decreased its activity by up to 80%. It is disclosed that the latter effect was reversed by phosphatase.

Waud et al. (1996) engineered protein kinase recognition sequences and proteinase sites into a *Photinus pyralis* luciferase cDNA. Two domains of the luciferase were modified by Waud et al.; one between amino acids 209 and 227 and the other at the C-terminus, between amino acids 537 and 550. Waud et al. disclose that the mutation of amino acids between residues 209 and 227 reduced bioluminescent activity to less than 1% of wild-type recombinant, while engineering peptide sequences at the C-terminus resulted in specific activities ranging from 0.06%-120% of the wild-type recombinant luciferase. Waud et al. also disclose that addition of a cyclic AMP dependent protein kinase catalytic subunit to a variant luciferase incorporating the kinase recognition sequence, LRRASLG (SEQ ID NO:107), with a serine at amino acid position 543, resulted in a 30% reduction activity. Alkaline phosphatase treatment restored activity. Waud et al. further disclose that the bioluminescent activity of a variant luciferase containing a thrombin recognition sequence, LVPRES (SEQ ID NO: 108), with the cleavage site positioned between amino acids 542 and 543, decreased by 50% when incubated in the presence of thrombin.

Ozawa et al. (2001) describe a biosensor based on protein splicing-induced complementation of rationally designed fragments of firefly luciferase. Protein splicing is a posttranslational protein modification through which inteins (internal proteins) are excised out from a precursor fusion protein, ligating the flanking exteins (external proteins) into a contiguous polypeptide. It is disclosed that the N- and C-terminal intein DnaE from *Synechocystis* sp. PCC6803 were each fused respectively to N- and C-terminal fragments of a luciferase. Protein-protein interactions trigger the folding of DnaE intein, resulting in protein splicing, and thereby the extein of ligated luciferase recovers its enzymatic activity. Ozawa et al. disclose that the interaction between known binding partners, phosphorylated insulin receptor substrate 1 (IRS-1) and its target N-terminal SH2 domain of PI 3-kinase, was monitored using a split luciferase in the presence insulin.

Paulmurugan et al. (2002) employed a split firefly luciferase-based assay to monitor the interaction of two proteins, i.e., MyoD and Id, in cell cultures and in mice using both complementation strategy and an intein-mediated reconstitution strategy. To retain reporter activity, in the complementation strategy, fusion proteins need protein interaction, i.e., via the interaction of the protein partners MyoD and Id, while in the reconstitution strategy, the new complete reporter protein formed via intein-mediated splicing maintains it activity even in the absence of a continuing interaction between the protein partners.

A protein fragment complementation assay is disclosed in Michnick et al. (U.S. Pat. Nos. 6,270,964, 6,294,330 and 6,428,951). Specifically, Michnick describe a split murine dihydrofolate reductase (DHFR) gene-based assay in which an N-terminal fragment of DHFR and a C-terminal fragment of DHFR are each fused to a GCN4 leucine zipper sequence. DHFR activity was detected in cells which expressed both fusion proteins. Michnick et al. also describe another complementation approach in which nested sets of S1 nuclease generated deletions in the aminoglycoside kinase (AK) gene are introduced into a leucine zipper construct, and the resulting sets of constructs introduced to cells and screened for AK activity.

What is needed is an improved recombinant reporter protein for use as a biosensor, e.g., in detecting cellular events such as protein-protein interactions, with a high degree of specificity and a high quantum yield.

SUMMARY OF THE INVENTION

The invention provides an improved gene product, e.g., a modified reporter protein such as a modified beetle luciferase, which, in the presence of another molecule (one or more molecules of interest), or under certain conditions, has one or more altered activities. In one embodiment, the amino acid sequence of the modified reporter protein is different than the amino acid sequence of a corresponding unmodified (native, wild-type or parental) reporter protein as a result of one or more modifications at a site (residue) or in a region which is tolerant to modification, e.g., tolerant to an insertion, a deletion, circular permutation, or any combination thereof. One or more modifications may be internal to the N- or C-terminus of the unmodified reporter protein, and/or may be at the N- and/or C-terminus of the unmodified reporter protein, e.g., a deletion and/or insertion of one or more amino acid residues, thereby yielding a modified reporter protein. The modification(s) may include the introduction of one or more discreet (isolated) amino acid sequences which directly or indirectly interact with a molecule of interest and/or is/are otherwise sensitive to changes in conditions, and optionally may include the deletion of one or more amino acids, e.g., at a site or in a region tolerant to modification including the N- and/or C-terminus of the unmodified reporter protein, so long as the resulting modified reporter protein has reporter activity before and/or after the interaction with the molecule of interest, such as an exogenous agent, or a change in conditions. For instance, the modified reporter protein may include deletions at the N- or C-terminus of 1 to about 10 or 15 residues, or any integer in between, relative to the corresponding unmodified reporter protein. The modification may be the absence of a peptide bond in the modified reporter protein between two amino acids which are linked via a peptide bond in the corresponding unmodified reporter protein, in conjunction with a peptide bond in the modified reporter protein between residues found at or near the N-terminal and C-terminal residues of the corresponding unmodified reporter protein, yielding a circularly permuted reporter protein, which optionally includes an amino acid sequence which directly or indirectly interacts with a molecule of interest or is otherwise sensitive to changes in conditions. The modified reporter protein may thus be employed to detect reversible interactions, e.g., binding of two or more molecules, formation of disulfide bonds or other conformational changes or changes in conditions, such as pH, temperature or solvent hydrophobicity, or irreversible interactions, e.g., cleavage of a peptide bond, via an alteration in the activity of the modified reporter protein, such as an alteration in light intensity, color or kinetic profile.

As described hereinbelow, Tn5 was employed to prepare a library of insertions of DNA encoding 19 amino acids into a click beetle luciferase nucleic acid sequence. Analysis of 416 clones with insertions showed that about 10% (52) of the clones had partial activity, e.g., activities up to 2% of wild-type. Of the 52 clones, 27 clones had insertions in the luciferase open reading frame, and 16 of those insertions were between residues 398 to 409 (the "hinge" region). In particular, in-frame insertions resulting in modified click beetle luciferases with detectable activity were at residue 21, 25, 117, 358, 376, 379, 398, 399, 400, 401, 402, 403, 405, 406, 407, 409 or 490 of click beetle luciferase, i.e., those residues and/or regions near those residues are tolerant to modification including insertions. Thus, the invention includes a modified beetle luciferase with a modification at a residue, for instance residue 21, 25, 117, 358, 376, 379, 398, 399, 400, 401, 402, 403, 405, 406, 407, 409 or 490, or in a region corresponding to residue 15 to 30, e.g., residue 21 or 25, residue 112 to 122, e.g., residue 117, residue 352 to 362, for instance, residue 358, residue 371 to 384, e.g., residue 379, residue 393 to 414, or residue 485 to 495, of a click beetle luciferase. Corresponding positions may be identified by aligning luciferase sequences. In particular, the invention includes a modified beetle luciferase with a modification in the hinge region of beetle luciferase, e.g., residues corresponding to residues 390 to 409 of click beetle luciferase, as well as other regions which can tolerate modification.

As also described herein, Tn7 was employed to prepare a library of insertions into a firefly luciferase nucleic acid sequence. In-frame insertions resulting in modified firefly luciferases with detectable activity were at residue 7, 121, 233, 267, 294, 303, 361, 540 or 541 of firefly luciferase, i.e., those residues and/or regions near those residues are tolerant to modifications including insertions. Accordingly, the invention includes a modified beetle luciferase with a modification at a residue or in a region corresponding to residue 2 to 12, residue 116 to 126, residue 228 to 238, residue 262 to 272, residue 289 to 308, residue 356 to 366, or residue 535 to 546, of a firefly luciferase. Corresponding positions may be identified by aligning luciferase sequences.

Thus, in one embodiment, the reporter protein is a beetle luciferase, and the amino acid sequence of the modified beetle luciferase is different than the amino acid sequence of a corresponding unmodified beetle luciferase as a result of one or more modifications at a site or in a region which is tolerant to modification. For example, in one embodiment, the modified beetle luciferase has a detectable activity and includes an insertion of one or more amino acids relative to a corresponding unmodified beetle luciferase at a site or in a region which is tolerant to modification, which insertion is internal to the N- and C-terminus of the modified beetle luciferase. In one embodiment, a modified beetle luciferase comprises an insertion of 2 or more, e.g., 3, 4, 5, 10, 20, 50, 100, 200, 300 or more, but less than about 500, or any integer in between, amino acid residues. In one embodiment, a modified beetle luciferase of the invention comprises an internal insertion of at least 4 amino acids at a residue or in a region which is tolerant to modification, which insertion includes an amino acid sequence which directly interacts with a molecule of interest, e.g., an insertion which includes a recognition sequence for the molecule of interest, or indirectly acts with the molecule of interest, e.g., via another molecule. In one embodiment, the modified beetle luciferase with an internal insertion further comprises an internal deletion of beetle luciferase sequences, e.g., a deletion of 1 or more, but less than about 100, for instance less than 50, 40, 30, 20, 10 or 5, or any integer in between, residues.

In one embodiment, the modified beetle luciferase has a deletion relative to a corresponding unmodified beetle luciferase, at a site or in a region which is tolerant to modification. In one embodiment, a modified beetle luciferase of the invention comprises a deletion of at least 50, e.g., at least 100, contiguous amino acid residues relative to a corresponding unmodified beetle luciferase, i.e., the modified beetle luciferase is a fragment of a full-length unmodified beetle luciferase sequence, e.g., a fragment of at least 50, e.g., at least 100, contiguous amino acid residues, for instance, a fragment which has at least 5%, e.g., 10%, fewer residues than the corresponding full-length unmodified beetle luciferase, and an insertion of an amino acid sequence which directly or indirectly interacts with a molecule of interest or is otherwise sensitive to conditions. Such a modified beetle luciferase may be employed in a protein complementation assay, e.g., where a detectable activity of the luciferase increases in the presence of another fragment of the luciferase which is linked to a molecule of interest, or in a protein recombination assay, for instance, intein-mediated recombination. In one embodiment, a beetle luciferase fragment (without one or more heterologous sequences) has a detectable activity which is less than, e.g., about 0.001%, 0.01%, 0.1% or 1%, the activity of the corresponding full-length unmodified beetle luciferase and, when combined with a complementing fragment (without one or more heterologous sequences), has an increase in activity relative to either fragment of greater than 3-fold, e.g., 10-, or 50- to 100-fold or more. For instance, in one embodiment, the N-terminal beetle luciferase fragment has at least 0.001% but less than 1%, and the C-terminal beetle luciferase fragment has at least 0.01% but less than 5%, the activity of the corresponding full-length unmodified beetle luciferase. In another embodiment, a modified beetle luciferase of the invention is a fragment which has a deletion of at least 50, e.g., at least 100, contiguous amino acid residues relative to a corresponding unmodified beetle luciferase, an insertion of an amino acid sequence which directly or indirectly interacts with a molecule of interest or is otherwise sensitive to conditions, and an insertion of heterologous, e.g., non-beetle luciferase, sequences, which insertions preferably do not increase but may individually or together decrease the activity of the beetle luciferase fragment, but which, once removed, result in a truncated beetle luciferase with increased activity relative to the modified beetle luciferase.

As further described herein, circularly permuted firefly and click beetle luciferases, having a N-terminus at a residue or in a region which is tolerant to modification in the corresponding noncircularly permuted beetle luciferase, and optionally including an amino acid sequence which directly or indirectly interacts with a molecule of interest, e.g., a protease recognition site or a kinase site, were prepared and shown to have detectable activity, which activity was altered in the presence of the molecule of interest, for instance, a suitable protease or kinase in constructs which encoded a protease recognition site or a kinase site, respectively, in the circularly permuted luciferase. Hence, in one embodiment, a modified beetle luciferase of the invention comprises an amino acid sequence which is circularly permuted relative to the amino acid sequence of a corresponding unmodified beetle luciferase, resulting in a new N- and C-terminus in the modified beetle luciferase, at least one of which is at a site or in a region which is tolerant to modification. In another embodiment, the circularly permuted beetle luciferase includes other modifications, including but not limited to insertions and/or deletions internal to the N- or C-terminus of the circularly permuted beetle luciferase, for instance, an insertion and/or deletion, e.g., at or near the N- and C-terminus of the corresponding unmodified beetle luciferase such as at residues corresponding to residues 1 to about 10 or 15, or any integer in between, of the N-terminus and/or corresponding to the last residue or about the last 15, or any integer in between 1 and 15, residues of the C-terminus of the corresponding unmodified beetle luciferase. Thus, the N- and C-termini of a reporter protein can be altered via circular permutation, and the resulting permuted molecule may have one or more activities of the nonpermuted reporter protein. Accordingly, a circularly permuted reporter protein may be employed in a protein complementation assay or in a protein recombination assay. Moreover, a circularly permuted reporter protein may be engineered to have functionality by introducing an amino acid sequence which directly or indirectly interacts with a molecule of interest or is otherwise sensitive to changes in conditions. In one embodiment, a circularly permuted reporter protein of the invention is a zymogen.

In one embodiment, in the absence of the molecule of interest, the activity of a modified reporter protein such as a modified beetle luciferase is less than the activity of a corresponding unmodified reporter protein, e.g., the reporter activity of the modified beetle luciferase is about 0.001%, 0.01%, 0.1%, 1%, 10%, 20%, 50%, 70% or more, but less than 100% that of a corresponding unmodified beetle luciferase, the activity of which modified reporter protein is optionally detectable. In another embodiment, in the absence of the molecule of interest, the activity of a modified reporter protein such as a modified beetle luciferase is greater than the activity of a corresponding unmodified reporter protein, e.g., the reporter activity of the modified beetle luciferase is about 1.5-fold, e.g., at least 2-, 3- or 5-fold or more, that of a corresponding unmodified beetle luciferase. In the presence of the molecule of interest, the activity of the modified reporter protein is detectably altered. For instance, a detectable alteration in activity of a modified beetle luciferase in the presence of a molecule of interest is an alteration of at least 0.001%, 0.01%, 0.1%, 1%, 10%, or 100%, and up to 2-fold, 4-fold, 10-fold, 100-fold, 1,000-fold, 10,000-fold or more, relative to the activity of the modified beetle luciferase in the absence of the molecule of interest. Thus, the physical proximity of a molecule of interest which interacts with a modification present in the modified reporter protein but not the corresponding unmodified reporter protein, alters, e.g., decreases, eliminates or increases, the activity of the modified reporter protein. For example, a modified beetle luciferase may comprise an internal insertion relative to a corresponding unmodified beetle luciferase, which insertion comprises a protease recognition site, i.e., a site which is cleaved by a protease. The luminescent signal of such a modified beetle luciferase in the presence of the protease may be decreased, eliminated or increased relative to the luminescent signal of the modified beetle luciferase in the absence of the protease or the luminescent signal of the corresponding unmodified beetle luciferase in the presence or absence of the molecule of interest. Alternatively, a modified beetle luciferase which comprises a deletion relative to a corresponding unmodified beetle luciferase, may be fused to a ligand which interacts with a molecule of interest. A complementing second fragment of a beetle luciferase is fused to the molecule of interest and the two fusions are allowed to interact, an interaction which alters, e.g., increases, the activity of the resulting complex relative to the activity of either fusion alone. In one embodiment, one fragment of a beetle luciferase has residues corresponding to residues about 1 to 126, about 1 to about 238, about 1 to about 272, about 1 to about 308, about 1 to about 366, about 116 to about 550, about 228 to about 550, about 262 to about 550, about 289 to about 550, or about 356 to about 550, or any integer in between, of a firefly luciferase, or residues about 1 to about 122, about 1 to about 362, about 1 to about 384, about 1 to about 414, about 352 to about 542, about 371 to about 542, or about 393 to about 542, or any integer in between, of a click beetle luciferase.

The invention also provides for a modified reporter protein which includes heterologous sequences at the N-terminus and C-terminus of a reporter protein, i.e., the modified protein is a fusion protein, which heterologous sequences noncovalently interact, that is, the two heterologous sequences are binding partners. In one embodiment, the modified reporter protein is a circularly permuted beetle luciferase which includes heterologous sequences at the N-terminus and C-terminus. In one embodiment, in the absence of one or more exogenous agents (at least one of which may be a molecule of interest, e.g., one which is to be detected or identified in a sample), a modified reporter protein which has both heterologous sequences, one at the N-terminus and the other at the C-terminus, has less, the same or greater activity than a corresponding unmodified reporter protein. In one embodiment, the modified reporter protein may also lack one or more amino acids present at the N- and/or C-terminus of the unmodified reporter protein, the absence of which does not substantially alter the reporter activity of the modified reporter protein, e.g., the activity of the reporter portion the modified reporter protein is at least 0.001%, 0.01%, 0.1%, 1%, 10%, 50%, 100% or greater than the activity of a corresponding reporter protein without the deletion(s). In one embodiment, in the presence of one or more exogenous agents or under specified conditions, the activity of the modified reporter protein having both heterologous sequences, but not the corresponding reporter protein without the heterologous sequences (that is the corresponding unmodified reporter protein), is detectably altered, e.g., by at least 2-, 5-, or 10-fold or more. For instance, in the presence of rapamycin, a luciferase fused to rapamycin binding protein (FRB) and FK506 binding protein (FKBP), has reduced activity relative to a luciferase which lacks FRB and FKBP. In one embodiment, in the absence of the exogenous agent(s) or under different conditions, the modified reporter protein does not have detectable activity, while in other embodiments it has detectable activity, which activity may be enhanced in the presence of at least one exogenous agent or under specified conditions. For example, the modified reporter protein in the absence of an exogenous agent may have little or no activity, but, after addition of a selected exogenous agent which enhances the noncovalent interaction of the two heterologous sequences, the activity of the modified reporter protein is enhanced. Alternatively, the activity of the modified reporter protein having both heterologous sequences may be inhibited in the presence of at least one exogenous agent or under specified conditions. In one embodiment, one heterologous sequence includes a domain, e.g., 3 or more amino acid residues, which optionally may be covalently modified, e.g., phosphorylated, that noncovalently interacts with a domain in the other heterologous sequence. Heterologous sequences useful as binding partners when fused to a beetle luciferase include but are not limited to those which interact in vitro and/or in vivo and optionally which, based on protein modeling for example, have linked sequences that do not participate in binding but are an approximate selected distance apart in the presence or absence of an exogenous agent which alters the interaction of the binding partners, such that their fusion to the ends of a beetle luciferase result in a modulatable beetle luciferase. Exemplary heterologous sequences include but are not limited to sequences such as those in FRB and FKBP, the regulatory subunit of protein kinase (PKa-R) and the catalytic subunit of protein kinase (PKa-C), a src homology region (SH2) and a sequence capable of being phosphorylated, e.g., a tyrosine containing sequence, an isoform of 14-3-3, e.g., 14-3-3t (see Mils et al., 2000), and a sequence capable of being phosphorylated, a protein having a WW region (a sequence in a protein which binds proline rich molecules (see Ilsley et al., 2002; and Einbond et al., 1996) and a heterologous sequence capable of being phosphorylated, e.g., a serine and/or a threonine containing sequence, as well as sequences in dihydrofolate reductase (DHFR) and gyrase B (GyrB).

In another embodiment, in the presence of one (first) exogenous agent, a modified reporter protein which includes heterologous sequences at the N-terminus and C-terminus which are binding partners, has an altered activity relative to the activity in the absence of the exogenous agent, and in the presence of a different (second) exogenous agent, the activity of the modified reporter protein is altered relative to the activity in the presence of the first exogenous agent, e.g., the second exogenous agent competes with the first exogenous agent. In one embodiment, in the absence of the first exogenous agent, the modified reporter protein has no or low detectable activity, and the addition of the first exogenous agent results in an increase in the activity of the modified reporter protein, which is reversible by the addition of a second exogenous agent. In another embodiment, in the absence of the first exogenous agent, the modified reporter protein has detectable activity, and the addition of the first exogenous agent results in reduced or a lack of detectable activity, or alternatively an increase in detectable activity, which is reversible by the addition of a second exogenous agent. The modified reporter protein optionally may lack one or more amino acids at the N- and/or C-terminus relative to the unmodified reporter protein, for instance a deletion of residue 1 or residues 1 to about 10 or 15, or any integer in between, of the N-terminus and/or corresponding to the last residue or about the last 15, or any integer in between 1 and 15, residues of the C-terminus, of the corresponding unmodified reporter protein.

In yet another embodiment, a modified reporter protein includes a heterologous sequence at the N-terminus or C-terminus which heterologous sequence alters, e.g., inhibits, the activity of the modified reporter protein, which activity is modified, for instance, at least partially restored, by the addition of a first exogenous agent. Optionally, the effect of the first exogenous agent is reversibly altered by a second exogenous agent. In one embodiment, the heterologous sequence may inhibit substrate entry and the conformation of the heterologous sequence is substantially altered in the presence of the first exogenous agent such that the modified reporter protein can interact with its substrate. The modified reporter protein optionally may lack one or more amino acids at the N- and/or C-terminus of the unmodified reporter protein such as those that correspond to residues 1 to about 10 or 15, or any integer in between, of the N-terminus and/or corresponding to the last residue or about the last 15, or any integer in between 1 and 15, residues of the C-terminus, of the corresponding unmodified reporter protein. A heterologous sequence useful in this embodiment is calmodulin (CaM).

Thus, a modified reporter protein may be employed to detect reversible interactions of the binding partners, or reversible conformational changes of a heterologous sequence, which may be enhanced or inhibited by one or more agents or changes in conditions, e.g., ionic strength or temperature.

Accordingly, a modified beetle luciferase of the invention may be employed as a biosensor.

The invention also provides an isolated nucleic acid molecule (polynucleotide) comprising a nucleic acid sequence encoding a modified reporter protein of the invention. Further provided is an isolated nucleic acid molecule comprising a nucleic acid sequence encoding fusion protein comprising a modified reporter protein and one or more amino acid residues at the N-terminus (a N-terminal fusion partner) and/or C-terminus (a C-terminal fusion partner) of the modified reporter protein. Thus, as used herein, a "fusion protein" is a polypeptide which includes one or more amino acids at the N-terminus and/or C-terminus of a modified reporter protein of the invention. Preferably, the presence of one or more fusion partners in the fusion protein does not substantially alter the detectable activity of the fusion protein relative to a corresponding modified reporter protein. In one embodiment, the fusion protein comprises at least two different fusion partners, one at the N-terminus and another at the C-terminus of a modified reporter protein. The N- or C-terminal fusion partner may be a sequence used for purification, e.g., a glutathione S-transferase (GST) or a polyHis sequence, a sequence intended to alter a property of the modified reporter protein, e.g., a protein destabilization sequence or a kinase binding domain for a kinase site in the modified reporter protein at a residue or in a region which is tolerant to modifications, or a sequence which has a property which is distinguishable from one or more properties of the reporter protein in the fusion protein. In one embodiment, the fusion protein comprises a modified beetle luciferase and a fusion partner which is a reporter protein that is different than the beetle luciferase, which reporter protein is useful as an intramolecular control, e.g., a fluorescent protein. In another embodiment, the invention includes a vector comprising a nucleic acid sequence encoding a fusion protein comprising a modified beetle luciferase of the invention and a nucleic acid fragment which encodes a reporter protein that is different than the beetle luciferase in the modified beetle luciferase. Optionally, optimized nucleic acid sequences, e.g., human codon optimized sequences, encoding at least the beetle luciferase, and preferably the modified beetle luciferase or a fusion protein comprising a modified beetle luciferase, are employed in the nucleic acid molecules of the invention, as those optimized sequences can increase the strength of the signal for beetle luciferase. The optimization of nucleic acid sequences is known to the art, see, for example WO 02/16944.

The invention also includes a stable cell line that expresses a modified reporter protein, e.g., a beetle luciferase, or fusion protein of the invention, as well as an expression cassette comprising a nucleic acid molecule encoding the modified reporter protein or fusion protein of the invention, and a vector capable of expressing the nucleic acid molecule of the invention in a host cell. Preferably, the expression cassette comprises a promoter, e.g., a constitutive or regulatable promoter, operably linked to the nucleic acid sequence. In one embodiment, the expression cassette contains an inducible promoter. Also provided is a host cell, e.g., a prokaryotic cell or an eukaryotic cell such as a plant or vertebrate cell, e.g., a mammalian cell, including but not limited to a human, non-human primate, canine, feline, bovine, equine, ovine or rodent (e.g., rabbit, rat, ferret or mouse) cell, which comprises the expression cassette or vector of the invention, and a kit which comprises the nucleic acid molecule, expression cassette, vector, host cell or modified beetle luciferase or fusion protein of the invention.

A modified reporter protein of the invention may be employed in applications where unmodified reporter proteins cannot, such as, as a functional reporter to measure or detect various conditions and/or molecules of interest. For instance, a vector encoding a modified beetle luciferase comprising an insertion of a protease cleavage recognition site, or the modified beetle luciferase, is introduced to a cell, cell lysate, in vitro transcription/translation mixture, or supernatant, and the activity of the modified beetle luciferase detected or determined, e.g., at one or more time points and relative to a corresponding unmodified beetle luciferase. An alteration in luminescent activity in the cell, cell lysate, in vitro transcription/translation mixture, or supernatant over time, and/or relative to a control, e.g., a cell having the corresponding unmodified beetle luciferase, indicates the presence of the protease. For instance, the invention includes a method to detect a virus associated with severe acute respiratory syndrome. The method includes contacting a biological, e.g., a physiological tissue or fluid, sample with a modified reporter protein, e.g., a modified beetle luciferase, comprising an internal insertion relative to a corresponding unmodified reporter protein, which modified reporter protein has a detectable activity. The insertion is at a residue or in a region in the reporter protein sequence which is tolerant to modification and comprises an amino acid recognition sequence for a protease of the virus. It is detected or determined whether the activity of the modified reporter protein in the presence of the sample is altered, thereby indicating whether the sample contains the virus.

The invention also provides a method of detecting the presence of a molecule of interest. For instance, a cell is contacted with a vector comprising a promoter, e.g., a regulatable promoter, and a nucleic acid sequence encoding a modified reporter protein of the invention which comprises an insertion which interacts with the molecule of interest. In one embodiment, a transfected cell is cultured under conditions in which the promoter induces transient expression of the modified reporter protein, and a detectable activity at the modified reporter protein determined.

Also provided is a method to prepare a selected mutated polynucleotide encoding a modified reporter protein. The method includes mutating a parent polynucleotide encoding a modified reporter protein with detectable activity to yield one or more mutated polynucleotides encoding a mutated modified reporter protein. The parent polynucleotide comprises an open reading frame for the modified reporter protein which is modified relative to a corresponding unmodified reporter protein at a residue or in a region which is tolerant to modification. The modified reporter protein comprises an amino acid sequence which directly or indirectly interacts with a molecule of interest or is otherwise sensitive to conditions relative to the corresponding unmodified reporter protein. One or more mutated polynucleotides are selected which encode mutated modified reporter proteins that have an altered interaction with the molecule of interest or altered activity under certain conditions relative to the interaction or activity of the modified reporter protein. In another embodiment, the invention provides a method which includes contacting a modified reporter protein of the invention with a library of molecules, and detecting or determining whether one or more molecules interacts with the modification or a non-reporter protein sequence in the modified reporter protein.

BRIEF DESCRIPTION OF THE FIGURES

FIG. 3. Positions of Tn5 insertions (bolded) in a click beetle luciferase (SEQ ID NO:89).

FIG. 4. Activity of click beetle luciferases modified with a Tn5 insertion.

FIG. 6A. Sequence and activity of click beetle luciferases with modifications in the hinge region, including a protease recognition site, a kinase recognition site, an antibody binding site, and a metal binding site. 6 HIS=6×His-tag; FLAG=DYKDDDDK (SEQ ID NO:4); DEVD (SEQ ID NO:106)=site recognized by caspases 3/7, Pka=Pka kinase site (SEQ ID NOs. 90-96). Insertions were introduced in the hinge region of CbgLuc (1409V) using SnaBI and SalI.

FIG. 6C. Sequence and activity of click beetle luciferases with SARS virus protease recognition sites in the hinge region (SEQ ID Nos. 90-91 and 97-102). Insertions were introduced in the hinge region of CbgLuc (1409V) using SnaBI and SalI.

FIGS. 7A-D. Activity of firefly luciferases modified with an enterokinase recognition site. A) Amino acid sequence of a parental (unmodified) firefly luciferase (luc+) (SEQ ID NO:103). B) RLU in an enterokinase assay with a modified firefly luciferase having a Gly(3)Asp(4)LysGly(3) (SEQ ID NO:112) insertion after residue 233 or the parental firefly luciferase (WT). C) RLU in an enterokinase assay with a modified firefly luciferase having a ProGlyProGly(3)Asp(4)LysGly(3)ProGlyPro (SEQ ID NO:113) insertion after residue 233 or the parental firefly luciferase (WT). D) RLU in an enterokinase assay with a modified firefly luciferase having an insertion Asp(4)Lys (SEQ ID NO:114) after residue 541 or the parental firefly luciferase (WT).

FIG. 15. Schematic of pBIND vector and control luciferase construct and N- or C-terminal luciferase constructs for self assembly.

DETAILED DESCRIPTION OF THE INVENTION

Definitions

Figure 1:
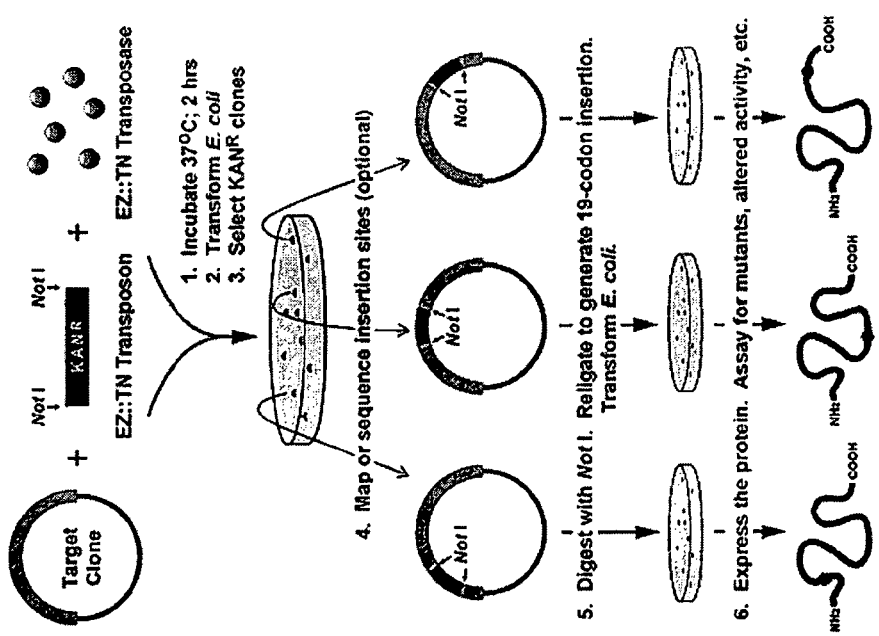
FIG. 1. Overview of the EZ::TN in frame linker insertion protocol.

The term "nucleic acid molecule", "polynucleotide", or "nucleic acid sequence" as used herein, refers to nucleic acid, DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length. An "oligonucleotide" or "primer", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporated into a polypeptide chain, or a start or stop signal. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

The term "gene" refers to a DNA sequence that comprises coding sequences and optionally control sequences necessary for the production of a polypeptide from the DNA sequence.

As used herein, the term "heterologous" nucleic acid sequence or protein refers to a sequence that relative to a reference sequence has a different source, e.g., originates from a foreign species, or, if from the same species, it may be substantially modified from the original form.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "recombinant DNA molecule" means a hybrid DNA sequence comprising at least two nucleotide sequences not normally found together in nature.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenlyation signal and optionally an enhancer sequence.

A polynucleotide having a nucleotide sequence encoding a protein or polypeptide means a nucleic acid sequence comprising the coding region of a gene, or in other words the nucleic acid sequence encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene and the long terminal repeats of the Rous sarcoma virus; and the human cytomegalovirus.

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamH I/Bcl I restriction fragment and directs both termination and polyadenylation.

Eukaryotic expression vectors may also contain "viral replicons" or "viral origins of replication." Viral replicons are viral DNA sequences that allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of source (e.g., the American Type Culture Collection, Rockland, Md.). The method of transformation or transfection and the choice of expression vehicle will depend on the host system selected. Transformation and transfection methods are well known to the art. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and anti-sense strands (i.e., the oligonucleotide may be double-stranded).

By "peptide," "protein" and "polypeptide" is meant any chain of amino acids, regardless of length or post-translational modification (e.g., glycosylation or phosphorylation). The nucleic acid molecules of the invention may also encode a variant of a naturally-occurring protein or polypeptide fragment thereof, which has an amino acid sequence that is at least 85%, 90%, 95% or 99% identical to the amino acid sequence of the naturally-occurring (native or wild-type) protein from which it is derived. The term "fusion polypeptide" or "fusion protein" refers to a chimeric protein containing a reference protein (e.g., luciferase) joined at the N- and/or C-terminus to one or more heterologous sequences (e.g., a non-luciferase polypeptide). In some embodiments, a modified polypeptide, fusion polypeptide or a portion of a full-length polypeptide of the invention, may retain at least some of the activity of a corresponding full-length functional (nonchimeric) polypeptide. In other embodiments, in the absence of an exogenous agent or molecule of interest, a modified polypeptide, fusion polypeptide or portion of a full-length functional polypeptide of the invention, may lack activity relative to a corresponding full-length functional polypeptide. In other embodiments, a modified polypeptide, fusion polypeptide or portion of a full-length functional polypeptide of the invention in the presence of an exogenous agent may retain at least some or have substantially the same activity, or alternatively lack activity, relative to a corresponding full-length functional polypeptide.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably-transfected cell line capable of producing the protein or polypeptide encoded by the gene. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "homology" refers to a degree of complementarity between two or more sequences. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

The term "purified" or "to purify" means the result of any process that removes some of a contaminant from the component of interest, such as a protein or nucleic acid. The percent of a purified component is thereby increased in the sample.

As used herein, "pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a "substantially pure" composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "poly-histidine tract" or (His tag) refers to a molecule comprising two to ten histidine residues, e.g., a poly-histidine tract of five to ten residues. A poly-histidine tract allows the affinity purification of a covalently linked molecule on an immobilized metal, e.g., nickel, zinc, cobalt or copper, chelate column or through an interaction with another molecule (e.g., an antibody reactive with the His tag).

A "protein destabilization sequence" includes, but is not limited to, a PEST sequence, for example, a PEST sequence from cyclin, e.g., mitotic cyclins, uracil permease or ODC, a sequence from the C-terminal region of a short-lived protein such as ODC, early response proteins such as cytokines, lymphokines, protooncogenes, e.g., c-myc or c-fos, MyoD, HMG CoA reductase, or S-adenosyl methionine decarboxylase, CL sequences, a cyclin destruction box, or N-degron.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene. Exemplary modified reporter proteins are encoded by nucleic acid molecules comprising modified reporter genes including, but are not limited to, modifications of a neo gene, a β-gal gene, a gus gene, a cat gene, a gpt gene, a hyg gene, a hisD gene, a ble gene, a mprt gene, a bar gene, a nitrilase gene, a galactopyranoside gene, a xylosidase gene, a thymidine kinase gene, an arabinosidase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xylE gene, an α-amylase gene, a tyrosinase gene, a luciferase (luc) gene, (e.g., a *Renilla reniformis* luciferase gene, a firefly luciferase gene, or a click beetle luciferase (*Pyrophorus plagiophthalamus*) gene), an aequorin gene, a red fluorescent protein gene, or a green fluorescent protein gene.

All amino acid residues identified herein are in the natural L-configuration. In keeping with standard polypeptide nomenclature, abbreviations for amino acid residues are as shown in the following Table of Correspondence.

TABLE OF CORRESPONDENCE

| 1-Letter | 3-Letter | AMINO ACID |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |

-continued

TABLE OF CORRESPONDENCE

| 1-Letter | 3-Letter | AMINO ACID |
| --- | --- | --- |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

I. Methods to Identify Residues or Regions of a Reporter Protein which are Tolerant to Modification Numerous methods are available to identify sites and/or regions in a reporter protein gene which may be modified, e.g., disrupted, yet when transcribed and translated, yield a desirable, for instance, a readily detectable, gene product. For instance, amplification reactions may be employed to delete and/or insert nucleotides for one or more amino acid residues in a reporter protein gene. Alternatively, transposons may be employed to prepare libraries of insertional mutations. Transposons are mobile DNA sequences found in the genomes of prokaryotes and eukaryotes. Transposon tagging has long been recognized as a powerful research tool for randomly distributing primer binding sites, creating gene "knockouts," and introducing a physical tag or a genetic tag into large target DNAs. Insertions in a reporter gene useful to prepare the modified reporter proteins of the invention are those which are internal, in frame insertions in the coding region for the reporter protein. The following examples, which are for illustration only, describe the use of a Tn5-based system (EZ::TN™ from Epicentre, Madison, Wis.) and a Tn7-based system (GPS-M Mutagenesis System, New England Biolabs, Inc.) to identify regions in a reporter gene which are tolerant to insertions.

A. Tn-5 Insertional Mutagenesis

One frequently used transposition system is the Tn5 system isolated from gram-negative bacteria. The Tn5 transposase is a small, single subunit enzyme that has been cloned and purified to high specific activity, and carries out transposition without the need for host cell factors. Moreover, Tn5 transposon insertions into target DNA are highly random, and proceed by a simple process. Tn5 transposase will transpose any DNA sequence contained between its short 19 basepair Mosaic End (ME) Tn5 transposase recognition sequences. An overview of the EZ::TN in frame linker insertion protocol is shown in FIG. 1.

i. Transposon Insertion Reaction

Target DNA Preparation

The target reporter DNA is selected as one which is not encoded by a transposon gene, e.g., a kanamycin resistance gene. While the transposon insertion reaction is not significantly inhibited by high levels of RNA contamination in target DNA preparations, if the target DNA is heavily contaminated with chromosomal DNA, which is a direct competitor for target transposition, the number of clones is reduced. Plasmid and cosmid clones can be purified by standard minilysate procedures and used as target DNA in the insertion reaction. Low copy-number vectors, for example, BAC or cosmid clones, are often contaminated with a higher molar proportion of *E. coli* chromosomal DNA, thus reducing the transposon insertion frequency. Therefore, it is preferred BAC and cosmid DNA are purified, to remove the chromosomal DNA prior to the insertion reaction.

In Vitro Transposon Insertion Reaction

Reaction conditions are optimized to maximize the efficiency of the transposon insertion while minimizing multiple insertion events. For example, an equimolar amount of the transposon is added to the moles of target DNA.

1. Prepare the transposon insertion reaction mixture by adding in the following order:
   1 µl 10× reaction buffer
   0.2 µg target DNA*
   x µl molar equivalent transposon
   x µl sterile water to a reaction volume of 9 µl
   1 µl transposase
   10 µl total reaction volume
2. Incubate the reaction mixture for 2 hours at 37° C.
3. Stop the reaction by adding µl stop solution.
   Mix and heat for 10 minutes at 70° C.
   The reaction mixture may be stored at −20° C.

ii. Selection of Transposon Insertion Clones

Transformation and Recovery

The number of transposon insertion clones obtained per reaction depends on, among other factors, the transformation efficiency of the competent cells used. The greater the transformation efficiency of the competent cells, the greater the number of insertion clones obtained. A recA⁻ strain of *E. coli* is preferred to eliminate the possibility of generating multimeric forms of the vector. Also, the host strain must not express any antibiotic resistance marker, e.g., a kanamycin resistance marker, present in the transposon.

1. Using 1 µl of the insertion reaction mixture, transform recA⁻ *E. coli*, e.g., electrocompetent cells.
2. Recover the electroporated cells by adding SOC medium to the electroporation cuvette to 1 ml final volume immediately after electroporation. Pipette the medium/cells gently to mix. Transfer to a tube and incubate on a 37° C. shaker for 30-60 minutes to facilitate cell outgrowth.

Plating and Selecting Transformants

Transposon insertion clones are selected on antibiotic-containing plates. For Tn5, kanamycin-containing plates may be used, however, the transposon can also confer resistance to neomycin and G418 in *E. coli*.

1. Plate portions of cells onto LB plates containing 50 µg/ml kanamycin.
2. To determine the transposon insertion efficiency, plate identical dilutions and dilution aliquots of the transformation reaction on a second plate containing an antibiotic specific for selecting target DNA (e.g., 100 µg/ml ampicillin for the control DNA). The transposition frequency is given by the ratio of $Kan^R/Amp^R$ clones for the control DNA.
3. Grow plates overnight at 37° C. Assuming a transposon insertion efficiency of 1% and use of high purity target DNA (i.e., little or no chromosomal DNA contamination), there are about 100-500 $Kan^R$ clones per plate.

iii. Generating an in Frame 19 Codon Insertion

Transposon Insertion Mapping

Tn5 randomly inserts into target DNA. Therefore, the transposon insertion site in each clone should be determined prior to restriction endonuclease digestion, e.g., NotI digestion, by one of three methods:

1. Insertion clones can be sequenced bidirectionally using forward and reverse transposon-specific primers. The insertion site of each clone can also be mapped prior to sequencing.
2. Insertion sites can be mapped by size analysis of PCR products using colony minilysate DNA as a template. To map the insertion sites, forward or reverse transposon-specific primers and a vector-specific flanking primers may be employed.
3. Alternatively, insertion sites can be mapped by restriction endonuclease digest(s).

Once the transposon insertion site of the desired clones is determined, the clones are individually digested with a restriction enzyme, e.g., NotI, to linearize the DNA. The linearized DNA is then purified (e.g., by agarose gel electrophoresis, column purification, and the like).

Religation and Transformation

The linearized clones are religated using T4 DNA ligase. Successful religation regenerates a single restriction site, e.g., NotI, and creates the 57 nucleotide (19 codon) insertion into all three reading frames. The religated DNA is transformed into selected cells and recombinants selected using an antibiotic marker present on the original cloning vector (e.g., ampicillin for the control DNA).

Analysis of the 19 Codon Insertion Clones

Nine of the 57 nucleotides are the result of a 9 bp sequence duplication immediately flanking the transposon insertion site. The amino acid sequence of the protein encoded by the target DNA is conserved on both sides of the 19 codon insertion.

iv. DNA Sequencing of Transposon Insertion Clones

Primer Consideration

Primers should be constructed to minimize homology to commonly used cloning vectors, and the sequence of each primer should be compared to that of the user's specific cloning vector to ensure minimal sequence homology to the vector.

Target Site Duplication

Tn5-catalyzed transposon insertion results in the generation of a 9 bp target site sequence duplication where one copy immediately flanks each side of the inserted transposon.

Distinguishing Transposon Sequence for Insert Sequence

If the primers anneal to a region near the ends of the transposon, the first sequence data obtained from each sequencing reaction is that of Transposon DNA.

B. Tn7-Based Insertional Mutagenesis

The GPS-M Mutagenesis System uses TnsABC*Transposase to insert a Tn7-based transposon randomly into a DNA target. Target DNA may be a plasmid, cosmid, BAC or purified chromosomal DNA. If the insertion site is within a translated gene segment, this will normally result in a null (loss of function) mutation. There is minimal site preference for insertion, so disruption of any open reading frame is possible. Due to target immunity, only one insertion occurs per DNA molecule in vivo over a distance of about 190 kb. Therefore, the in vitro reaction produces a population of target DNA molecules each containing the transposable element at a different position.

The transposon donor can be modified by adding to or replacing the antibiotic, e.g., kanamycin, resistance marker. The donor plasmid may be grown in standard laboratory *E. coli* strains, and the vector backbone carries a different antibiotic marker, e.g., Amp$^r$, than the transposon and an origin of replication. To destroy unreacted donor molecules and avoid undesirable reaction products, the donor can be destroyed by digestion with a rare-cutting enzyme, for instance, PI-SceI (VDE). For applications in which the mutagenized DNA is transformed into naturally-competent organisms (which take up single DNA strands), the gaps are filled-in and ligated.

i. Reaction Protocol
1. Mix the following reagents (per 20 µl reaction):

| | |
|---|---|
| 2 µl | 10 X buffer |
| 1 µl | supercoiled custom donor (0.02 µg) |
| 0.08 µg | target DNA |
| dH$_2$O | |
| 18 µl | Total Volume |

Mix well by pipetting up and down a few times.
2. Add 1 µl transposase to each tube. Mix again.
3. Incubate for 10 minutes at 37° C. This is the assembly reaction.
4. Add 1 µl start solution to each tube. Mix well by pipetting up and down a few times.
5. Incubate for 1 hour at 37° C. This is the strand transfer reaction.
6. Heat inactivate at 75° C. for 10 minutes. Note: 65° C. is not adequate.
7. Optional gap repair.
8. Add 5 µl 10× PI-SceI Buffer
   0.5 µl BSA
   18.5 µl dH$_2$O
   6 µl PI-SceI (VDE) (6 units)
9. Incubate for 1-2 hours at 37° C.
10. Incubate for 10 minutes at 75° C.
11. Transform. For chemical transformation with subcloning efficiency cells (10$^7$ per microgram of pUC), transform 1 µl and 10 µl of undiluted reaction. For electroporation (>10$^9$ per microgram of pUC), dilute 10-fold in dH$_2$O and transform 1 µl and 10 µl. To outgrow, dilute the transformation mixture into 1 ml LB or as directed by the manufacturer, and incubate for 1 hour at 37° C. with aeration. This period without selection is necessary for expression of drug resistance, especially kanamycin.

ii. General Considerations

Amount of Target

The recommended mass of target DNA (0.08 µg per reaction) works well for plasmid targets. For cosmids and BACs, a molar ratio of around 2:1 (donor to target) works well. Increasing the ratio to 4:1 decreases the efficiency slightly.

Donor:Target Ratio

The recommended donor:target mass ratio (1:4, 0.08 µg target per 20 µl reaction) is optimal. Small deviations produce only small changes in the number of recovered products. However, saturating amounts of donor inhibit the reaction and may lead to accumulation of double insertions.

Order of Addition

Water, target DNA, buffer and donor plasmid should be added first, followed by transposase. The start solution should be added only after the assembly reaction.

Assembly Reaction

If this step is omitted, the proportion of complicated products is increased.

Time of Incubation

The reaction is linear at 37° C. for at least one hour. Extremely long incubation times may lead to accumulation of double insertions.

Temperature of Incubation

The reaction proceeds, but more slowly, at room temperature and at 30° C. For reactions with BACs, 30° C. is recommended.

Heat Killing

Heating at 75° C. for 10 minutes effectively disrupts the reaction complexes. Heating at 65° C. for 20 minutes is not adequate. Phenol/chloroform extraction followed by alcohol precipitation is also effective.

Scaling the Procedure

Increase or reduce the final volume and the volume of all components by the same percentage; the relative concentrations of the two DNA species and the proteins are very important, as are the buffer conditions.

Enzyme Names

PI-SceI (VDE) is not the same as I-SceI. Use PI-SceI (VDE) to digest the donor and SceI for mapping insertions obtained.

Gap Repair

This step is not required for transformation into *E. coli* and is necessary only when the desired application involves transformation into naturally competent bacteria. Naturally competent bacteria include members of the genera *Neisseria, Haemophilus, Bacillus, Pneumococcus, Staphylococcus*, and *Streptococcus*. DNA uptake into these organisms involves degradation of one strand, concomitant with internalization of the other strand. Without gap repair, the 5-base gaps at the transposon insertion site will unlink the transposon insertion from flanking DNA on one side or the other. Organisms in which competence is induced chemically or by electroporation (e.g., *E. coli* and other enteric bacteria tissue culture cells, etc.) take up both DNA strands. Gaps at the insertion site are efficiently repaired by the cellular machinery.

iii. GAP Repair Protocol
7. Phenol/chloroform extract (501).
8. Ethanol precipitate:
   6 µl 3M NaAcetate
   100 µl EtOH
   Incubate for 20 minutes at −20° C.
   Centrifuge for 10 minutes in a microfuge
9. Resuspend in 15 µl TE.
10. 1 µl DNA Polymerase I (*E. coli*) (10 units)
    3 µl 10× EcoPol Buffer
    9 µl dNTP (at 100 µM each nucleotide; final concentration 33 µM each)
11. Incubate for 15 minutes at room temperature.
12. Add 1 µl T4 DNA ligase (400 units) and ATP to a final concentration of 1 mM.
13. Incubate for 4 hours at 16° C.
14. Phenol/chloroform extract.
15. Alcohol precipitate.
16. Resuspend in 20 µl TE.
17. Add 5 µl OX PI-SceI Buffer
    0.5 µl BSA
    18.5 µl dH$_2$O
    6 µl PI-SceI (VDE) (6 units)
18. Incubate for 1-2 hours at 37° C.
19. Incubate for 10 minutes at 75° C.
20. Transform according to the appropriate method.

iv. Donor Manipulation
1. The transposon donor must be supercoiled. The efficiency of reaction using a relaxed or linear donor is reduced by about 100-fold. The donor preparation should be good quality, but CsCl-purification is not necessary.
2. Essential recognition elements for the transposase are not dispensable. There may be stop codons in all frames reading into the transposon. Transcription can proceed into the dispensable region from outside without difficulty.
3. Transposition efficiency may decline somewhat as the transposon becomes longer.

4. For best results, ensure that your transposon donor plasmid is monomeric.
5. The PI-SceI digestion step may be omitted if the donor preparation is monomeric and supercoiled and if the donor molecules will not replicate in the host organism.

v. Target DNA Requirements

Plasmid targets for sequencing should be in circular form to facilitate recovery. Linear (e.g., chromosomal) DNA is an efficient substrate. A repair and ligation step is required before transformation, when using naturally transformable organisms. Large plasmids, such as cosmids and BACs, are usable targets. Target DNA must be at least 5 µg/ml in a no-salt buffer such as 1×TE. The concentration can be estimated by comparison of agarose gel band intensity with a DNA of known concentration or by absorbance at 260.

II. Exemplary Modifications

Once a site or region in a reporter protein is identified that is tolerant to modification, that site or region may be modified by deletion of one or more residues, insertion of one or more residues and/or by circular permutation or any combination thereof. In one embodiment, the modification may be the introduction of a recognition site for a hydrolase including but not limited to proteases, peptidases, esterases (e.g., cholesterol esterase), phosphatases (e.g., alkaline phosphatase) and the like. For instance, hydrolases include, but are not limited to, enzymes acting on peptide bonds (peptide hydrolases) such as aminopeptidases, dipeptidases, dipeptidyl-peptidases and tripeptidyl-peptidases, peptidyl-dipeptidases, serine-type carboxypeptidases, metallocarboxypeptidases, cysteine-type carboxypeptidases, omega peptidases, serine endopeptidases, cysteine endopeptidases, aspartic endopeptidases, metalloendopeptidases, threonine endopeptidases, and endopeptidases of unknown catalytic mechanism. For example, a modified beetle luciferase of the invention may comprise an enterokinase cleavage site, a caspase cleavage site, a coronavirus protease site (STLQ-SGLRKMA; SEQ ID NO:10), a kinase site, a HIV-1 protease site (SQNY-PIVQ or KAVRL-AEAMS; SEQ ID NO: 11 and SEQ ID NO:12, respectively), a HCV protease site (AEDVVCC-SMSYS; SEQ ID NO:13) (see, e.g., Lee et al., 2003), a SARS virus protease site (e.g., QTSITSAVLQSGFRKMAFPS; SEQ ID NO: 16, or VRQCSGVTFQGKFKKIVKGT; SEQ ID NO: 17), a rhinovirus protease site, e.g., rhinovirus 3C protease site, a prohormone convertase site, an interleukin-16-converting enzyme site, a CMV assembling site, a leishmandysin site, *B. anthracis* lethal factor, a botulinum neurotoxin light chain protease site, a β-secretase site for amyloid precursor protein (VKM-DAEF; SEQ ID NO: 14), prostate specific antigen sequence, a thrombin site, a renin and angiotensin-converting enzyme site, a cathepsin D site, a matrix metalloproteinase site, a uPA site, a plasmin site, a binding site for a cation, such as a calcium binding domain, a calmodulin binding domain, a cellulose binding domain, a chitin binding domain, a maltose binding protein domain, or a biotin binding domain. In another embodiment, a modified reporter protein of the invention may comprise a sequence recognized by a ligand such as an antibody or a metal such as calcium.

III. Exemplary Polynucleotides and Proteins

The invention includes a modified reporter protein encompassing any amino acid sequence which provides a polypeptide having a detectable activity, e.g., luminescent activity, as well as protein fragments thereof, which are recombinantly or synthetically synthesized. The reporter protein sequences of a modified reporter protein are the same or are substantially the same as the amino acid sequence of a corresponding unmodified reporter protein. A polypeptide or peptide having substantially the same sequence means that an amino acid sequence is largely, but may not entirely be, the same and retains a functional activity of the sequence to which it is related. In general, two amino acid sequences are substantially the same or substantially homologous if they are at least 70% identical, e.g., have at least 80%, 90%, 95% or more identity.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted by the local homology algorithm of Smith et al. (1981), by the homology alignment algorithm of Needleman et al. (1970), by the search for similarity method of Person et al. (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller (1988). The BLAST programs of Altschul et al. (1990), are based on the algorithm of Karlin and Altschul (1990).

Software for performing BLAST analyses is publicly available through the National Center for Biotechnology Information (see the URL at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990).

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See the URL at www.ncbi.nlm.nih.gov/.

In particular, a polypeptide may be substantially related but for a conservative variation. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

In one embodiment, a polynucleotide of the invention is optimized for expression in a particular host. As used herein, optimization includes codon optimization as well as, in eukaryotic cells, introduction of a Kozak sequence, and/or one or more introns. Thus, a nucleic acid molecule may have a codon composition that differs from that of a wild-type nucleic acid sequence encoding an unmodified beetle luciferase at more than 30%, 35%, 40% or more than 45%, e.g., 50%, 55%, 60% or more of the codons. Preferred codons for use in the invention are those which are employed more frequently than at least one other codon for the same amino acid in a particular organism and, more preferably, are also not low-usage codons in that organism and are not low-usage codons in the organism used to clone or screen for the expression of the nucleic acid molecule. Moreover, preferred codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In one embodiment of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In one embodiment of the invention, the majority of the codons which differ are ones that are preferred codons in a desired host cell. Preferred codons for mammals (e.g., humans) and plants are known to the art (e.g., Wada et al., 1990). For example, preferred human codons include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, preferred "humanized" synthetic nucleic acid molecules of the invention have a codon composition which differs from a wild type nucleic acid sequence by having an increased number of the preferred human codons, e.g. CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the nucleic acid molecule of the invention may have an increased number of CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof, relative to the wild-type nucleic acid sequence. Similarly, nucleic acid molecules having an increased number of codons that are employed more frequently in plants, have a codon composition which differs from a wild-type nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

The modified beetle luciferase proteins or fusion proteins of the invention may be prepared by recombinant methods or by solid phase chemical peptide synthesis methods. Such methods have been known in the art since the early 1960's (Merrifield, 1963) (See also Stewart et al., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of Geysen et al. (1984) and provide for synthesizing peptides upon the tips of a multitude of rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, e.g., inverting and inserting the rod's and pin tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

IV. Fusion Partners Useful with the Modified Reporter Protein of the Invention

The polynucleotide of the invention which encodes a modified reporter protein may be employed with other nucleic acid sequences, e.g., a native sequence such as a cDNA or one which has been manipulated in vitro, e.g., to prepare N-terminal, C-terminal, or N- and C-terminal fusion proteins, e.g., a fusion with a protein encoded by a different reporter gene including a selectable marker. Many examples of suitable fusion partners are known to the art and can be employed in the practice of the invention.

Fusion partners include but are not limited to affinity domains or other functional protein sequences, such as those having an enzymatic activity. For example, a functional protein sequence may encode a kinase catalytic domain (Hanks and Hunter, 1995), producing a fusion protein that can enzymatically add phosphate moieties to particular amino acids, or may encode a Src Homology 2 (SH2) domain (Sadowski et al., 1986; Mayer and Baltimore, 1993), producing a fusion protein that specifically binds to phosphorylated tyrosines.

Affinity domains are generally peptide sequences that can interact with a binding partner, e.g., such as one immobilized on a solid support. DNA sequences encoding multiple consecutive single amino acids, such as histidine, when fused to the expressed protein, may be used for one-step purification of the recombinant protein by high affinity binding to a resin column, such as nickel sepharose. Sequences encoding peptides, such as the chitin binding domain (which binds to chitin), glutathione-S-transferase (which binds to glutathione), biotin (which binds to avidin and strepavidin), and the like, can also be used for facilitating purification of the protein of interest. The affinity domain can be separated from the protein of interest by methods well known in the art, including the use of inteins (protein self-splicing elements (Chong et al., 1997). Exemplary affinity domains include HisV5 (HHHHH) (SEQ ID NO:1), HisX6 (HHHHHH) (SEQ ID NO:2), C-myc (EQKLISEEDL) (SEQ ID NO:3), Flag (DYKDDDDK) (SEQ ID NO:4), SteptTag (WSHPQFEK) (SEQ ID NO:5), hemagluttinin, e.g., HA Tag (YPYDVPDYA) (SEQ ID NO:6), GST, thioredoxin, cellulose binding domain, RYIRS (SEQ ID NO:104), Phe-His-His-Thr (SEQ ID NO:105), chitin binding domain, S-peptide, T7 peptide, SH2 domain, C-end RNA tag, WEAAAREACCRECCARA (SEQ ID NO:8), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin $D_{9K}$, calbindin $D_{28K}$, and calretinin, inteins, biotin, streptavidin, MyoD, Id, leucine zipper sequences, and maltose binding protein. In one embodiment, the fusion partner is a sequence useful to purify a fusion protein, e.g., a His or GST tag, and in one embodiment the purification tag is fused to the N- or C-terminus of a circularly permuted reporter protein.

Another class of fusion partners includes a protein encoded by a reporter gene, including, but are not limited to, a neo gene, a β-gal gene, a gus gene, a cat gene, a gpt gene, a hyg gene, a hisD gene, a ble gene, a mprt gene, a bar gene, a nitrilase gene, a galactopyranoside gene, a xylosidase gene, a thymidine kinase gene, an arabinosidase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xylE gene, an α-amylase gene, a tyrosinase gene, an anthozoan luciferase (luc) gene, (e.g., a *Renilla reniformis* luciferase gene), an aequorin gene, a red fluorescent protein gene, or a green fluorescent protein gene. Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA, and proteins that are inserted or trapped in the cell membrane.

V. Vectors and Host Cells Encoding the Modified Reporter Protein or Fusions Thereof Once a desirable nucleic acid molecule encoding a modified reporter protein or a fusion thereof is prepared, an expression cassette encoding the modified reporter protein or a fusion protein comprising the modified reporter protein is prepared. For example, a nucleic acid molecule comprising a nucleic acid sequence encoding a modified beetle luciferase is optionally operably linked to transcription regulatory sequences, e.g., one or more enhancers, a promoter, a transcription termination sequence or a combination thereof, to form an expression cassette. The nucleic acid molecule or expression cassette may be introduced to a vector, e.g., a plasmid or viral vector, which optionally includes a selectable marker gene, and the vector introduced to a cell of interest, for example, a prokaryotic cell such as *E. coli*, *Streptomyces* spp., *Bacillus* spp., *Staphylococcus* spp. and the like, as well as eukaryotic cells including a plant (dicot or monocot), fungus, yeast, e.g., *Pichia, Saccharomyces* or *Schizosaccharomyces*, or a mammalian cell. Preferred mammalian cells include bovine, caprine, ovine, canine, feline, non-human primate, e.g., simian, and human cells. Preferred mammalian cell lines include, but are not limited to, CHO, COS, 293, Hela, CV-1, SH-SY5Y, HEK293, and NIH3T3 cells.

The expression of an encoded modified reporter protein may be controlled by any promoter capable of expression in prokaryotic cells or eukaryotic cells. Preferred prokaryotic promoters include, but are not limited to, SP6, T7, T5, tac, bla, trp, gal, lac or maltose promoters. Preferred eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. The nucleic acid molecule, expression cassette and/or vector of the invention may be introduced to a cell by any method including, but not limited to, calcium-mediated transformation, electroporation, microinjection, lipofection and the like.

VI. Exemplary Uses

The modified reporter proteins or fusions thereof are useful for any purpose including, but not limited to, detecting the amount or presence of a particular molecule (a biosensor), isolating a particular molecule, detecting conformational changes in a particular molecule, e.g., due to binding, phosphorylation or ionization, detecting conditions; for instance, pH or temperature, facilitating high or low throughput screening, detecting protein-protein, protein-DNA or other protein-based interactions, or selecting or evolving biosensors. For instance, a modified reporter protein or a fusion thereof, is useful to detect e.g., in an in vitro or cell-based assay, the amount, presence or activity of a particular kinase (for example, by inserting a kinase site into a reporter protein), RNAi (e.g., by inserting a sequence suspected of being recognized by RNAi into a coding sequence for a reporter protein, then monitoring reporter activity after addition of RNAi), or protease, such as one to detect the presence of a particular viral protease, which in turn is indicator of the presence of the virus, or an antibody; to screen for inhibitors, e.g., protease inhibitors; to identify recognition sites or to detect substrate specificity, e.g., using a modified luciferase with a selected recognition sequence or a library of modified luciferases having a plurality of different sequences with a single molecule of interest or a plurality (for instance, a library) of molecules; to select or evolve biosensors or molecules of interest, e.g., proteases; or to detect protein-protein interactions via complementation or binding, e.g., in an in vitro or cell-based approach. In one embodiment, a modified beetle luciferase which includes an insertion is contacted with a random library or mutated library of molecules, and molecules identified which interact with the insertion. In another embodiment, a library of modified luciferases having a plurality insertions is contacted with a molecule, and modified luciferases which interact with the molecule identified.

The invention also provides methods to monitor the expression, location and/or trafficking of molecules in a cell, as well as to monitor changes in microenvironments within a cell, using a modified beetle luciferase or a fusion protein thereof. For example, in one embodiment, a modified beetle luciferase comprises an internal insertion containing two domains which interact with each other under certain conditions. In one embodiment, one domain in the insertion contains an amino acid which can be phosphorylated and the other domain is a phosphoamino acid binding domain. In the presence of the appropriate kinase or phosphatase, the two domains in the insertion interact and change the conformation of the modified beetle luciferase resulting in an alteration in the detectable activity of the modified beetle luciferase. In another embodiment, a modified beetle luciferase comprises a recognition site for a molecule, and when the molecule interacts with the recognition site, results in an increase in activity, and so can be employed to detect or determine the presence of amount or the other molecule.

Two-hybrid systems are extremely powerful methods for detecting protein:protein interactions in vivo as well as identifying residues/domains involved in protein:protein interactions. The basis of two-hybrid systems is the modular domains found in some transcription factors: a DNA-binding domain, which binds to a specific DNA sequence, and a transcriptional activation domain, which interacts with the basal transcriptional machinery (Sadowski, 1988). A transcriptional activation domain in association with a DNA-binding domain may promote the assembly of RNA polymerase II complexes at the TATA box and increase transcription. In the CheckMate™ Mammalian Two-Hybrid System (Promega Corp., Madison, Wis.), the DNA-binding domain and the transcriptional activation domain, produced by separate plasmids, are closely associated when one protein ("X") fused to a DNA-binding domain interacts with a second protein ("Y") fused to a transcriptional activation domain. In this system, interaction between proteins X and Y results in transcription of either a reporter gene or a selectable marker gene. In particular, the pBIND Vector contains a yeast GAL4 DNA-binding domain upstream of a multiple cloning region, and a pACT Vector contains the herpes simplex virus VP16 activation domain upstream of a multiple cloning region. In addition, the pBIND Vector expresses the *Renilla reniformis* luciferase. The two genes encoding the two potentially interactive proteins of interest are cloned into pBIND and pACT Vectors to generate fusion proteins with the DNA-binding domain of GAL4 and the activation domain of VP16, respectively. The pG5luc Vector contains five GAL4 binding sites upstream of a minimal TATA box, which in turn, is upstream of the firefly luciferase gene (luc+). The pGAL4 and pVP16 fusion constructs are transfected along with pG5luc Vector into mammalian cells. Two to three days after transfection the cells are lysed, and the amount of *Renilla* luciferase and firefly luciferase can be quantitated using the Dual-Luciferase® Reporter Assay System (Promega Cat. #E1910). Interaction between the two test proteins, as GAL4 and VP16 fusion constructs, results in an increase in firefly luciferase expression over the negative controls. A modified beetle luciferase of the invention, e.g., one which is deleted at a site or region which is tolerant to modification (a N-terminal fragment), is fused to a DNA binding domain while the remainder of the beetle luciferase (the C-terminal fragment) is fused to a transcriptional activator domain.

The invention also provides methods of screening for agents ("test" agents) capable of modulating the activity of a molecule of interest. "Modulation" refers to the capacity to either enhance or inhibit a functional property of biological activity or process (e.g., enzyme activity); such enhancement or inhibition may be contingent on the occurrence of a specific event, such as activation of a signal transduction pathway, and/or may be manifest only in particular cell types. A "modulator" refers to an agent (naturally occurring or non-naturally occurring), such as, for example, a biological macromolecule (e.g., nucleic acid, protein, non-peptide, or organic molecule), small molecules, or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in the screening assays described herein. The activities (or activity) of a modulator may be known, unknown or partially known. Such modulators can be screened using the methods of the invention. The term "test agent" refers to an agent to be tested by one or more screening method(s) of the invention as a putative modulator. Usually, various predetermined concentrations are used for screening such as 0.01 µM, 0.1 µM, 1.0 µM, and 10.0 µM. Controls can include the measurement of a signal in the absence of the test agent, comparison to an agent known to modulate the target, or comparison to a sample (e. a cell, tissue or organism) before, during and/or after contacting with the test agent.

In one embodiment, the method includes screening for agents that modulate protease activity. For example, in one embodiment, a method of identifying an agent capable of modulating apoptosis is provided. Caspase family proteases have been associated with apoptosis. Thus, the method includes contacting a sample suspected of containing a caspase-family protease with an agent suspected of modulating the caspase activity, and a modified reporter protein having a cleavage site cleavable by the caspase. The activity of the modified reporter protein is detected in the sample before and after contacting with the test agent. An increase in activity after contacting with the agent is indicative of an agent that inhibits apoptosis and a decrease is indicative of an agent that activates apoptosis.

Accordingly, the invention provides a screening system useful for identifying agents which modulate the cleavage of recognition sequence present in a modified reporter protein of the invention and detecting its activity. This allows one to rapidly screen for protease activity modulators. Utilization of the screening system described herein provides a sensitive and rapid means to identify agents which modulate (e.g., inhibit or activate) a protease, for example, a caspase family protease.

A modified reporter protein of the invention is thus useful as a substrate to study agents or conditions that modulate an interaction between an insertion in the modified reporter protein and a molecule of interest. In particular, the invention contemplates modified luciferase proteins in which the insertion includes an amino acid sequence that is a cleavage site for an enzyme of interest. Thus, when the molecule of interest is a protease, the insertion comprises a peptide containing a cleavage recognition sequence for the protease. A cleavage recognition sequence for a protease is a specific amino acid sequence recognized by the protease during proteolytic cleavage. Accordingly, the invention provides methods to determine the amount of a protease in a sample by contacting the sample with a modified luciferase polypeptide of the invention and measuring changes in luciferase activity. The modified luciferase protein of the invention can be used for, among other things, monitoring the activity of a protease inside a cell that expresses the modified luciferase.

The assays of the invention can be used to screen drugs to identify compounds that alter the activity of a protease that cleaves the modified reporter protein. In one embodiment, the assay is performed on a sample in vitro containing a protease. A sample containing a known amount of protease is mixed with a modified reporter protein of the invention and with a test agent. The amount of the protease activity in the sample is then determined as described above. Then the amount of activity per mole of protease in the presence of the test agent is compared with the activity per mole of protease in the absence of the test agent. A difference indicates that the test agent alters the activity of the protease. Accordingly, the alterations may be an increase in protease activity resulting in a decrease in modified reporter protein activity or a decrease in protease activity corresponding to an increase or maintenance of modified reporter protein activity.

In one embodiment, the ability of an agent to alter protease activity is determined. In this assay, cells are conditioned or contacted with an agent suspected of modulating protease activity. The cell or cells in the culture are lysed and protease activity measured. For example, a lysed cell sample containing a known or unknown amount of protease is mixed with a modified reporter protein of the invention. The amount of the protease activity in the sample is then determined as above by determining the degree of modified reporter protein activity in a control or non-treated sample and the treated lysed cellular sample. The activity or inhibition can be calculated based on a per microgram or milligram protein in the sample. Accordingly, the modulation in protease activity includes an increase in protease activity resulting in a decrease in modified reporter protein activity or a decrease in protease activity corresponding to an increase or maintenance of modified reporter protein activity. Typically, the difference is calibrated against standard measurements to yield an absolute amount of protease activity. A test agent that inhibits or blocks the activity or expression of the protease can be detected by increased modified reporter protein activity in treated cells compared to untreated controls.

In another embodiment, the ability of an agent to alter protease activity in vivo is determined. In an in vivo assay, cells transfected with an expression vector encoding a modified reporter protein of the invention are exposed to different amounts of the test agent, and the effect on reporter protein activity in a cell can be determined. Typically, the difference is calibrated against standard measurements to yield an absolute amount of protease activity. A test agent that inhibits or blocks the activity or expression of the protease can be detected by increased modified reporter protein activity in treated cells compared to untreated controls.

The materials and composition for use in the assay of the invention are ideally suited for the preparation of a kit. Such a kit may comprise a carrier means containing one or more container means such as vials, tubes, and the like, each of the container means comprising one of the separate elements to be used in the method. One of the containers comprises a modified reporter protein or polynucleotide (e.g., in the form of a vector) of the invention. A second container may contain a substrate for the modified reporter protein.

The invention will be further described by the following non-limiting examples.

EXAMPLE I

Tn5 Insertional Mutagenesis of a Click Beetle Luciferase Gene

A. Transposon Insertion Reaction
Target DNA Preparation

A click beetle luciferase gene (cbg69) was cloned into an *E. coli* T7 expression vector and the resulting plasmid (pJLC1) was used as target DNA for transposon mutagenesis reaction.

In Vitro Transposon Insertion Reaction

Reaction conditions were optimized to maximize the efficiency of the transposon insertion while minimizing multiple insertion events. For example, an equimolar amount of the transposon was added to the moles of target DNA.

1. Prepare the transposon insertion reaction mixture by adding in the following order:
   1 µl 100× reaction buffer
   0.35 µg target DNA (pJLC1) (7 µl)
   1 µl molar equivalent transposon
   1 µl transposase
   10 µl total reaction volume
2. Incubate the reaction mixture for 2 hours at 37° C.
3. Stop the reaction by adding 1 µl stop solution.

Mix and heat for 15 minutes at 65° C.

The reaction mixture was stored at −20° C.

B. Selection of Transposon Insertion Clones

Transformation and Recovery

The number of transposon insertion clones obtained per reaction depends on, among other factors, the transformation efficiency of the competent cells used. The greater the transformation efficiency of the competent cells, the greater the number of insertion clones obtained. A recA⁻ strain of *E. coli* (EC100 competent cells from Epicentre) was used for transformation.

3. Use 1 µl of the insertion reaction mixture, transform into EC100 electrocompetent cells.
4. Recover the electroporated cells by adding SOC medium to the electroporation cuvette to 1 ml final volume immediately after electroporation. Pipette the medium/cells gently to mix. Transfer to a tube and incubate on a 37° C. shaker for 30-60 minutes to facilitate cell outgrowth.
5. Plate portions of cells onto LB plates containing 50 µg/ml kanamycin.
6. Grow plates overnight at 37° C.

C. Transposon Insertion Mapping

Figure 2:
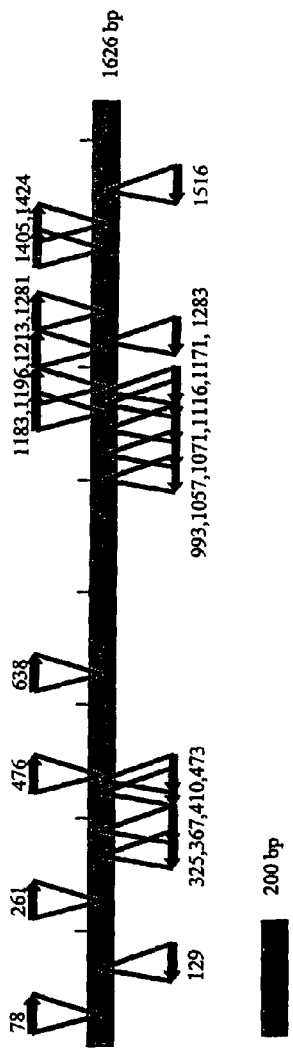
FIG. 2. Results for Tn5 insertion mutagenesis into the cbg69 gene. The protein encoded by cbg69 has one amino acid substitution at position 409 (I409V) relative to a wild-type click beetle luciferase (see FIG. 3).

Thousands of insertion colonies were obtained. Twenty-seven insertion clones were selected and the click beetle luc gene containing Tn5 transposon was PCR amplified using a primer set at the two termini of the cbg69 gene. The PCR products were sequenced using the same set of primer. The locations of the Tn5 insertion were shown to be random (FIGS. 2-3).

D. Generating a Plasmid Library of luc Gene with Transposon Insertions

Clones which had insertions in the luc gene need to be separated from the ones with insertions in the plasmid backbone. To do this, all transformants were pooled and plasmid DNA was purified. The resulting plasmid DNA was digested with a pair of restriction enzymes (e.g., NdeI and EcoRI) to release a DNA fragment containing the cbg69 gene with transposon insertions. This DNA fragment was recloned into the respective restriction enzyme sites of the *E. coli* T7-expression vector free of transposon insertions, yielding a plasmid library containing luc gene with Tn5 insertions.

E. Generating A Library of In Frame 19 Codon Insertions

Removal of Tn5 transposon

Once the plasmid library of luc gene with transposon insertions was generated, the Tn5 transposon was removed by digestion with a restriction enzyme, e.g., NotI. The linearized DNA was separated from the DNA fragment containing Tn5 by agarose gel electrophoresis and then purified.

Religation and Transformation

The linearized DNA was religated using T4 DNA ligase. Successful religation regenerated a single restriction site, e.g., NotI, and created the 57 nucleotide (19 codon) insertion into one of the three reading frames. The religated DNA was transformed into EC100 cells and recombinants were selected using an antibiotic marker present on the original cloning vector (e.g., ampicillin for the control DNA).

F. Screen for Active Linker Insertion Clones

Individual linker insertion clones were used to inoculate 1 ml of LB medium containing 100 µg/ml ampicillin and grown at 37° C. overnight. Luciferase activities were measured by mixing 100 µl of overnight culture with 100 µl Bright-Glo reagent from Promega Corp. (Madison, Wis.). Luminescence was recorded on a luminometer after 5 minutes.

G. DNA Sequencing of the active Linker Insertion Clones

Over 400 clones were screened. Linker insertion clones that had luciferase activities >20-fold above background were selected. The location of the linker insertion was determined by sequencing PCR products of the luc gene containing linker insertion. The positions and the relative activities of each active linker insertion clone are shown in FIGS. 3-4.

EXAMPLE II

Tn-7 Insertional Mutagenesis of a Firefly Luciferase Gene

A commercial kit (GPS™-M GPS-Mutagenesis System from New England Biolabs (NEB)) was used to insert a Tn7-based transposon randomly into firefly luciferase DNA. The major portion of this insert was then excised by restriction enzyme digestion and religation to yield a 5 amino acid insertion. Initially, colonies were grown and screened pre-excision for loss of luciferase activity. Plasmids in those cultures which had luciferase activity were then excised, transformed back into cells and colonies examined for a return of luciferase activity. Later, a more efficient approach was used where a gel-purified luciferase fragment containing the large insertion at random locations was cloned into a vector and mass-excision of the vector population was performed. Here, colonies were chosen which expressed luciferase activity following transformation with the excised vector. Because the transposon carried kanamycin resistance it was possible to eliminate vector molecules which did not contain insertions.

For the first approach, a reaction was assembled as follows:

2 µl 10×GPS buffer
1 µl 20 µg/ml pGPS5
1 µl 80 µg/ml pSP-Luc+
14 µl H₂0
20 µl pGPS5 (NEB), which carries a kanamycin resistance gene, was the donor plasmid, and pSP-Luc+(Promega Corp.), which has an ampicillin resistance gene, was the acceptor. Successful transposition resulted in the insertion of the kanamycin resistance cassette into the acceptor plasmid. The reaction was mixed by pipetting up and down and then 1 µl of TnsABC Transposase was added and the reaction remixed. The reaction was incubated for 1 hour at 37° C., heated for 10 minutes at 75° C., and then put on ice. 5 µl was then transformed into 100 µl high efficiency competent *E. coli* JM109 (Promega Corp.). Following a 10 minute incubation on ice, the cells were subjected to a 45 second 42° C. heat shock, followed by a 2 minute incubation on ice. 1 ml of Luria Broth (LB) was then added and the cells were shaken at 37° C. for 1 hour. 40 µl portions were then plated on LB agar plates containing 100 µg/ml ampicillin and 25 µg/ml kanamycin.

The next day colonies were picked from those plates and individually grown in 3 ml of LB/amp/kan+0.5 mM IPTG. After overnight growth, these cultures were assayed for luciferase activity by adding 10 µl of culture to 100 µl of 1 mM luciferin in 100 mM sodium citrate pH 5.5 and readings taken in a Turner 20/20 luminometer.

Plasmid was prepared from the low activity cultures (Promega Wizard Plus Minipreps kit), digested with restriction enzyme PmeI (NEB) to excise the majority of the insert, and then religated. Typically, these reactions were as follows:

1 µl miniprep DNA
1 µl 10 U/µl PmeI
2 µl 10× Buffer C (Promega)
16 µl H₂0
20 µl

Incubation was for 1 hour at 37° C. Reactions were then heated at 65° C. for 20 minutes to inactivate the restriction enzyme and the ligation reaction assembled as described below:
- 1 µl above reaction
- 3 µl 10× ligase buffer (Promega)
- 1 µl 3 U/µl T4 DNA ligase (Promega)
- 25 µl H$_2$0
- 30 µl Ligations were incubated at 16° C. for at least 2 hours and then 3 µl was transformed into JM109 as described above. 50 l of each transformation was plated on either LB/amp plates or on nitrocellulose filters overlayered on these plates. After overnight growth at 37° C., the filters were removed and placed on top of 1 ml of a solution of 1 mM luciferin in 100 mM sodium citrate pH 5.5 on a slide warmer (Fisher Scientific) set to 40° C. The room was darkened and the filters observed for luminescence. Colonies from picks observed to glow were grown up from the LB/amp plate, plasmid was isolated and then analyzed by restriction enzyme cutting and sequencing. Following excision of the large kanamycin insert, a single PmeI site remains at the site of insertion. Thus, cutting with PmeI and another restriction enzyme allows mapping of the site of insertion.

In a second approach, a library of insertions was isolated in a gel-purified luciferase fragment and cloned into a vector for excision and expression of the protein. Specifically, transposition into pSPLuc+ was accomplished as described above and then 3×5 µl was transformed into 3×100 µl high efficiency JM109 as described above. 40 µl from each tube was plated on LB/amp/kan and the cells from the remainder of this tube as well as the other tubes was added to 50 ml LB/amp/kan and grown overnight at 37° C. The plate yielded 93 colonies corresponding to a library of about 7,000 different plasmids, of which about 1,400 insertions were expected to be within the luciferase coding sequence. Plasmid was isolated from 8 ml of the liquid culture. Digestion of the plasmid with KpnI and EcoRI, which flank the luciferase gene, resulted in 4 fragments, corresponding to vector backbone and luciferase coding sequence, each either with or without the kanamycin insert. The band of interest was 3,438 bp in length and corresponded to the transposed luciferase gene fragment. About 2 µg of plasmid from the library was digested with KpnI and EcoRI and electrophoresed on a 1% agarose gel containing 1 µg/ml ethidium bromide. The 3,438 bp band was excised from the gel after visualization with UV illumination and purified from the agarose slice using Wizard PCR Preps (Promega Corp.). This DNA was then cloned into KpnI and EcoRI digested pGEM-3Z (Promega Corp.) following standard procedures. This places the luciferase gene under the control of the Lac promoter in the vector. The majority of the kanamycin insert was excised from the library by cutting with PmeI:
- 2 µl 0.25 µg/µl pGEM-3Z-luc-kan library
- 2 µl 10× Buffer C (Promega)
- 1.5 µl 10 U/µl PmeI (NEB)
- 14.5 µl H$_2$0
- 30 µl This reaction was incubated at 37° C. for 1 hour, then heated for 20 minutes at 65° C. and ligated as described below:
- 2 µl above digest
- 3 µl 10× ligase buffer (Promega)
- 1 µl 3 U/µl T4 DNA ligase (Promega)
- 24 µl H$_2$0
- 30 µl The ligation reaction was incubated at 16° C. overnight and then transformed into competent JM109 to obtain individual colonies. By plating on plates containing only ampicillin or both ampicillin+kanamycin it was possible to infer that approximately 90% of the transformants on ampicillin plates were sensitive to kanamycin and thus had successfully excised the insert. Individual colonies were cultured in 3 ml of LB+100 µg/ml ampicillin and the cultures assayed for luciferase activity.

Results

For the first approach, about 20% of the cultures had greatly reduced luciferase activity, which is consistent with the transposon being inserted into the luciferase coding region in the pSP-Luc+ plasmid. For the second approach, significant activity was observed in about 15% of the cultures from individual colonies. Plasmid was prepared from cultures with activity and restriction mapping performed to identify the approximate location of the PmeI site insert. These samples were then subjected to standard dideoxy sequencing at the University of Iowa DNA Sequencing Facility. About half of the active clones contained the insert just outside of the luciferase coding region. The remainder had the insert at various places within the coding region. The combined results from the two different methods discussed above are presented below with the position of the insertion and the approximate percent activity remaining indicated:

TABLE 1

| Inserted after Amino Acid | % Activity |
| --- | --- |
| 7 | 10 |
| 121 | 5-10 |
| 233 | 50-75 |
| 267 | 2 |
| 294 | 3 |
| 303 | 5-10 |
| 361 | 3-5 |
| 540 | 15 |
| 541 | 75 |

EXAMPLE III

Modified Click Beetle Luciferases with Modifications in the Hinge Region

In order to conveniently insert various sites of interest into the positions identified by transposon mutagenesis study, a click beetle luciferase gene (cbg69) was modified to generate two unique restriction enzyme sites, SnaBI (TACGTA) and SalI (GTCGAC), flanking the sequence encoding the hinge region. Specifically, two oligonucleotides: GGCTACG-TAAACAATGTGGAG (SEQ ID NO:9) and GCCACTAAA-GAAGCCCGTCGACGATGATGGCTGGCTC (SEQ ID NO: 18), were used to modify the cbg69 gene using Gene-Editor (Promega). The resulting click beetle luciferase, Cbg69ss, which has one amino acid substitution of Ile409 to Val, was shown to be twice as active as the wild-type Cbg69. The plasmid harboring cbg69ss (pJLC1ss) was used as a template to generate other luciferases with modifications in the hinge region. To that end, the following pairs of oligonucleotides were synthesized:

6His-a (SEQ ID NO: 31)
GTGAACCATCACCATCACCATCACAATGTGGAGGCCACTAAA

GAAGCCG

6His-b (SEQ ID NO: 32)
TCGACGGCTTCTTTAGTGGCCTCCACATTGTGATGGTGATGGT

GATGGTTCAC

FLAG-a (SEQ ID NO: 33)
GTGAACGACTATAAGGACGACGACGACAAGAATGTGGAGGC

CACTAAAGAAGCCG

FLAG-b (SEQ ID NO: 34)
TCGACGGCTTCTTTAGTGGCCTCCACATTCTTGTCGTCGTCGT

CCTTATAGTCGTTCAC

DEVD-a (SEQ ID NO: 35)
GTGAACGACGAGGTCGACAATGTGGAGGCCACTAAAGAAGC

CG

DEVD-b (SEQ ID NO: 36)
TCGACGGCTTCTTTAGTGGCCTCCACATTGTCGACCTCGTCGT

TCAC

Pka-a (SEQ ID NO: 37)
GTGAACCTGCGCCGCGCCTCCCTGGGTAATGTGGAGGCCACT

AAAGAAGCCG

Pka-b (SEQ ID NO: 38)
TCGACGGCTTCTTTAGTGGCCTCCACATTACCCAGGGAGGCG

CGGCGCAGGTTCAC

SARS3-a (SEQ ID NO: 39)
gtaaacACTTCTGCTGTTCTGCAGAGTGGTTTTcgcAATGTGGAGG

CCACTAAAGAAGCCg

SARS3-b (SEQ ID NO: 40)
tcgacGGCTTCTTTAGTGGCCTCCACATTgcgAAAACCACTCTGC

AGAACAGCAGAAGTgtttac

SARS6-a (SEQ ID NO: 41)
gtaaacTCTGGTGTTACCTTCCAAGGTAAGTTCAAGAATGTGGA

GGCCACTAAAGAAGCCg

SARS6-b (SEQ ID NO: 42)
tcgacGGCTTCTTTAGTGGCCTCCACATTCTTGAACTTACCTTGG

AAGGTAACACCAGAgtttac

Each oligonucleotide was phosphorylated using the following reaction conditions:

| Oligonucleotide | 30 pmol |
|---|---|
| 10x T4 polynucleotide kinase buffer | 2.5 µl |
| 10 mM ATP | 2.5 µl |
| T4 oligonucleotide kinase (1 µ/µl) | 0.5 µl |
| Water | to 25 µl |

Incubate at 37° C. for 30 minutes and inactivate at 70° C. for 10 minutes.

For each linker, a pair of phosphorylated oligonucleotides (10 µl from above reaction) were annealed by heating at 95° C. for 5 minutes and cooled down to 37° C. in 1 hour. Each linker was then cloned into the SnaBI and SalI sites of pJLC1ss.

Results

Figure 5A:
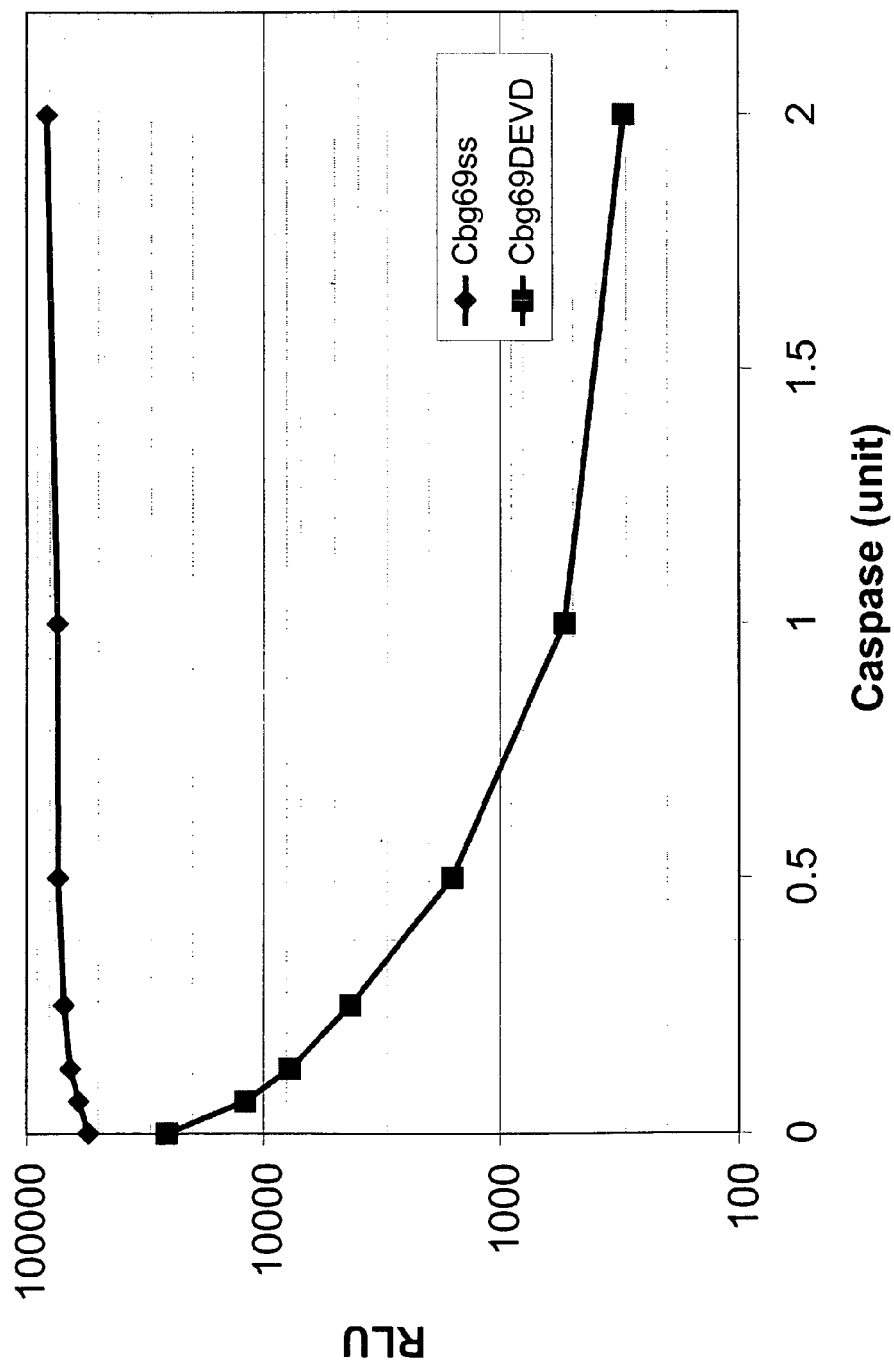
FIGS. 5A-C. Activity of a click beetle luciferase modified with a caspase-3 recognition site insertion (cbg69DEVD; DEVD is represented by SEQ ID NO:106). A) Relative light units (RLU) in a caspase assay with cbg69ss or cbg69DEVD (DEVD is represented by SEQ ID NO:106). B) RLU in a caspase assay with click beetle luciferases and a caspase inhibitor (Ac-DEVD-CHO; DEVD is represented by SEQ ID NO:106). C) RLU over time in an assay with varying amounts of caspase-3 and cbg69DEVD.
Figure 5B:
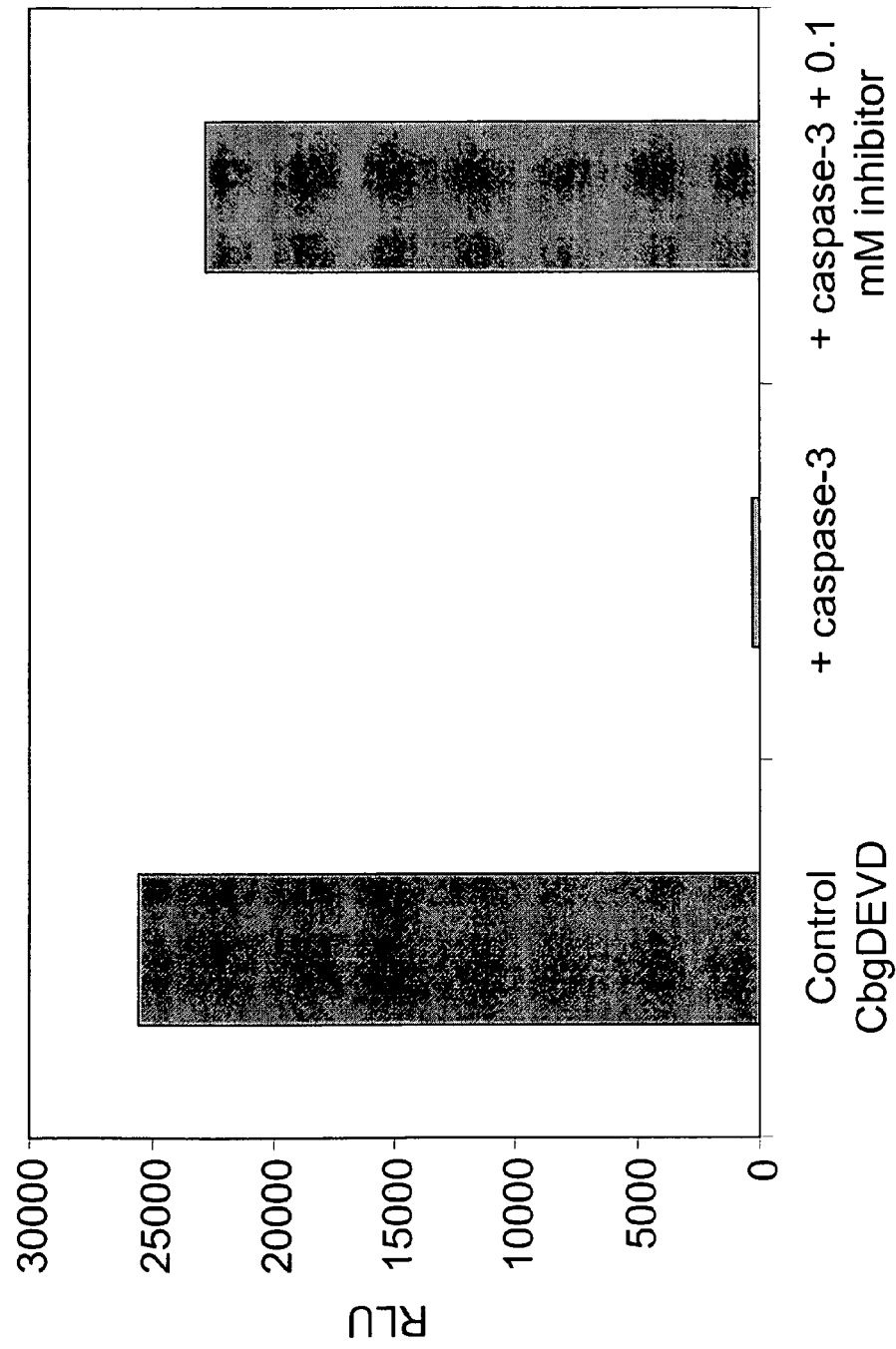
Figure 5C:
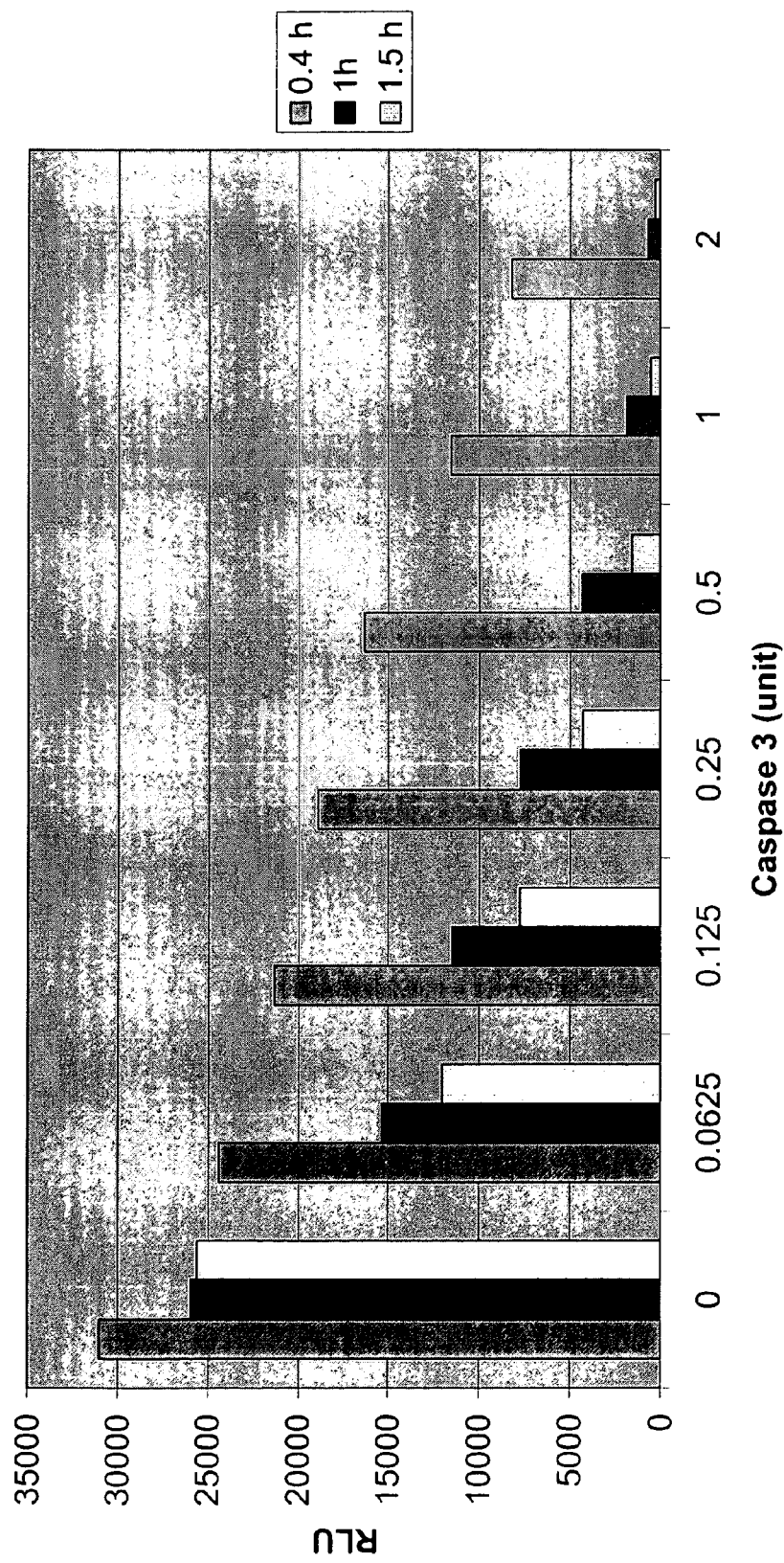

A. A click beetle luciferase was modified after residue 400 to contain a caspase-3 recognition site (DEVD; SEQ ID NO:106), yielding Cbg69DEVD (DEVD is represented by SEQ ID NO:106). Cbg69ss and Cbg69DEVD (DEVD is represented by SEQ ID NO:106) were expressed in a bacterial host. The bacterial lysates were mixed with varying amounts of caspase-3 (0, 6.25, 12.5, 25, 50, 100 or 200 ng) or 200 ng caspase-3 and 0.1 mM of a caspase inhibitor Ac-DEVD-CHO (DEVD is represented by SEQ ID NO:106) and luciferase activity monitored. FIG. 5A shows that as caspase-3 concentration increased, the activity of Cbg69DEVD (DEVD is represented by SEQ ID NO:106) but not that of Cbg69ss, decreased. Moreover, the decrease in activity was not observed when a caspase inhibitor was present (FIG. 5B). Further, the luciferase activity decreased over time (FIG. 5C).

B. SARS virus 3CL protease is a cysteine protease for SARS coronavirus, and is a potential target for an anti-SARS virus drug. Two click beetle luciferases were modified after residue 400 to contain one of two SARS protease recognition sites (Cbg69SARS3 and Cbg69SARS6). Cbg69ss, Cbg69SARS3 and Cbg69SARS6 were produced using in vitro translation systems such as a rabbit reticulocyte lysate and/or a wheat germ extract (Promega). The SARS protease was partially purified using a pMAL purification system from New England Biolabs. The lysates containing click beetle luciferase were mixed with SARS protease and luciferase activity monitored. FIG. 6C shows that after 1 hour of incubation at room temperature, Cbg69SARS, but not Cbg69ss, showed decreased activity when treated with SARS protease (about 0.3 µg) as compared to the untreated samples.

Figure 6B:
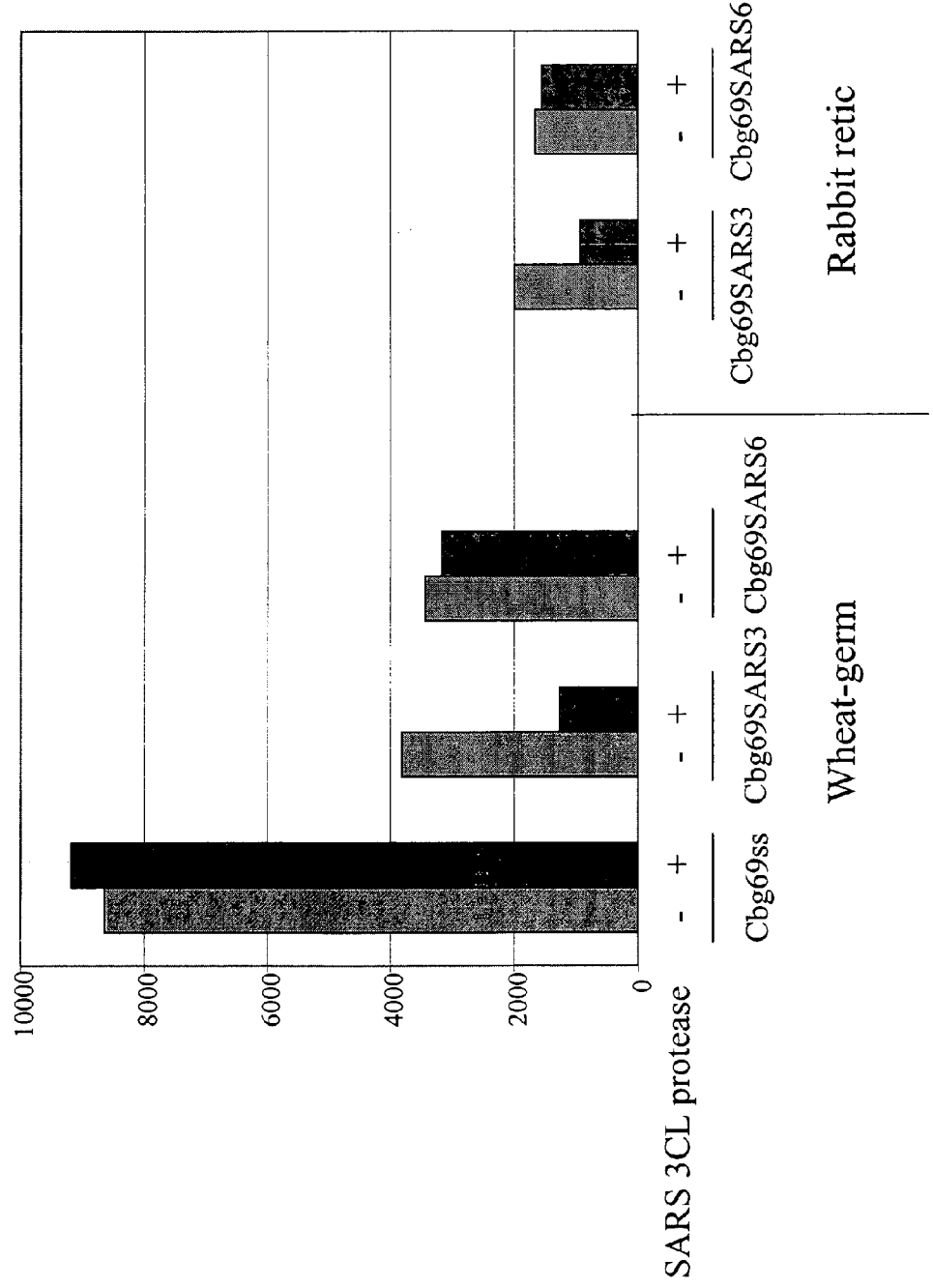
FIG. 6B. SARS virus 3CL protease activity in the presence of modified click beetle luciferases having SARS virus protease recognition sites.

C. Modified click beetle luciferases which have various insertions sites after Asn400 were all active, as shown in FIGS. 6A-C. These modified luciferases had activities ranging from 12-64% as compared to Cbg69ss. Thus, modifications in the hinge region of click beetle luciferase can yield a modified luciferase which retains activity.

EXAMPLE IV

A Modified Firefly Luciferase with an Internal Enterokinase Site

Since the 5 amino acid insertion after amino acids 233 and 541 of firefly luciferase retained the greatest fraction of enzyme activity (Example II), those sites were chosen for further analysis. The GeneEditor™ in vitro Site-Directed Mutagenesis System (Promega Corp.) was used to perform in vitro mutagenesis to insert protease cleavage sites at these sites in order to examine the effect on luciferase activity after cleavage with the protease. First, the luciferase gene was cloned into the expression vector pRSET-B (Invitrogen) between the NcoI and HindIII sites using standard techniques. The luc+ gene (encoding the protein sequence shown in FIG. 7A) was excised on a NcoI-EcoRV fragment from pSPLuc+ and cloned between the NcoI and HindIII in pRSET-B after filling in the HindIII site to create a blunt end. This construct fused luciferase amino acid sequence with an amino terminal 6×His tag.

To insert an enterokinase protease cleavage site (Asp(4) Lys) into pRSET-B-luc+ after Pro233 in luc+, an oligonucleotide of the sequence Pi-CCTATTTTTGGCAATCAAAT-CATTCCGGATGATGACGACAAGGATACTG CGATTTTAAGTGTTGTTCC (SEQ ID NO:1) was used. The plasmid template was first denatured as described below:

2 µl 1 mg/ml pRSET-B-luc+
2 µl 2M NaOH, 2 mM EDTA
16 µl H$_2$0
20 µl

This mixture was incubated for 5 minutes at room temperature, then 2 µl 2 M ammonium acetate and 75 µl 95% ethanol was added, and the resulting mixture incubated at −20° C. for 30 minutes. The mixture was then centrifuged in a microcentrifuge at top speed for 5 minutes at 4° C. The pellet was then washed with 150 µl-20° C. 70% ethanol, subjected to centrifugation for 2 minutes, vacuum dried and dissolved in 100 µl TE. The mutagenic oligonucleotide was annealed to the denatured template in the following reaction:

10 µl denatured template (above)
1 µl 2.9 ng/µl top strand selection oligonucleotide (0.25 pmole)
1 µl 28 ng/µl above mutagenic oligonucleotide (1.25 pmole)
2 µl annealing 10× buffer
6 µl H$_2$0
20 µl This annealing reaction was put in a beaker containing 200 ml of water at 75° C. then allowed to cool in the water to 37° C. Then the following components were added:

5 µl H$_2$0
3 µl 10× synthesis buffer
1 µl 7.7 U/µl T4 DNA polymerase
1 µl 3 U/µl T4 DNA ligase
30 µl This reaction was incubated at 37° C. for 90 minutes after which 5 µl of the reaction was transformed into competent BMH 71-18 mutS as described in the GeneEditor™ Technical Manual. The next day plasmid was prepared from the resulting culture and retransformed into JM109. The resulting individual colonies were picked, grown up, and plasmid prepared. Screening for mutants was accomplished by digesting the plasmids with BanII and SphI and electrophoresing the products on a 6% polyacrylamide gel (Novex, Invitrogen) which was stained with ethidium bromide. The digest produces a 361 bp fragment in the case of a wild-type gene (WT) and a 376 bp fragment for the insertion mutants containing the enterokinase site. Mutants identified in this fashion were then confirmed by sequencing. In this experiment, 7/8 clones contained the desired insertion.

Plasmids encoding either the WT luc+ gene or the enterokinase site insertion were transformed into BL21(DE3) pLysS (Novagen). Transformed cultures were grown at 37° C. to an A$_{600}$ of about 0.5 and then induced with IPTG at 1 mM and growth continued at 37° C. for an additional 3-4 hours. Cells were then pelleted and enzyme purified using MagneHis resin (Promega Corp.). Typically, 2 ml of cells were pelleted by centrifugation for 2 minutes in a microcentrifuge. The pellet was resuspended in 100 µl of MagneHis Wash/Binding buffer and then 10 µl of 10×MLR (product #V583A) was added to lyse the cells. 5 µl of 1 U/µl RQI DNase (Promega Corp.) and 3 µl of 7 U/µl RNase One (Promega Corp.) were added to the lysed cells and following a 10 minute incubation on ice with occasional mixing, the lysate was spun for 5 minutes in a microcentrifuge at 4° C. 40 µl of MagneHis resin was added to the supernatant and the resulting mixture incubated for 5 minutes at room temperature with occasional mixing. The resin was then concentrated on the tube wall by application of a magnet and washed through three cycles of resuspension and magnetization in MagneHis Wash/Binding buffer. The protein was finally eluted with 100 µl of 500 mM imidazole in 100 mM HEPES pH 7.5. This procedure yielded about 5 µg of either WT or modified proteins.

Although the modified protein incorporated the enterokinase site, the corresponding protease had no effect on enzyme activity and did not cut the mutant protein after Pro233. Both WT and mutant proteins also contained another enterokinase site at the amino terminus which permits removal of the 6×His tag from the protein. Gel analysis indicated that this site was utilized by enterokinase in both proteins.

Another modified protein was prepared which had a Gly (3)Asp(4)LysGly(3) (SEQ ID NO:112) site inserted after Pro233 which potentially makes the enterokinase site more accessible. The mutagenesis was performed as above utilizing a mutagenic oligonucleotide having the sequence

```
                                                    (SEQ ID NO: 2)
Pi-CCTATTTTTGGCAATCAAATCATTCCGGGTGGCGGTGATGATGACG

ACAAGGGTGGCGGTGATACTGCGATTTTAAGTGTTGTTCC.
```

Digestion reactions were assembled as follows:

| 1 | 2 | 3 | 4 |
|---|---|---|---|
| 10 µl 10X EKMax | 10 µl 10X EKMax | 10 µl 10X EKMax | 10 µl 10X EKMax |
| 2 µl WT Enzyme | 2 µl WT Enzyme | 1 µl Mutant Enzyme | 1 µl Mutant Enzyme |
| — | 1 µl 1 U/µl EKMax | — | 1 µl 1 U/µl EKMax |
| 83 µl H$_2$0 | 82 µl H$_2$0 | 83 µl H$_2$0 | 82 µl H$_2$0 |
| 100 µl | 100 µl | 100 µl | 100 µl |

Enterokinase (EKMax) and its 10× Buffer were from Invitrogen. Reactions were incubated at room temperature and at 15 and 30 minutes, 1 µl of the reaction was added to 100 µl of Luciferase Assay Reagent (Promega Corp.). Each sample was then read in a Turner 20/20 luminometer.

This yielded the following data:

|  | 1 | 2 | 3 | 4 |
|---|---|---|---|---|
| 0 minutes | 2517 | 2561 | 4090 | 3914 |
| 15 minutes | 2855 | 2905 | 3460 | 6108 |
| 30 minutes | 2987 | 3190 | 3301 | 5717 |

Figure 7B:
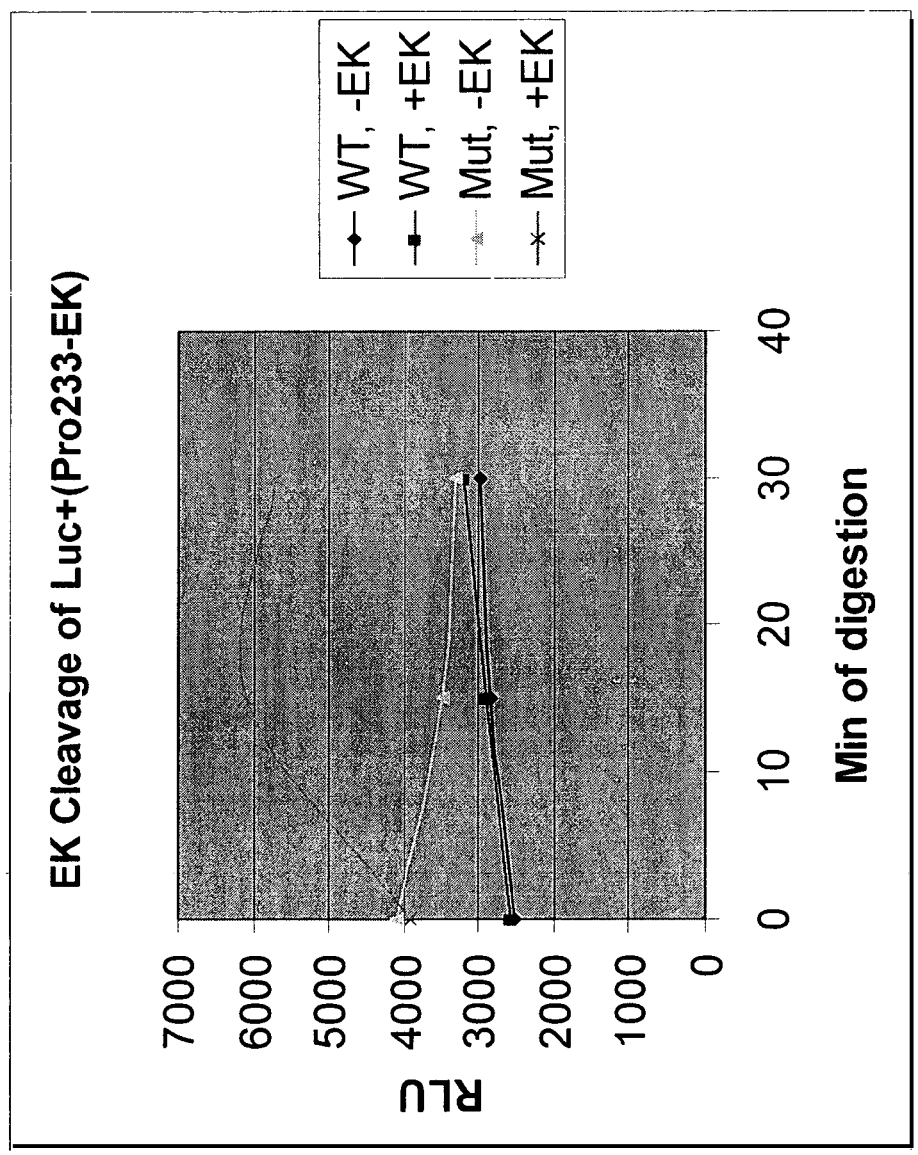

When the modified protein with the Gly(3)Asp(4)LysGly(3) (SEQ ID NO:112) site was treated with enterokinase, luciferase activity was found to increase by 50-100% (FIG. 7B). In contrast, enterokinase had no effect on the activity of the WT enzyme. Thus, nicking of the modified luciferase backbone did not destroy enzymatic activity. Moreover, the amino acid sequence of the insert may cause a stress on the modified protein which is relieved by nicking with the protease, resulting in an increase in the activity of the enzyme.

A larger insert containing an enterokinase site, i.e., Pro-GlyProGly(3)Asp(4)LysGly(3)ProGlyPro (SEQ ID NO:113), was inserted after Pro233 in Luc+. ProGlyPro was included to further increase the torsional stress on the protein. The oligonucleotide used to create this insertion was Pi-CCTATTTTTGGCAATCAAATCATTCCGC-CTGGCCCGGTGGCGGTGATGATGACGACAAGG GTGGCGGTCCTGGCCCGGATACTGC-GATTTTAAGTGTTGTTCC (SEQ ID NO:3). The mutagenesis was performed as above using pRSET-B-Luc+ as the starting plasmid. In this case, the resulting mutant plasmid was translated in vitro in a rabbit reticulocyte (Promega TnT® Coupled Reticulocyte Lysate System) in reactions such as those below:

| 1 | 2 |
|---|---|
| 25 µl TnT lysate | 25 µl TnT lysate |
| 2 µl TnT reaction buffer | 2 µl TnT reaction buffer |
| 1 µl T7 RNA Polymerase | 1 µl T7 RNA Polymerase |
| 1 µl amino acid mix | 1 µl amino acid mix |
| 1 µl 40 U/µl rRNasin | 1 µl 40 U/µl rRNasin |
| 1 µl WT plasmid | 1 µl Mutant plasmid |
| 19 µl H₂0 | 19 µl H₂0 |
| 50 µl | 50 µl |

Reactions were incubated for 1 hour at 30° C. and then treated with enterokinase (EKMax, Invitrogen) as below:

| 1 | 2 | 3 | 4 |
|---|---|---|---|
| 2 µl 10 X EKMax | 2 µl 10 X EKMax | 2 µl 10 X EKMax | 2 µl 10 X EKMax |
| 1 µl rxn 1 | 1 µl rxn 1 | 1 µl rxn 2 | 1 µl rxn 2 |
| — | 1 µl 1 U/µl EKMax | — | 1 µl EKMax |
| 17 µl H₂0 | 16 µl H₂0 | 17 µl H₂0 | 16 µl H₂0 |
| 20 µl | 20 µl | 20 µl | 20 µl |

Figure 7C:
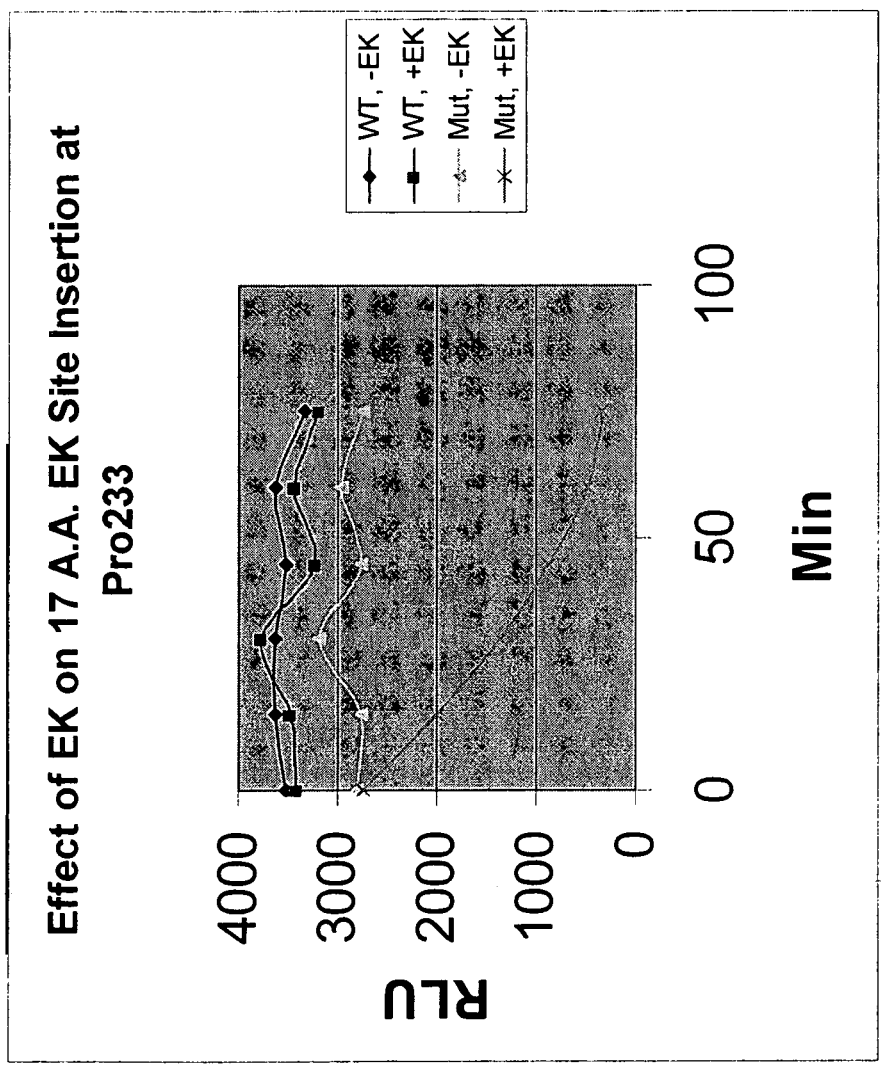

1 µl was assayed in 100 µl Luciferase Assay Reagent (LAR) prior to adding the enterokinase, then at various times at room temperature after protease addition. The resulting data is shown in FIG. 7C. The activity of the WT enzyme was not affected by the protease whereas the modified enzyme was inactivated by treatment with the protease.

Figure 7D:
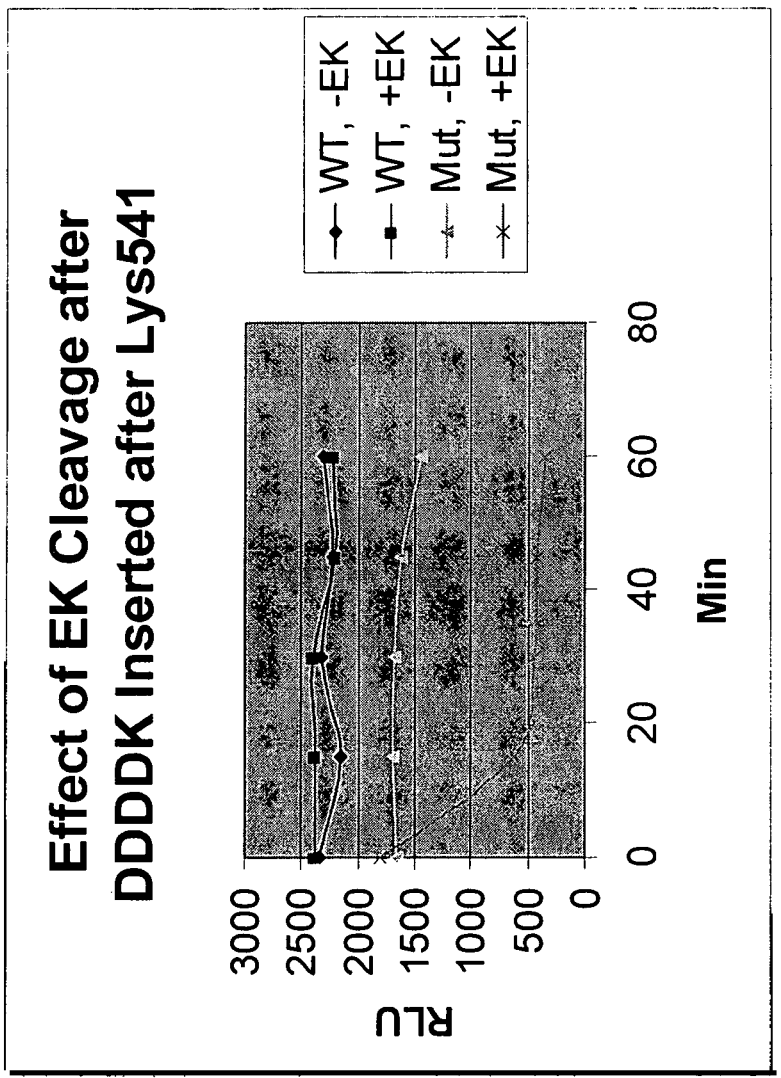

The effect of an enterokinase site insertion after Lys541 in Luc+ was also determined. In this case the oligonucleotide Pi-GCAAGAAAAATCAGAGAGATCCTCAT-AAAGGATGATGACGACAAGGCC AAGAAGGGCG-GAAAGATCGC (SEQ ID NO:4) was used with the pRSET-B-luc+ plasmid and the GeneEditor kit as described above to introduce the enterokinase site after Lys541, which is the ninth amino acid from the carboxyl end. The mutant plasmid, along with the WT as a control, was transcribed and translated in reactions similar to those described above, and then digested with enterokinase (FIG. 7D). Treatment of the modified enzyme with enterokinase reduced its activity by about 75% while the activity of the WT enzyme was not altered.

EXAMPLE V

A Modified Firefly Luciferase with a Deletion and Heterologous Insertion

To prepare a luciferase zymogen useful in in vitro or in vivo protease assays and in monitoring cellular events that are caused by or dependent on specific proteolysis, e.g., apoptosis, a firefly luciferase mutant was constructed which had 9 amino acids inserted after Lys541 (out of 550 amino acids). The 9 amino acids encoded a 5 residue enterokinase protease site followed by two glycines, and then 2 amino acids encoding an EcoRV site for cloning (DDDDKGGDI; SEQ ID NO:58). The vector also had an EcoRI site outside the 3' end of the gene which was used as a cloning site. When the protein specified by this base construct was cut with enterokinase, the carboxy terminal 9 amino acids were removed, generating an enzyme which had about 10% the activity of the WT enzyme. A library of EcoRV and EcoRI fragments of *E. coli* DNA was cloned between these sites in the base vector. 100 colonies were picked and assayed for luciferase activity. 7 colonies were found to have activity that was reduced by 100-1000 fold relative to WT. The 7 colonies were cultured and plasmid prepared. The plasmids were each found to contain an insert of *E. coli* DNA ranging in size from about 0.2 to 3 kb. These plasmids were translated in a TNT rabbit reticulocyte lysate and found to encode luciferases of higher molecular weight. Enterokinase cleavage of one of the proteins was found to increase luciferase activity by up to 40-fold. The modified protein showing the greatest activation had a molecular weight of about 68 kD, indication that about 60 residues had been appended to luciferase to generate the zymogen.

EXAMPLE VI

A Modified Firefly Luciferase which is Circularly Permuted

Plainkum et al. (2003) reported that circularly permuted forms of ribonuclease A having new N- and C-termini and a peptide linker containing a protease recognition site linking the original N- and C-termini had reduced ribonuclease activity due to steric occlusion of the active site. Plainkum et al. found that cleavage of the circularly permuted ribonuclease A with the protease increased the activity of the protein, presumably by removing the block to the active site.

In the case of luciferase, the N- and C-termini are separated by about 40 angstroms, a distance equivalent to 5-6 amino acids. The linking the N- and C-termini of luciferase with a peptide tether may disrupt its activity by preventing the closure of the "lid" domain formed by the carboxyl terminal domain of the protein. Thus, a head to tail dimer of the firefly luciferase luc+ gene was constructed. PCR primers were designed so that the upstream primer amplified beginning at Asp(234) and the downstream primer amplified beginning at Pro(233). The upstream primer contained an ATG codon for a methionine just prior to Asp(234), and the downstream primer contained a stop codon. In vitro mutagenesis was used to remove the stop codon between the original C- and N-termini, linking these termini with a sequence encoding a protease recognition site. For purposes of cloning the resulting PCR product, both the upstream and downstream primers also encoded a restriction enzyme site.

Methods

The head to tail luc+ dimer was constructed as follows. The vector pSPLuc+ (Promega Corp.) was digested with NcoI, the ends filled using T4 DNA polymerase, and the blunt end linearized vector digested with EcoRI. To serve as the accepting vehicle, pSPLuc+ was digested with XbaI, the ends filled using T4 DNA polymerase, then digested with EcoRI. The luciferase fragment from the first digest was cloned into this vector, resulting in a head to tail arrangement of two luc+ genes in the same vector. Specifically, pSPLuc+ was digested in a reaction as follows:

1 µl 1 mg/ml pSPLuc+
5 µl 10× Buffer D (Promega)
2 µl 10 U/µl NcoI
42 µl H$_2$0
50 µl The reaction was incubated for 1 hour at 37° C., heated 15 minutes at 65° C., and then chilled briefly on ice. Then 5 µl 10 mM dNTP and 1 µl 9 U/µl T4 DNA polymerase (Promega Corp.) were added and the reaction incubated for 20 minutes at 37° C. The reaction was purified using a Wizard Clean-Up kit (Promega Corp.). Following elution at 65° C. in 50 µl from the Clean-Up resin, the mixture was cooled, and the DNA was digested by adding 5 µl 10× Buffer H (Promega Corp.) and 1 µl 12 U/µl EcoRI (Promega Corp.). The reaction was incubated for 1 hour at 37° C. and then heated at 65° C. for 15 minutes. The accepting vector was then prepared as follows:

1 µl 1 mg/ml pSPLuc+
5 µl 10× Buffer D
1.5 µl 10 U/µl XbaI
42.5 µl H$_2$0
50 µl

The above reaction was incubated at 37° C. for 1 hour then purified using the Promega Wizard Clean-Up Kit with elution in 50 µl at 65° C. The following was added to the purified DNA:

5 µl 10× Buffer C (Promega Corp.)
5 µl 10 mM dNTP
1 µl 9 U/µl T4 DNA Polymerase

The reaction was incubated for 20 minutes at 37° C. and then purified as described above. 5 µl 10× Buffer H and 1 µl 12 U/µl EcoRI was added to the eluate from the Clean-Up Resin. The reaction was incubated for 1 hour at 37° C. and then heated at 65° C. for 15 minutes to inactivate the restriction enzyme. This DNA was then mixed with the above digested DNA as below:

15 µl XbaI cut, filled EcoRI cut, heated pSPLuc+
25 µl NcoI cut, filled, EcoRI cut, heated pSPLuc+
5 µl 10× ligase buffer (Promega Corp.)
2 µl 3 U/µl T4 DNA ligase After ligation overnight at 16° C., 1 µl was transformed into high efficiency competent *E. coli* JM109 (Promega Corp.) and the cells plated on LB/amp plates. Transformants were identified which contained the correct sized plasmid. Those transformants were expanded, plasmid isolated therefrom and the identity of the plasmid confirmed by restriction enzyme digestion.

The head to tail dimer Luc+ DNA constructed above was used as a template for the PCR amplification of a permuted luciferase with a new N-terminus at Asp(234) and a new C-terminus at Pro(233). The primers used in this amplification had the sequence:

```
Upstream primer =
                                  (SEQ ID NO: 109)
AGCTACATATGGATACTGCGATTTTAAGTGTTGTTC Downstream primer =
                                  (SEQ ID NO: 110)
AGCTAGGATCCTTACGGAATGATTTGATTGCCAAAAATAG
```

The amplification reaction was as follows:
5 µl 10×PfuUltra buffer (Stratagene)
1 µl 10 mM dNTP
1 µl 5 ng/µl above Luc+ dimer construct DNA
1 µl 100 ng/µl upstream primer
1 µl 100 ng/µl downstream primer
40 µl H$_2$0
49 µl The reaction was mixed, overlayed with mineral oil and placed into a PE480 thermal cycler at 95° C. After 2 minutes at this temperature, 1 µl of 2.5 U/µl PfuUltra DNA polymerase (Stratagene) was added and 20 cycles of 95° C. 30 seconds, 50° C. 30 seconds, 72° C. 1 minute were performed, after which the block was brought to 4° C. The completed reaction was then purified using Promega's Wizard PCR Preps kit and subsequent elution from the Wizard resin in 501 of H$_2$0. The PCR primers incorporated into the product have a site for NdeI (upstream primer) or BamHI (downstream primer). The PCR product was digested with these enzymes and cloned into the T7 expression vector pET-3a (Novagen) as below:

| 1 | 2 |
| --- | --- |
| 5 µl 10 X Buffer D (Promega) | 5 µl 10 X Buffer D (Promega) |
| 20 µl above PCR | 1 µl 0.38 µg/µl pET-3a |
| 1 µl 10 U/µl NdeI | 1 µl 10 U/µl NdeI |
| 1 µl 10 U/µl BamHI | 1 µl 10 U/µl BamHI |
| 23 µl H$_2$O | 42 µl H$_2$O |
| 50 µl | 50 µl |

The above reactions were incubated at 37° C. for 1 hour, then each was purified using the Promega Wizard Clean Up kit and DNA eluted in 50 µl of TE at 65° C. The two purified DNAs were mixed and ligated as below:

5 µl 10× ligase buffer
20 µl eluted 1
10 µl eluted 2
2 µl 3 U/µl T4 DNA ligase
13 µl H$_2$0
50 µl The ligation reaction was incubated at 16° C. for 2 hours, then 5 µl was transformed into competent JM109 and the cells plated on LB/amp. Colonies containing the appropriately sized plasmid were expanded, plasmid prepared and each preparation checked for the correct insertion by restriction digestion. Plasmid was found containing the insertion of the PCR product and this was used as the base vector for an in vitro mutagenesis which eliminated the stop codon and linked the C- and N-termini at the junction separating the two pieces of the luciferase gene.

The initial mutagenesis was performed using the Gene Editor kit from Promega Corp. utilizing a mutagenic oligonucleotide containing a recognition site for the protease enterokinase which cleaves on the carboxyl terminal side of Asp (4)Lys. This oligonucleotide had the sequence:

```
                                            (SEQ ID NO: 7)
Pi-GAAGGGCGGAAAGATCGCCGTGGATGATGACGACAAGATGGAAGAC
GCCAAAAACATAAAG
```

Six colonies from the second transformation round in the mutagenesis procedure were grown up individually and plasmid prepared therefrom. These plasmids were screened for having incorporated the mutagenic oligonucleotide by coupled transcription/translation in a TnT rabbit reticulocyte lysate (Promega Corp.). The correct mutants have fused the C- and N-termini of the luciferase domains and produce a full length luciferase protein. Translation reactions were performed as follows:

25 µl TnT Rabbit reticulocyte lysate
2 µl TnT reaction buffer
1 µl T7 RNA polymerase
1 µl complete amino acid mix
1 µl Fluorotect Lys tRNA
1 µl 40 U/µl rRNasin
5 µl mini prep DNA
14 µl
50 µl The translation reactions were incubated for 60 minutes at 30° C. and then treated (or not) with enterokinase (EK) (EK-Max, Invitrogen) as below:

2 µl 10×EKMax buffer
5 µl above translation reactions
+/−1 µl U/µl EKMax
12 µl H₂0
20 µl These digestions were performed at room temperature for 30 minutes then 1 µl was assayed by addition to 100 µl luciferase assay reagent (Promega Corp.). Data collection was performed in a Turner 20/20 luminometer. 5 µl of 4×SDS sample buffer was added to the remainder of each reaction and the samples heated for 2 minutes at 65° C. The samples were then electrophoresed on a 4-20% Novex Tris-glycine gel and the gel scanned at high sensitivity in Molecular Dynamics FluorImager. The results indicated that the fused full-length protein was made in two of the six clones, indicating that the mutagenesis was successful. Moreover, the activity of the fused mutant proteins was increased about 150-fold by treatment with enterokinase. Furthermore, the gel showed that the protease digested the full length protein into its pieces.

To examine the effect of EK treatment on the activity of mutant luciferases which had not been labeled by incorporation of the fluorescent lysine derivatives, translation reactions were performed as above but the Fluorotect Lys tRNA was omitted from the reactions. In this case, about a 90-fold activation of luciferase activity was observed when the enzyme was treated with EK (FIG. 7). Following activation, the mutant enzyme regained about 0.5% of the WT activity.

Another mutagenesis was performed to insert a caspase-3 DEVD cleavage site between the two luciferase domains. The Promega Gene Editor kit was used with the following mutagenic oligonucleotide:

```
                                            (SEQ ID NO: 111)
Pi-GAAGGGCGGAAAGATCGCCGTGGACGAAGTTGACGGTATGGAAGAC
GCCAAAAACATAAAG
```

In this case the desired mutant was found in 5/8 clones, and screened by in vitro transcription/translation. It was found that the fold activation by caspase-3 was higher than the fold activation previously observed for enterokinase. Also, the percent of activity restored by cleavage was also greater.

Figure 9:
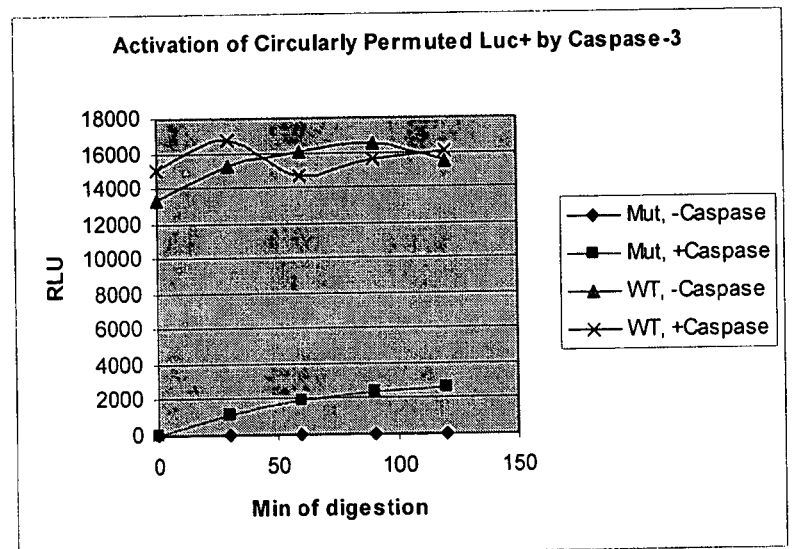
FIG. 9. Caspase-3 activation over time by a circularly permuted firefly luciferase having a caspase-3 site.
Figure 10A:
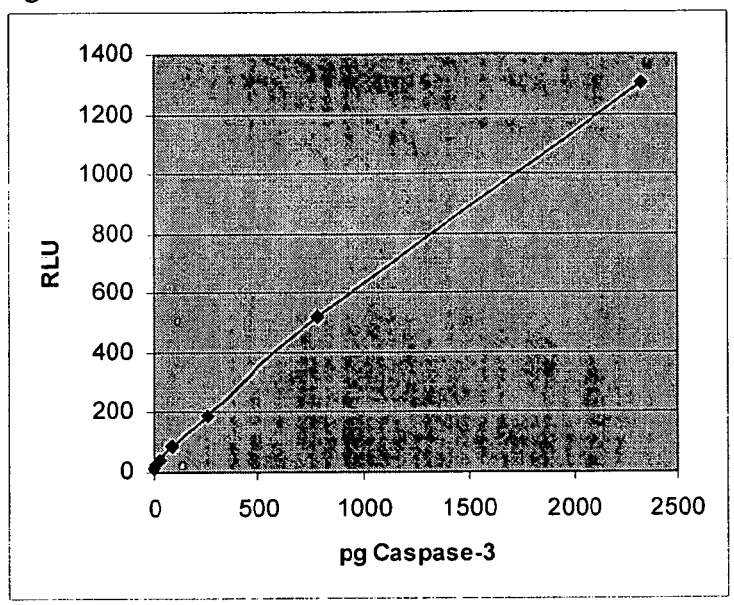
FIG. 10A. RLU in a caspase assay with various amounts of caspase-3 and a circularly permuted firefly luciferase having a caspase-3 recognition site.
Figure 10B:
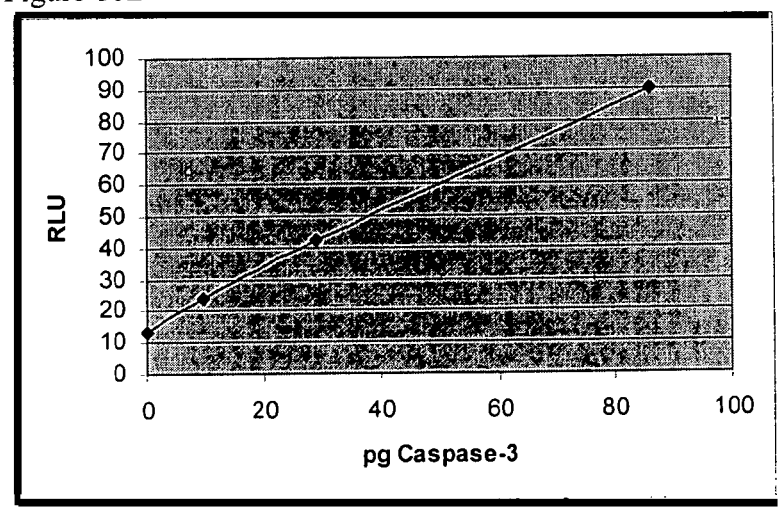
FIG. 10B. RLU in a caspase assay with various amounts of caspase-3 and a circularly permuted firefly luciferase having a caspase-3 recognition site.

In vitro translations were done in Promega TnT rabbit reticulocyte lysate in reactions containing either plasmid encoding permuted luciferase containing a caspase-3 DEVD cleavage site or WT luciferase. Portions of these reactions were then digested with caspase-3 (100 units, BioMol) to generate the data shown in FIGS. 9-11). The activity of the WT enzyme was not affected by the protease. In contrast, the activity of the mutant enzyme was greatly increased by treatment with caspase-3. The fold activation in this case was about 500-fold and the activated enzyme had about 17% the activity of the WT.

The ability of the permuted enzyme to detect caspase-3 activity was also examined in luminescent protease assays. Caspase reactions were performed in:

10 µl 2× Caspase buffer
5 µl in vitro translated proteins
1 µl diluted caspase-3
4 µl H₂0
20 µl Reactions contained from between 9.6 to 2333 pg of caspase-3 and were incubated at room temperature for 90 minutes then 1 µl was removed and added to 100 µl luciferase assay reagent for reading in a Turner 20/20 luminometer. FIG. 9A shows the data obtained. Replotting the lower protease amount points (FIG. 9B) shows that the assay is capable of detecting low picogram amounts of caspase-3. Moreover, increasing the time of incubation from 90 minutes to overnight increased the sensitivity of the assay by an additional 4-fold (data not shown).

The synthesis and activation of the permuted luciferases was also examined in TnT Wheat Germ extracts (Promega Corp.). Reactions contained the following:

25 µl TnT T7 WG extract
2 µl TnT reaction buffer
1 µl T7 RNA polymerase
1 µl amino acid mix
1 µl 40 U/µl rRNasin
5 µl 50 ng/µl luciferase plasmids
15 µl H₂0
50 µl Reactions were incubated at 30° C. for 90 minutes then digested with proteases as below:

10 µl 2× buffer (100 mM HEPES pH 7.5, 200 mM NaCl, 0.2% CHAPS, 2 mM EDTA, 20% glycerol, 20 mM DTT)
10 µl in vitro translation reactions
1 µl U/µl EKMax or 1 µl 100 U/µl Caspase-3

Figure 8:
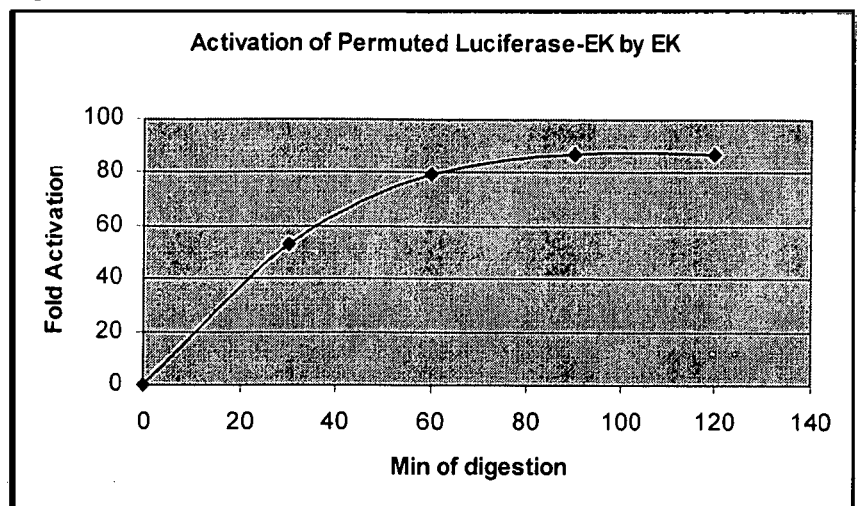
FIG. 8. Enterokinase activation of a circularly permuted firefly luciferase having an enterokinase site.
Figure 11:
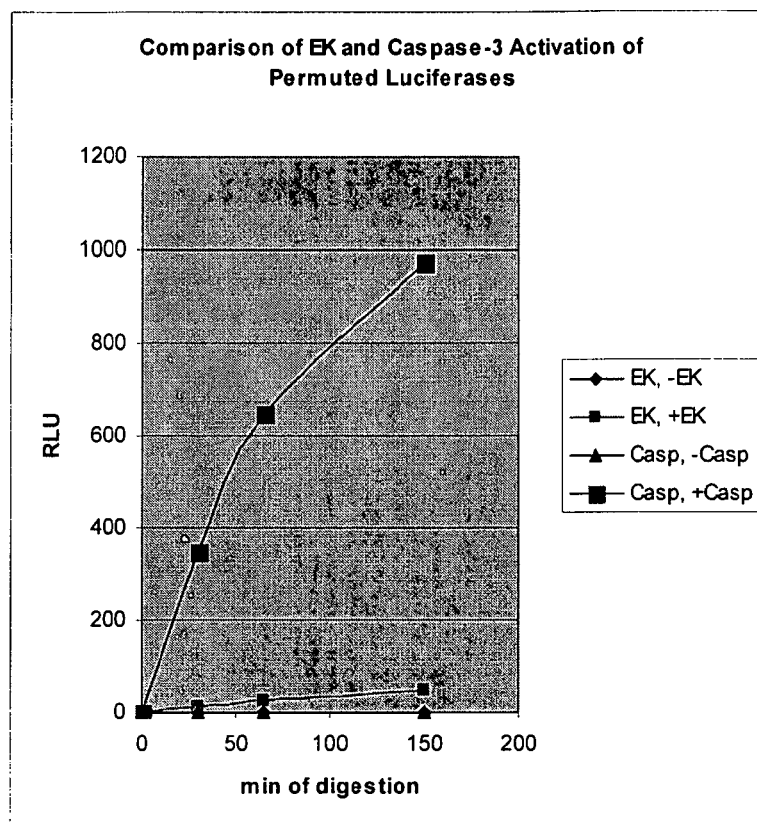
FIG. 11. Comparison of data for a circularly permuted firefly luciferase having an enterokinase site or a caspase-3 site.

Protease digestions were incubated at room temperature and at various times 1 µl was added to 100 µl luciferase assay reagent for reading in the Turner 20/20 luminometer. In this experiment caspase-3 increased the activity of the permuted caspase-luciferase by about 3000-fold to about one quarter that of WT, and EK increased the activity of the EK-luciferase by about 300-fold to about 1.1% of WT (FIGS. 8 and 11). Note that both inserts are the same size, DEVDG (SEQ ID NO:116) in the one case and DDDDG (SEQ ID NO:117) in the other. Thus, longer sequences may be incorporated by replacing the three N-terminal amino acids of luciferase and the six C-terminal amino acids, respectively, from the original termini of the protein. This should permit a site of at least 14-15 amino acids to be incorporated between the two luciferase domains. Note that the 9 residues mentioned above do not appear in the corresponding crystal structure and thus are highly flexible and likely replaceable without incurring a deleterious effect on the enzyme activity.

EXAMPLE VII

Additional Circularly Permuted Constructs

A. PSA is a protease which cleaves Semenogelin I between Gln and Ser in the sequence Ala-Asn-Lys-Ile-Ser-Tyr-Gln-Ser-Ser-Ser-Thr-Glu (SEQ ID NO:21). To generate a modified luciferase with a cleavage substrate for PSA, an oligonucleotide for the related 12mer peptide Ala-Asn-Lys-Ala-Ser-Tyr-Gln-Ser-Ala-Ser-Thr-Glu (SEQ ID NO:22) was cloned between the XhoI and NcoI sites in the plasmid construct described in Example VI. An oligonucleotide having the sequence TCGAAGCTAACAAAGCTTCCTAC-CAGTCTGCGTCCACCGAAC (SEQ ID NO:23) was hybridized to an oligonucleotide having the sequence CATG-GTTCGGTGGACGCAGACTGGTAG-GAAGCTTTGTTAGCT (SEQ ID NO:24). The hybridized oligonucleotides produce a double-stranded fragment having XhoI and NcoI compatible ends, although the NcoI site is reformed while the XhoI site is destroyed. A vector was digested with XhoI and NcoI and ligated to the annealed oligonucleotides, followed by transformation into *E. coli*. Mini-prep DNA was prepared from individual colonies and plasmids were screened for digestion with NcoI but not with XhoI, indicating incorporation of the oligonucleotide containing the protease site. The desired construct was translated in vitro in either a wheat germ (WG) translation extract or a rabbit reticulocyte lysate and the resulting protein treated with purified PSA (Sigma). Translations were performed. Cleavage reactions were performed as below:

The reactions were incubated at room temperature for 20 or 40 minutes. 1 µl of each reaction was added to 100 µl of luciferase assay reagent (LAR) and the light output recorded in a Turner 20/20 luminometer. The following data was obtained:

| 20 minutes | |
|---|---|
| (1) | 3.131 LU |
| (2) | 2061 LU |
| (3) | 0.516 LU |
| (4) | 573.1 LU |
| 40 minutes | |
| (1) | 3.696 LU |
| (2) | 2149 LU |
| (3) | 0.649 LU |
| (4) | 564.6 LU |

The addition of PSA resulted in substantially increased light output. At 20 minutes, the fold activation of the modified luciferase was 658× for the modified luciferase synthesized in the rabbit reticulocyte lysate, and 1,110× for the modified luciferase synthesize in the wheat germ extract.

B. PreScission protease is a fusion protein composed of GST (glutathione S-transferase) and Rhinovirus 3C protease (Amersham). The protease can cleave between the Gln and Gly residues in the sequence Leu-Glu-Val-Leu-Phe-Gln-Gly-Pro (SEQ ID NO:25). Oligonucleotides specifying this sequence were designed and had the sequence (top strand) TCGAGCTGGAAGTTCTGTTCCAGGGTCCGG (SEQ ID NO:26) and (bottom strand) CATGCCGGACCCTGGAA-CAGAACTTCCAGC (SEQ ID NO:27). The annealing of these oligonucleotides resulted in a double-stranded fragment having XhoI and NcoI compatible ends, in which the XhoI site is retained while the NcoI site is destroyed. As in the above example, the annealed oligonucleotides were cloned into a vector which was cut with XhoI and NcoI. To enrich for the desired clones, the ligation mix was recut with NcoI prior to transformation. The desired plasmid was selected and subjected to in vitro translation in a rabbit reticulocyte lysate as above. A digestion reaction was prepared as below:

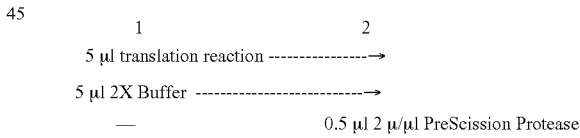

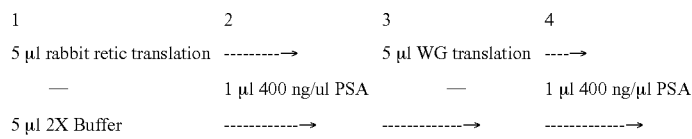

2X Buffer = 100 mM Tris-HCl pH 7.5
    0.3M NaCl
    0.2% Tween-20

The reactions were incubated at room temperature and at various times, 1 µl was added to 100 µl LAR and samples read in a Turner 20/20 luminometer. The following data was generated:

| 20 minutes | |
|---|---|
| (1) | 0.556 LU |
| (2) | 2242 LU |
| 40 minutes | |
| (1) | 0.595 LU |
| (2) | 2500 LU |
| 60 minutes | |
| (1) | 0.610 LU |
| (2) | 2447 LU |

Activation of the luciferase with PreScission protease occurred quickly and resulted in a greater than 4,000 fold increase in luminescence in the presence of the protease.

C. While a high degree of activation was observed by proteolytic treatment of permuted luciferases synthesized in eukaryotic cell-free lysates, a much smaller degree of activation was observed when the unfused proteins were synthesized in *E. coli*. Interestingly, partial purification of the *E. coli* preparations produced proteins with an increased ability to be activated by protease. To efficiently purify the circularly permuted luciferases from bacterial cells, a vector was prepared in which a circularly permuted luciferase having a caspase-3 site was fused to GST in the vector pGEX-6P3 (Amersham). The PCR reaction contained:

5 µl 10×PfuUltra buffer

1 µl 10 mM dNTP

1 µl 5 ng/µl caspase-3 site plasmid

1 µl 100 ng/µl upstream oligonucleotide

1 µl 100 ng/µl downstream oligonucleotide

40 µl H$_2$0

50 µl

The PCR was initiated by the addition of 1 µl 2.5µ/µl PfuUltra DNA polymerase (Stratagene) and was cycled at 95° C. for 30 seconds, 50° C. for 30 seconds, and 72° C. for 1 minute, for 20 cycles, then brought to 4° C.

The upstream oligonucleotide contains a BamH1 and has the sequence AGCTAGGATCCGATACTGCGATTT-TAAGTGTTGTTC (SEQ ID NO:28) and the downstream oligonucleotide contains an EcoRI site and has the sequence AGCTAGAATTCTTACGGAATGATTTGAT-TGCCAAAAATAG (SEQ ID NO:29). The resulting PCR product was digested with EcoR1 and BamH1 and cloned between these sites in the vector, which results in an in-frame fusion of luciferase to GST. The desired plasmid was identified and transformed into the *E. coli* strain Rosetta (Novagen). Cells were grown in LB medium and induced by the addition of IPTG to 1 mM. The best growth conditions were found to be an overnight induction at 25-26° C. Cells were collected and lysed by sonication. Following clearing by centrifugation, the supernatant was applied to a column containing immobilized glutathione and eluted with a buffer containing free glutathione. The yield of fusion protein was about one milligram per liter of initial culture. Activation with caspase-3 was no less than about 1,200 fold and, depending on the conditions of the activation reaction, up to 50,000 fold (with activation overnight on ice).

D. Three circularly permuted luciferases containing the SARS virus protease site TSAVLQSGFR (SEQ ID NO:19) were generated: two for click beetle luciferase (CP1: R=Asn401 and CP2: R=Arg223) and one for a firefly (CP: R=Asp234) luciferase. CP2 has an insertion at a position in click beetle luciferase which corresponds to position 234 in firefly luciferase.

The circular permuted click beetle luciferases with a SARS virus protease site were constructed as follows. A plasmid, pJLC33, which contains an insertion mutant cbg69SARS3 gene between NdeI and BamHI sites and a sequence encoding a SARS virus protease site between SnaBI and SalI as described above, was used as a starting vector. The following primer sets were used to amplify PCR fragments from pJLC1 containing wild-type cbg69:

```
For CP1,
CP1-a:
                                     (SEQ ID NO: 43)
atgcgtcgacGTGAAACGCGAAAAGAACGTGATC
and (SEQ ID NO: 44)
atgcggatccttaGTTCACGTAGCCTTTAGAGACCATA;

CP1-b:
                                     (SEQ ID NO: 45)
atgccatatgAATGTGGAGGCCACTAAAGAAGCCATTG
and (SEQ ID NO: 46)
agtctacgtaGCCGCCAGCTTTTTCGAGGAG;

For CP2,
CP2-a:
                                     (SEQ ID NO: 47)
atgcgtcgacGTGAAACGCGAAAAGAACGTGATC
and (SEQ ID NO: 48)
atgcggatccttaAGGGTCGAGAGCGTGGATCAAACG;

CP2-b:
                                     (SEQ ID NO: 49)
atgccatatgCGTGTGGGTACTCAATTGATCCC
and (SEQ ID NO: 50)
agtctacgtaGCCGCCAGCTTTTTCGAGGAG.
```

The PCR product of CP1-a (or CP2-a) was digested with SalI and BamHI, and cloned into the respective sites in pJLC33, yielding pJLC-cp1a (or pJLC-cp2a). The PCR product of CP1-b (or CP2-b) was digested with NdeI and SnaBI and cloned into the respective sites in pJLC-cp1a (or pJLC-cp2a). The resulting plasmid, pJLC47 (or pJLC48), contains the circular permuted mutant 1 (or 2) of click beetle luciferase with the SARS virus protease site.

For the permuted firefly luciferase, the permuted vectors were modified to incorporate a linker with XhoI and NcoI sites separating the DNA for the original N- and C-termini. The linker was Pi-GAGATCCTCATAAGGCCAA-GAAGCTCGAGATGGTTCCATGGGCCAAAAA CAT-AAAGAAAGGCCCG (SEQ ID NO:20), which removes 6 amino acids from the C-terminus in the first domain and 3 amino acids from the N-terminus of the second domain. The SARS virus N-terminal autocleavage site is SITSAVLQSG-FRKMA (SEQ ID NO:53). Oligonucleotides specifying this sequence were designed as follows: TCGAATCCATCAC-CTCTGCTGTTCTGCAGTCCGGTTTCCGTAAAAT-GGCT C (top strand, SEQ ID NO:51) and CATGGAGC-CATTTTACGGAAACCGGACTGCAGAACAGCAGA-GGTGATG GAT (bottom strand, SEQ ID NO:52). The annealed oligonucleotides retain the NcoI site and lack the XhoI site. The annealed and digested oligonucleotides were cloned into the base vector as above.

Figure 12:
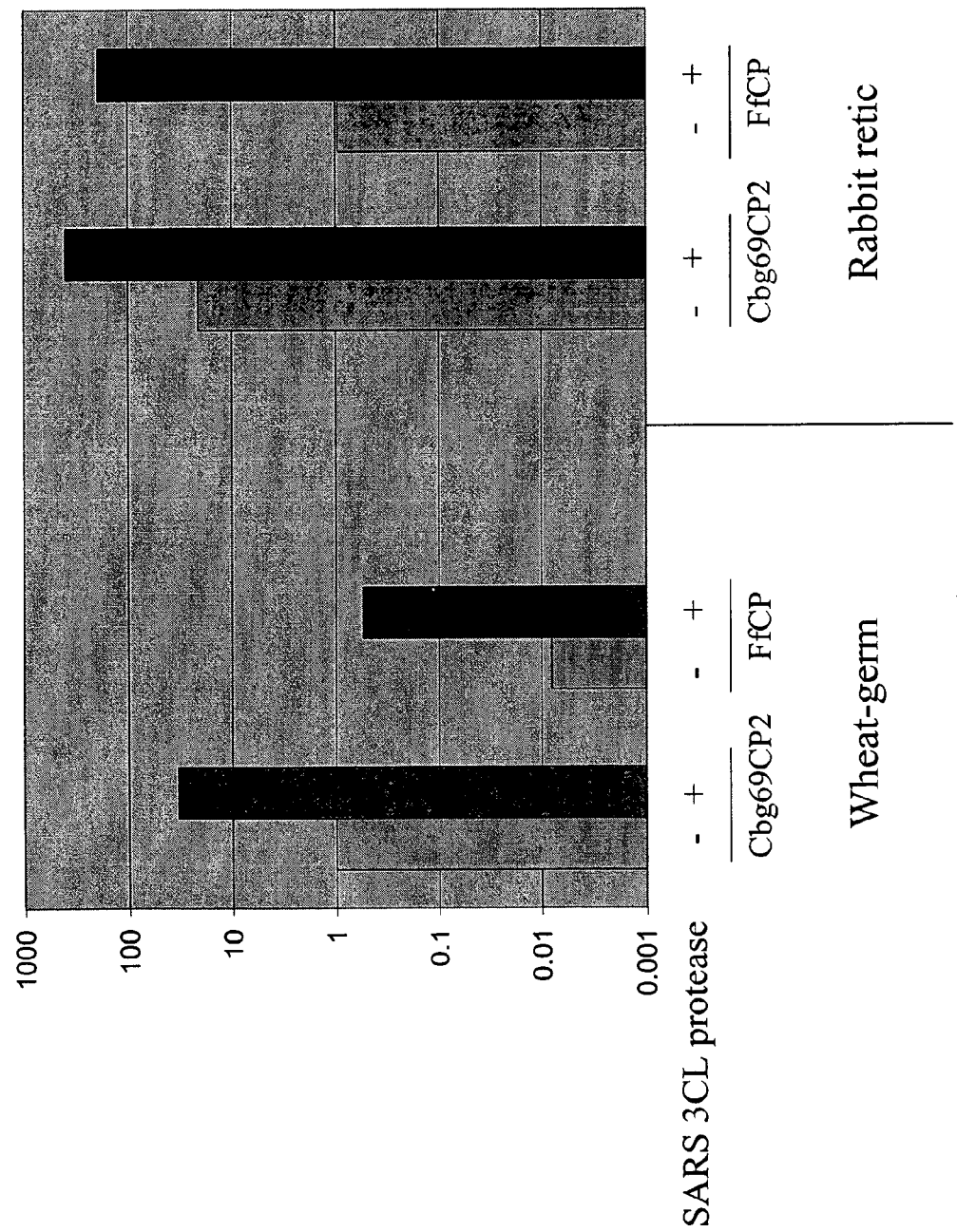
FIG. 12. Graphs showing SARS virus 3CL protease activity with circularly permuted click beetle (CP1: R=Asn401 and CP2: R=Arg223) and firefly (CP: R=Asp234) luciferases having SARS virus protease recognition sites.

All three circular permuted luciferases with SARS virus protease sites, Cbg69CP1, Cbg69CP2 and FfCP, were produced using in vitro translation systems such as a rabbit reticulocyte lysate and/or a wheat germ extract (Promega). The SARS virus protease was partially purified using a pMAL purification system from New England Biolabs. The lysates containing mutant luciferase were mixed with SARS virus protease and luciferase activity monitored. Cbg69CP2 and FfCP were activated 20-30-fold and 60-200-fold, respectively (FIG. 12), whereas Cbg69CP1 was not activated (data not shown), after 1 hour of incubation with about 0.3 µg of SARS virus protease at room temperature.

E. Activation of procaspase-3 to produce active caspase-3 is a proxy for the induction of apotosis in living cells. To ascertain whether a modified luciferase could be used to monitor apotosis in cells, a circularly permuted luciferase containing a caspase-3 cleavage site was cloned into a mammalian expression vector under control of the CMV promoter and introduced into Hela cells via transient transfection. Cells were then treated with the protein TRAIL to induce apoptosis via activation of the death receptor to form active caspase-8, which in turn activates procaspase-3 to caspase-3. Thus, the appearance of active caspase-3 should be accompanied by an increase in luminescence as the luciferase substrate is cleaved and activated by the enzyme.

A PCR fragment of permuted luciferase containing the caspase-3 cleavage site was generated using primers containing sites for NheI and EcoRI and cloned into the vector pCI-neo (Promega) between these sites. The amplification was performed as above with the upstream primer GAC-TAGCTAGCATGGATACTGCGATTTTAAGTGTTGTTC (SEQ ID NO:30). The resulting construct had an optimum Kozak sequence of the general form ANNATGG. DNA was transfected into Hela cells using TransFast transfection reagent (Promega) and apoptosis was initiated by adding TRAIL protein (Biomol) at 1 µg/µl in DMEM+10% Cosmic Calf Serum. Some wells were transfected with the plasmid pGL3-control which carries the natural firefly luciferase gene (non-permuted) under the control of the SV40 early promoter/enhancer. At the indicated times, 100 µl of Bright-Glo reagent were added to the wells and luminescence recorded in an Orion luminometer (0.5 second reads).

| Minutes | (−)TRAIL | (+)TRAIL | (−)TRAIL | (+)TRAIL |
|---|---|---|---|---|
| 0 | 172 | 134 | 2734 | 2232 |
| 30 | 150 | 186 | 3288 | 2448 |
| 60 | 164 | 330 | 2906 | 3198 |
| 90 | 294 | 1442 | 4058 | 3636 |
| 120 | 462 | 1508 | 3880 | 3946 |
| 150 | 398 | 940 | 2972 | 2856 |
|  | pCaspase | pCaspase | pGL3-ctl | pGL3-ctl |

Figure 13:
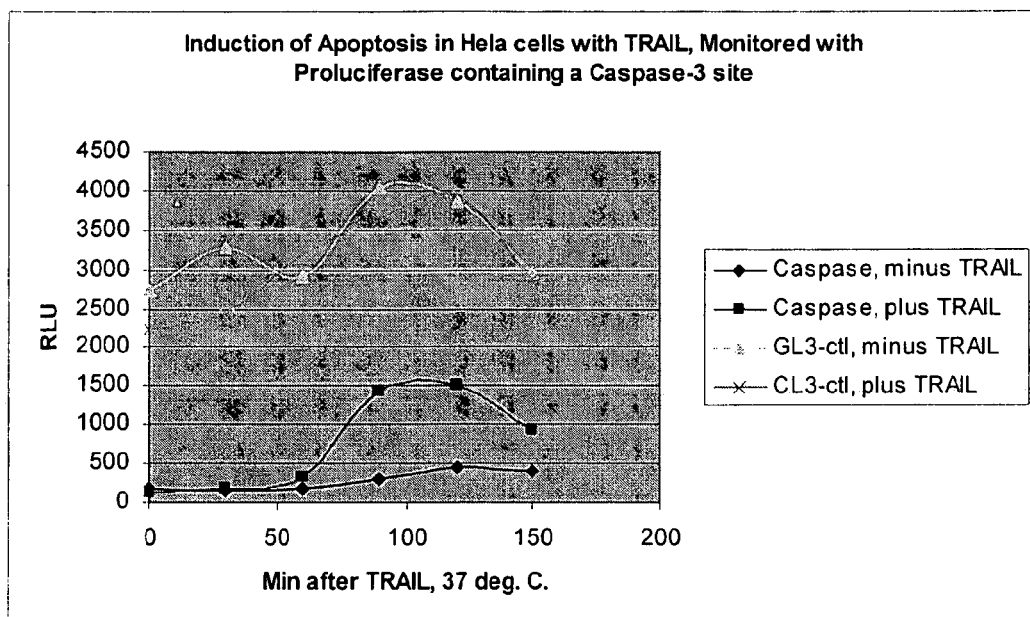
FIG. 13. RLU for a circularly permuted luciferase having a caspase-3 site, which was treated with TRAIL.

The data in FIG. 13 show that for cells receiving the permuted luciferase-caspase-3 plasmid, TRAIL protein induces luminescent activity between 1-2 hours after which luminescence fell off. This effect is not seen in wells containing medium alone. Wells containing pGL3-control plasmid showed no difference between medium alone and medium+TRAIL. The general increase in LU seen upon changing the medium may be due to the induction of protein synthesis, which for pGL3-control luciferase is in an active form, while for the pCI-neo-caspase plasmid, the luciferase is in an inactive form. The small increase seen in this case with medium alone may be due to the accumulation of dead cells over the course of the assay, as a dead cell background is observed due to the stress of the transfection.

EXAMPLE VIII

Cell-Based Assays with Modified Luciferases

To provide a vector which encodes an intramolecular control and detects caspase-3 activity, vectors which encoded a fusion protein of the invention were prepared. *Renilla* luciferase (control) was fused to either the N-terminus or the C-terminus of a modified click beetle luciferase containing DEVD (SEQ ID NO:106) after residue 400 (Cbg69DEVD; DEVD is represented by SEQ ID NO:106). The linker sequence of (Gly(2)SerGly(4)SerGly(4)SerGly(2)) (SEQ ID NO:115) was placed between the two proteins.

To make a rLuc-linker-Cbg69DEVD (DEVD is represented by SEQ ID NO:106) fusion, a pair of oligonucleotides, atgcatatCATATGGCTTCCAAGGTGTACGACCCC (SEQ ID NO:54) and atgcATTAATgccaccggaaccgccgc-caccgctaccgccgccaccgctgccCT-GCTCGTTCTTCAGCACGCG CTCCACG (SEQ ID NO:55), was used to amplify a full length *Renilla* luciferase gene (rLuc) from plasmid pJLC6. The resulting PCR fragment was digested with NdeI and AseI, and cloned into the NdeI site of pJLC23, which encodes Cbg69DEVD (DEVD is represented by SEQ ID NO:106).

To make a Cbg69DEVD-linker-rLuc (DEVD is represented by SEQ ID NO:106) fusion, a pair of oligonucleotides, atgcatatCATATGGTGAAACGCGAAAAGAACGT (SEQ ID NO:56) and atgcATTAATgccaccggaaccgccgc-caccgctaccgccgccaccgctGCCGC-CAGCTTTTTCGAGGAGTTG CTTCAG (SEQ ID NO:57), was used to amplify a full length Cbg69DEVD (DEVD is represented by SEQ ID NO:106) gene from plasmid pJLC23. The resulting PCR fragment was digested with NdeI and AseI, and cloned into the NdeI site of pJLC6, which contains the rLuc.

Figure 14:
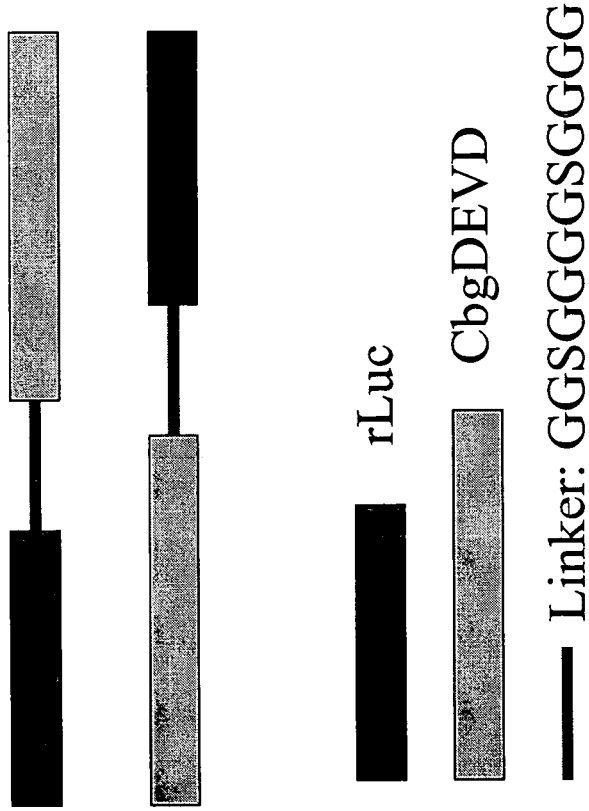
FIG. 14. Schematic of vectors for a dual luciferase caspase assay (SEQ ID NOs:106 and 115).

FIG. 14 shows that each fusion protein had *Renilla* luciferase as well as click beetle luciferase activities.

EXAMPLE IX

Evaluation of Ability of Luciferase Fragments to Associate and Form Functional Luciferase In one embodiment, the invention provides a system where two independent fragments of luciferase can complement each other to produce a functional protein.

Materials and Methods

Three constructs were designed to evaluate the ability of N- and C-terminal fragments of luciferase to associate and form a functional luciferase protein in vitro and in vivo (FIG. 15). The N-terminal 699 nucleotides of the firefly luciferase gene (amino acids 1-233) were amplified from pSP-luc+ (Promega Corporation) using forward primer 5'ATGCGCTAGC-CCGGGGATATCGCCACCATGGAAGACGC-CAAAAACAT AAAG3' (SEQ ID NO:60) and reverse primer 5'GATAAAAACCGTTAGTTTAGTAAGGCAT-TCCTAGGATCGA3' (SEQ ID NO:61) under the following conditions: 95° C. for 2 minutes, 25 cycles of 95° C. for seconds, 50° C. for 30 seconds, and 72° C. for 2 minutes, followed by 72° C. for 10 minutes on a Perkin Elmer 2400 ThermalCycler. A NheI restriction site was engineered onto the 5' end of the forward primer and a BamHI restriction site was engineered onto the 5' end of the reverse primer. The resultant N-terminal luciferase fragment was subsequently cloned into the NheI and BamHI restriction sites of the pBIND vector using established techniques (Sambrook et al., 1989), yielding expression vector pJLC 62 (n luc).

Similarly, the C-terminal 951 nucleotides of the firefly luciferase gene (amino acids 234-550) were amplified from pSP-luc+ using forward primer 5'ATGCGCTAGCCCGG-GATATCGCCACCATGGATACTGCGATTTTAA3' (SEQ ID NO:62) and reverse primer 5'TTGGCGCGCCGGATC-CTTACACGGCGATCTTTCCGCCCTTCTTG3' (SEQ ID NO:63) using the same PCR conditions described above for the N-terminal cloning. NheI and BamHI restriction sites were engineered into the primers as described above for the N-terminal primers, and the C-terminal luciferase fragment was cloned into the NheI and BamHI of the pBIND vector, yielding expression vector pJLC 63 (c luc).

The whole luciferase gene (1650 nucleotides, 550 amino acids) was cloned into the pBIND vector in the same manner as that used for the N- and C-terminal clones, using forward primer 5'ATGCGCTAGCCCCGGGATATCGCCAC-CATGGAAGACGCCAAAAACA3' (SEQ ID NO:64) and reverse primer 5'TTGGCGCGCCGGATCCTTACACGGC-GATCTTTCCGCCCTTCTTG3' (SEQ ID NO:65) using the same PCR conditions described above. The resultant expression vector, pJLC64 (full length FF), was used as a control for the protein complementation experiments.

All constructs were verified for correct protein size using the TnT® Coupled Wheat Germ Extract System in conjunction with the FluoroTect™ Green$_{Lys}$ in vitro Translation Labeling System (Promega Corporation) following the manufacturer's protocol.

In vitro protein complementation experiments were performed using the TnT® Coupled Wheat Germ Extract System in conjunction with the FluoroTect™ Green$_{Lys}$ in vitro Translation Labeling System (Promega Corporation) following the manufacturer's protocol. After translation, 2 µl of each sample were added to 100 µl of Luciferase Assay Reagent and luminescence was measured using a Veritas Luminometer.

In vivo complementation experiments were performed in Chinese Hamster Ovary (CHO) and 293 human embryonic kidney tissue culture cells. Tissue culture cells, either CHO or 293 cells, were seeded into 6-well tissue culture plates, allowed to grow overnight at 37° C. and 5% CO$_2$, and transfected at 80% confluency the following day. Transfection was performed using TransFast™ Transfection Reagent (Promega Corporation) according to the manufacturer's recommendations. Briefly, for control reactions, 1 µg of either pJLC 62, pJLC 63, or pJLC 64 was transfected (3 µl Trans-Fast™ Reagent/µg DNA) with 1 µg of pBIND control plasmid (original vector with no firefly luciferase gene) so that the final concentration for each transfection was 2 µg total DNA. For the protein complementation test, 1 µg of pJLC62 and 1 µg of pJLC63 were transfected following the same protocol. Twenty-four hours post-transfection, cells were trypsinized and divided into two groups for each transfection condition. 250 µl of 1× Passive Lysis Buffer (Promega Corporation, PLB) was added to one group and 250 µl of 1 Phosphate Buffered Saline (PBS) was added to the other group. Groups with PLB were subjected to one freeze thaw cycle at −80° C. to ensure lysis of the tissue culture cells, whereas the groups with PBS were not subjected to freeze thaw thereby maintaining non-lysed cells. Luminescence from all groups was measured using the Dual-Luciferase® Reporter Assay System according to the manufacturer's recommendation. Basically, 20 µl from each group was added to a white, 96-well plate in triplicate and the assay was performed on a Veritas Luminometer. All firefly luciferase data was normalized to Renilla luciferase signal.

Results

Figure 16A:
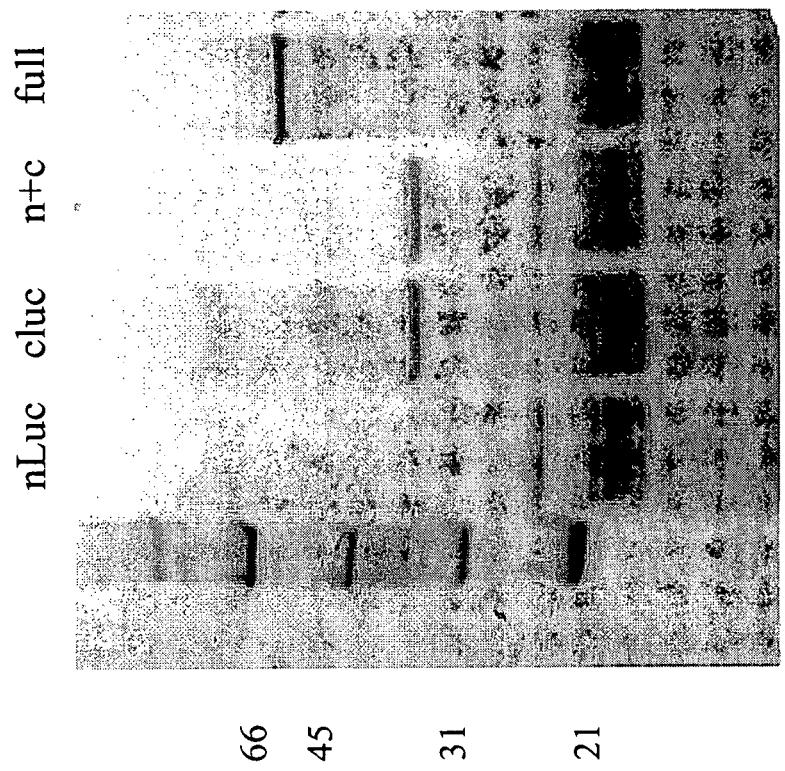
FIG. 16A. SDS-PAGE analysis of full-length firefly luciferase, N-terminal portion of firefly luciferase, C-terminal portion of firefly luciferase or a mixture of the N-terminal and C-terminal portions.
Figure 16B:
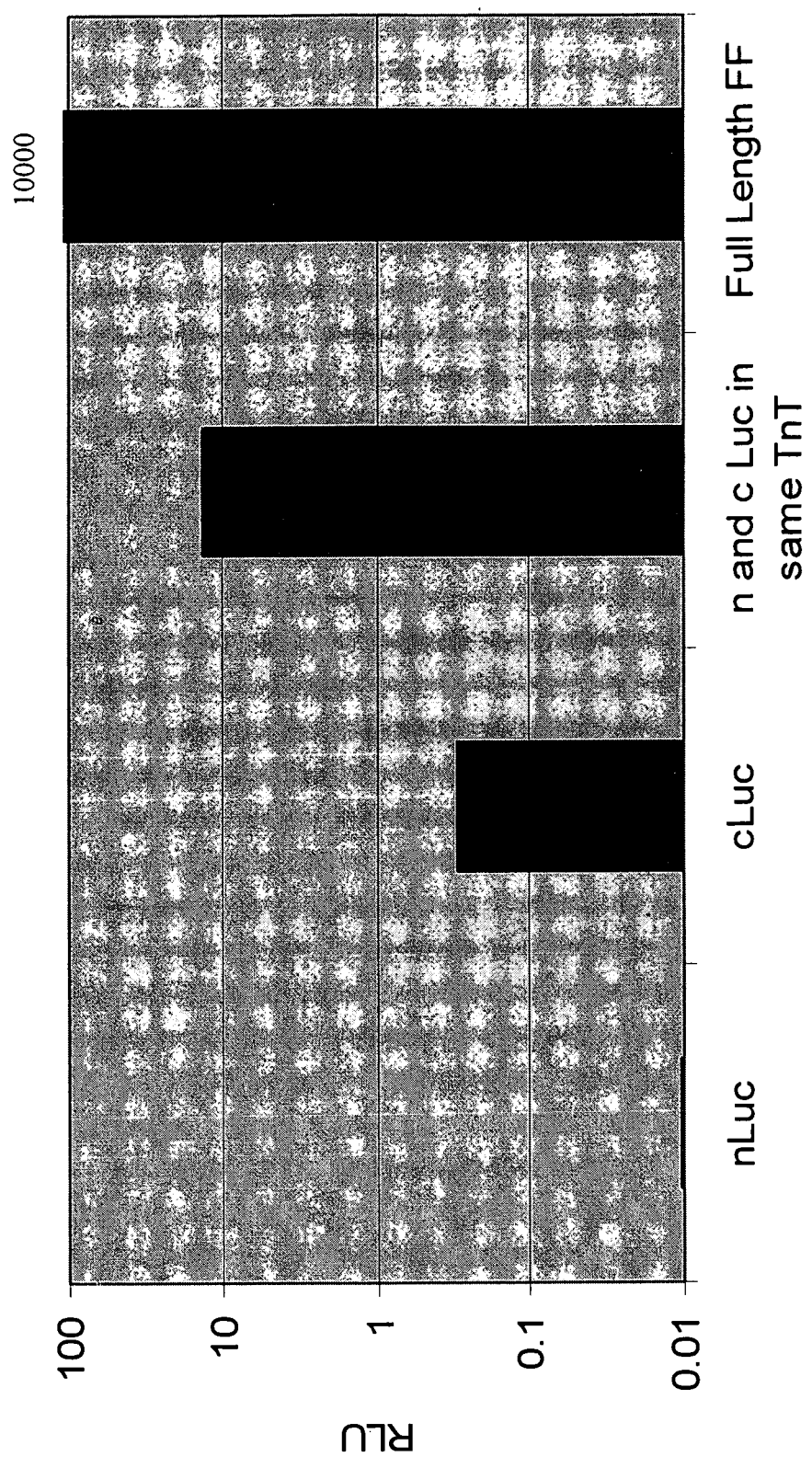
FIG. 16B. In vitro activity of full-length firefly luciferase, N-terminal portion of firefly luciferase, C-terminal portion of firefly luciferase or a mixture of the N-terminal and C-terminal portions.
Figure 17:
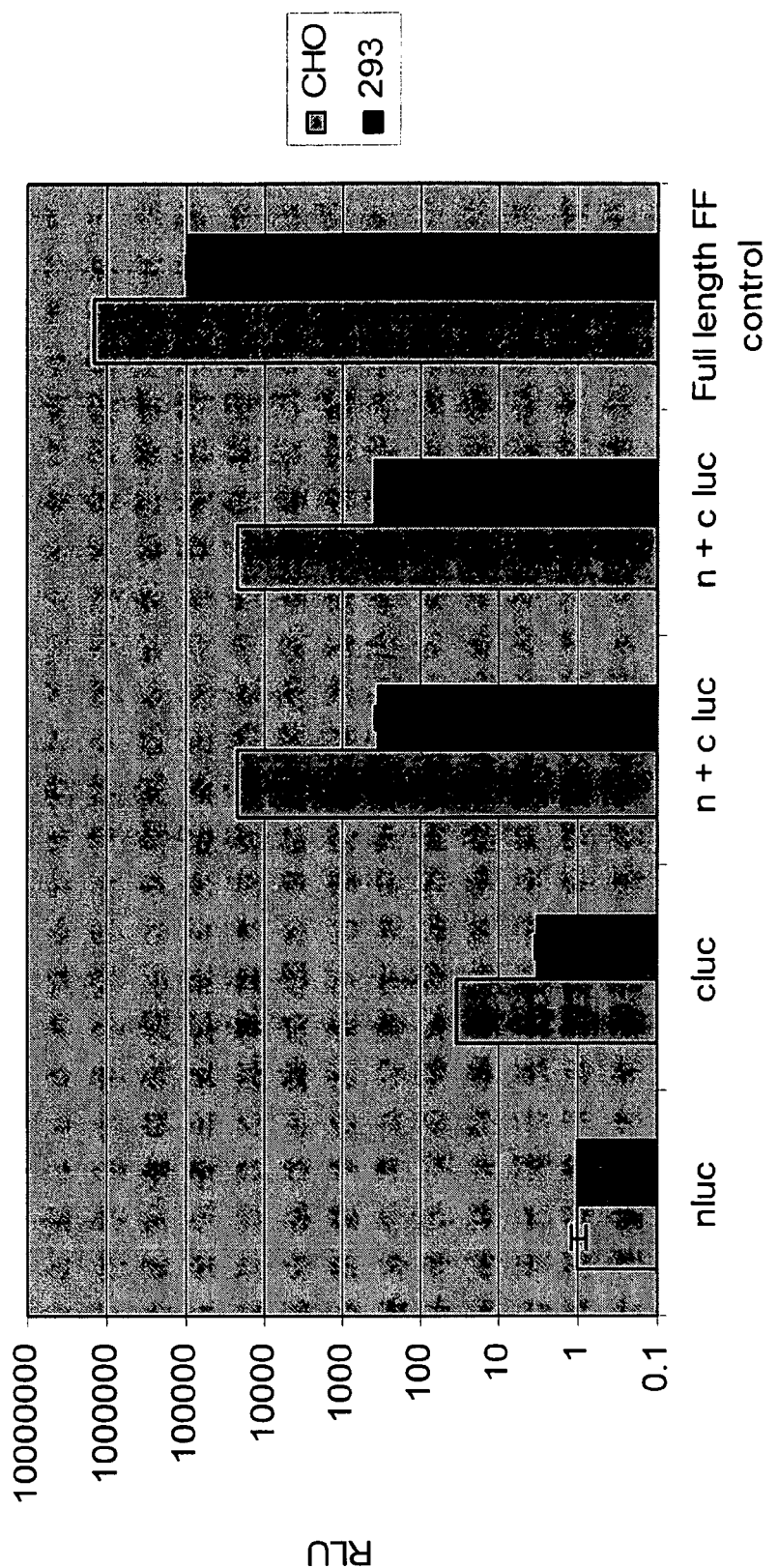
FIG. 17. In vivo activity of luciferase proteins in CHO or 293 mammalian cell extracts.

All 3 constructs shown in FIG. 15 yielded a protein of the correct size (FIG. 16A). The activation of a circularly permuted firefly luciferase upon protease cleavage described hereinabove suggested that fragments of luciferase could complement and reconstitute enzyme activity. As can be seen in FIG. 16B (N- and C-fragments of luciferase in the same TnT reaction), in vitro protein complementation of the N- and C-terminal luciferase fragments yielded a functional protein when compared to the full-length luciferase protein. Moreover, in vivo protein complementation occurred in both CHO and 293 tissue culture cells (FIG. 17). Similar trends were seen even if the tissue culture cells were not lysed (PBS; data not shown).

EXAMPLE X

Detection of Non-Covalent Association of Luciferase Fusion Proteins in a Modulator System In one embodiment, the invention provides a modulator system with an exogenous agent (effector A) that induces or enhances, or alternatively inhibits, binding of two moieties, and optionally another exogenous agent (effector B) that dissociates, or alternatively enhances, respectively, binding the two moieties. For instance, such a system may employ rapamycin as an inducer of binding, and FK506 as a dissociator of binding, of FKBP and FRB which are fused to a luciferase.

A. In Vitro Experiments Demonstrating a Luciferase Modulator System

Materials and Methods

Figure 18:
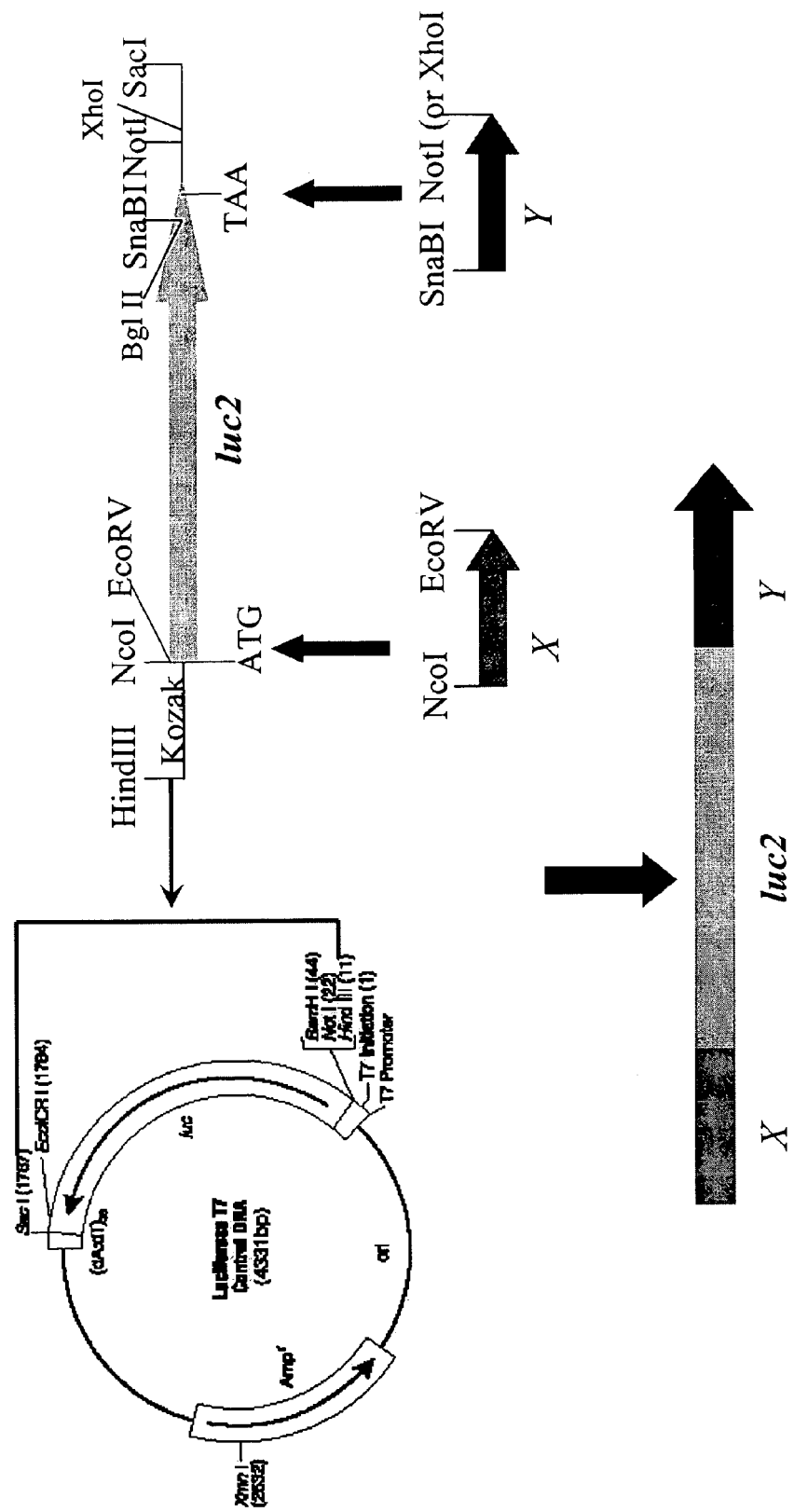
FIG. 18. Cloning strategy for preparing constructs to express fusions of luciferase with binding partners X or Y.

A human codon optimized firefly luciferase gene (luc2.0) was amplified by polymerase chain reaction (PCR) from pGL4.10[luc2] (Promega Corporation) (SEQ ID NO:66) using the forward primer 5'ATGCAAGCTTGGATCCGTT-TAAACGCCACCATGGATATCGCCAAAAAC ATTAA-GAAGGGCCCAG3' (SEQ ID NO:67) and reverse primer 5'GAGCTCGCGGCCGCCTCGAGTTATACG-TAGATCTTGCCGCCCTTC3' (SEQ ID NO:68) under the following conditions: 95° C. for 2 minutes followed by 25 cycles of 95° C. for 30 seconds, 50° C. for 30 seconds and 72° C. for 2 minutes, with a final extension of 72° C. for 10 minutes. NcoI and EcoRV restriction endonuclease sites were engineered on the 5' end of the forward primer to facilitate the generation of a N-terminal fusion with the luciferase protein. SnaBI, NotI, and SacI restriction endonuclease sites were engineered on the 5' of the reverse primer to facilitate generation of a C-terminal fusion with the luciferase protein. The amplified luciferase gene with additional cloning sites on the 5' and 3' ends was cloned into a HindIII/SacI site of the Luciferase T7 Control Vector (Promega Corp., Cat No #L4821) replacing the luciferase gene normally present in the Control Vector. The resulting vector was called pJLC 65. A general scheme for cloning into the in vitro expression Luciferase T7 Control Vector can be seen in FIG. 18.

Several expression constructs were created using the pJLC 65 vector; a N-terminal fusion of FRB to the firefly luciferase (pJLC 66), a C-terminal fusion of FKBP to firefly luciferase (pJLC 67), and a double fusion of FRB (N-terminus) and FKBP (C-terminus) to firefly luciferase (pJLC 68). FRB was obtained from a plasmid from Blue Heron containing a synthetic gene for FRB (CCATGGTGGCCATCCTCTGGCAT-GAGATGTGGCATGAAGGCCTGGAAG AGGCATCTCGTTTGTACTTTGGGGAAAG- GAACGTGAAAGGCATGTTTGA GGTGCTGGAGC-CCTTGCATGCTATGATGGAACGGGGC-CCCCAGACTCTG AAGGAAACATCCTTTAATCAGGCCTATG-GTCGAGATTTAATGGAGGCCC AAGAGTGGTGCAG-GAAGTACATGAAATCAGGGAATGTCAAGGACCTCA CCCAAGCCTGGGACCTCTATTATCATGT-GTTCCGACGAATCTCAGGTGGC GGAGATATC; SEQ ID NO:69). FRB was cut from the Blue Heron vector using a NcoI restriction endonuclease site on the 5' end and an EcoRV restriction site on the 3' end, and was cloned into the N-terminus of the luciferase gene using known molecular biological techniques (Sambrook et al., 1989).

FKBP was obtained from a plasmid from Blue Heron containing a synthetic gene for FKBP (TACGTAGGTGGAGT-GCAGGTGGAAACCATCTCCCCAGGAGACGGGCGC ACCTTCCCCAAGCGCGGCCAGACCT-GCGTGGTGCACTACACCGGGATGC TTGAAGATG-GAAAGAAATTTGATTCCTCCCGGGACA-GAAACAAGCCCTT TAAGTTTATGCTAGGCAAGCAGGAGGT-GATCCGAGGCTGGGAAGAAGG GGTTGCCCAGAT-GAGTGTGGGTCAGAGAGCCAAACTGAC-TATATCTCCA GATTATGCCTATGGTGCCACTGGGCAC-CCAGGCATCATCCCACCACATG CCACTCTCGTCT-TCGATGTGGAGCTTCTAAAACTGGAAT-GACTCGAGGC GGCCGC; SEQ ID NO:70). FKBP was cut from the Blue Heron vector using SnaBI restriction endonuclease site on the 5' end and a NotI restriction endonuclease site on the 3' end of the gene so that the FKBP fragment could be cloned into the C-terminus of the luciferase gene. The double fusion included FRB and FKBP on the N-terminus and C-terminus (respectively).

The four luciferase constructs were evaluated for correct expressed protein size using the TnT® Coupled Wheat Germ Extract System in conjunction with the FluoroTect™ Green$_{Lys}$ in vitro Translation Labeling System (Promega Corporation) following the manufacturer's protocol. Briefly, in each of four reactions 1 μg of the appropriate DNA was added to a 50 μl reaction including the FluoroTect™ Green$_{Lys}$ tRNA. A sample from each reaction (5 μl) was run on a 10% NuPAGE® Novex Pre-Cast Bis-Tris gel (Invitrogen Corporation) using 1× NuPAGE® MES SDS running buffer as described in the NuPAGE® Technical Guide (Version E, IM-1001). Gels were imaged using the FluorImager SI (Molecular Dynamics).

For the in vitro assay, 5 μl from each TnT® reaction described above were separately added to 95 μl of 1× Passive Lysis Buffer (Promega Corporation) with or without 0.2 μM rapamycin (BioMol). After addition of rapamycin, 10 μl from each sample were added to 100 μl of Luciferase Assay Reagent (furnished with the TnT® System) and luminescence was measured using a Turner 20/20 Luminometer (Turner BioSystems).

To study whether the interaction between FRB and FKBP could be modulated, FK506, which is known to compete with rapamycin and inhibit the interaction between the fusion partners, was used in in vitro experiments. The double fusion FRB-luc2-FKBP was transcribed and translated as described above. After translation, 4 μl of sample was mixed with 5 μl 2×FLICE buffer (100 mM HEPES, pH 7.5, 200 mM NaCl, 0.2% CHAPS, 2 mM EDTA, 20% glycerol, 20 mM DTT) and 1 μl rapamycin (10 nM) with varying concentrations of FK506 (Tacrolimus, Antibioticplus.com) of 0, 1, 2, 5, 10, 20 and 40 nM (equivalence of 0, 0.82, 1.64, 4.1, 8.2, 16.4 and 32.8 ng/ml Tacrolimus). The samples were incubated at room temperature for 15 minutes, after which 5 μl of sample was diluted in 100 μl of Luciferase Assay Reagent and luminescence was measured on a Turner 20/20 Luminometer.

Results

Figure 19:
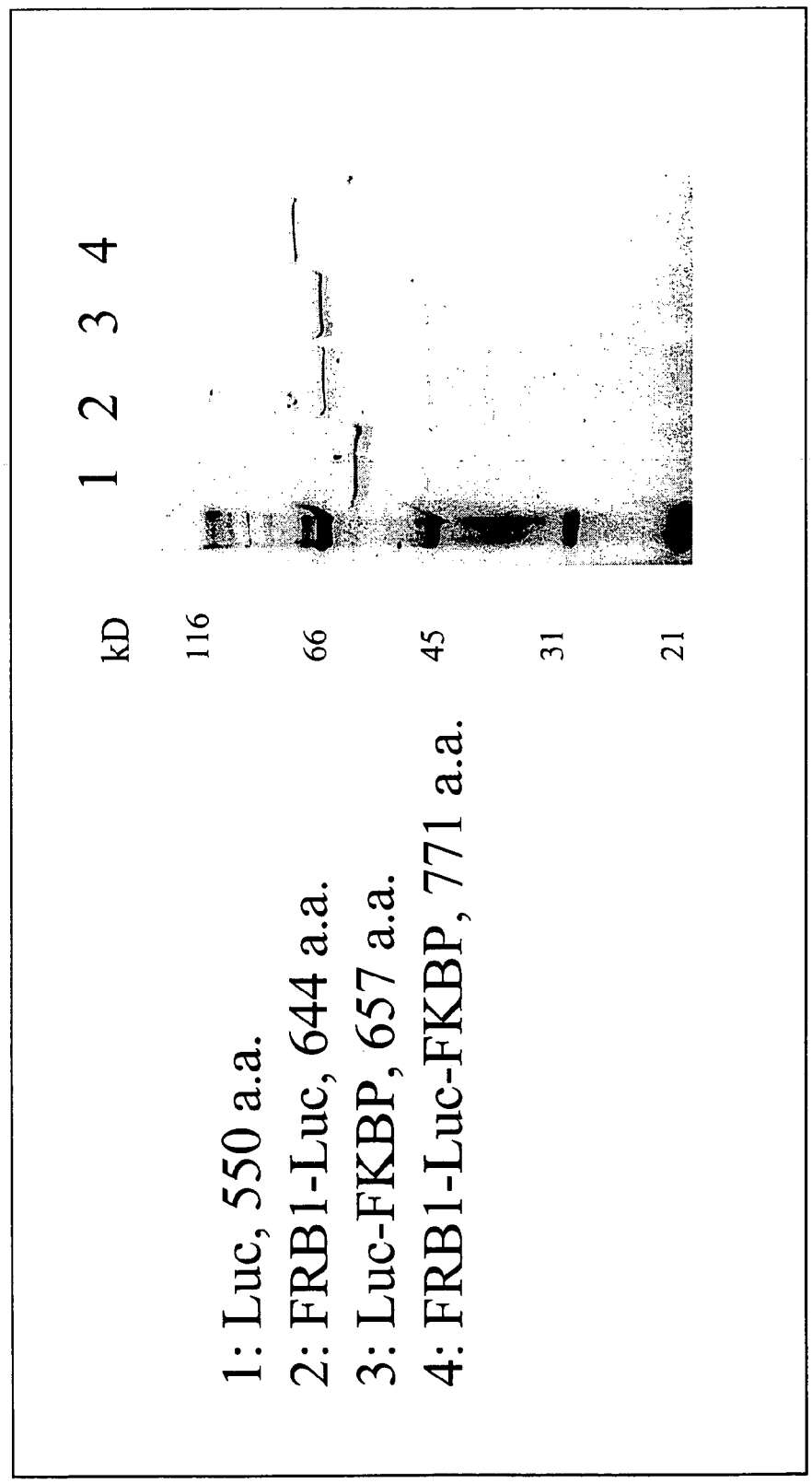
FIG. 19. SDS-PAGE gel analysis of unmodified luciferase protein and fusions of luciferase with one or more heterologous sequences generated using an in vitro transcription/translation reaction.

Four constructs were prepared: luc2 (encoding a firefly luciferase; 550 amino acids), FRB-luc2 (encoding a fusion of FRB and a firefly luciferase; 644 amino acids), luc2-FKBP (encoding a fusion of a firefly luciferase and FKBP; 657 amino acids), and FRB-luc2-FKBP (encoding a double fusion; 771 amino acids). The four constructs (three controls and one double fusion) were evaluated for correct expressed protein size using the TnT® Coupled Wheat Germ Extract System in conjunction with the FluoroTect™ Green$_{Lys}$ in vitro Translation Labeling System. All four constructs yielded a protein of the correct size (FIG. 19).

Figure 20A:
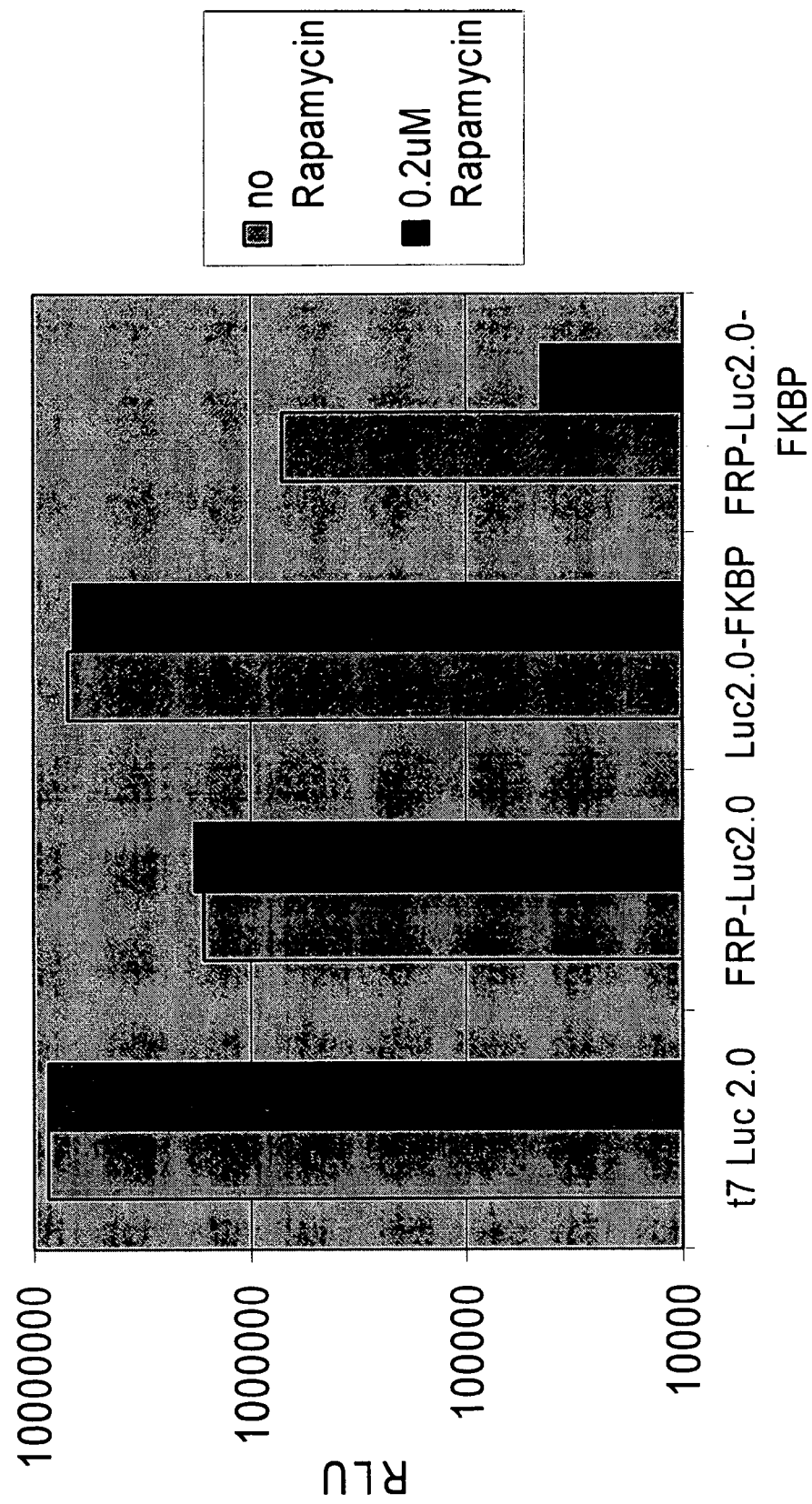
FIG. 20A. Luciferase activity of unmodified luciferase (Luc2), luciferase fused to FRB (rapamycin binding protein), luciferase fused to FKBP (FK506 binding protein) and luciferase fused to FRB and FKBP, in the presence or absence of rapamycin.
Figure 20B:
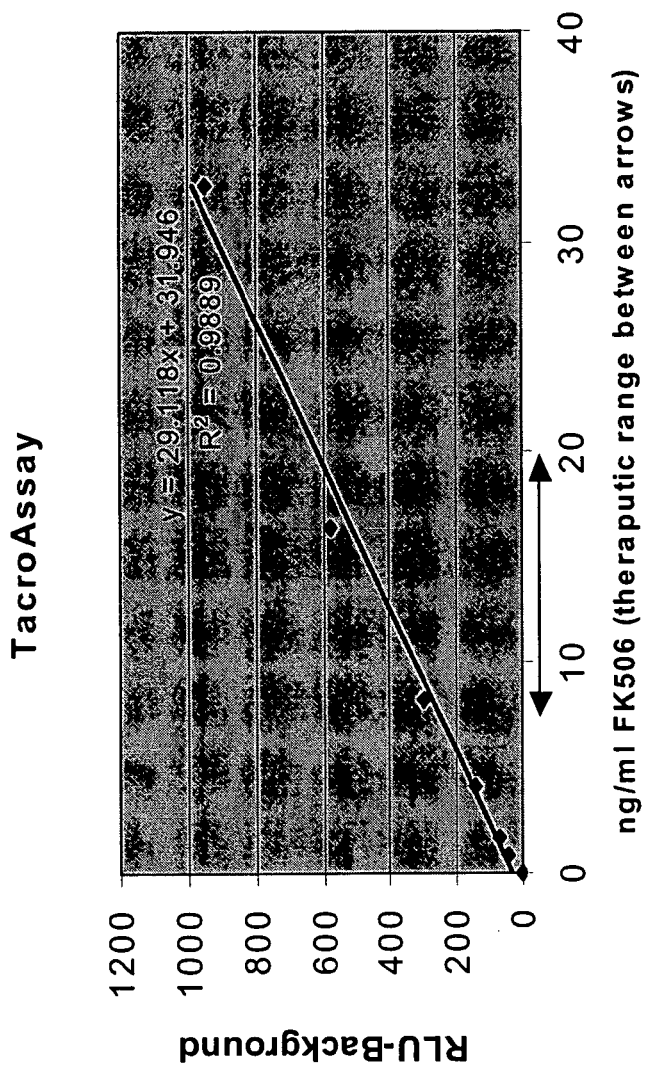
FIG. 20B. Luciferase activity of a fusion of luciferase and FRB and FKBP in the presence of increasing concentrations of FK506.

The constructs were then used in experiments to detect an interaction between the two fusion partners FRB and FKBP in an in vitro system. In the presence of the inducer rapamycin, the two fusion partners should associate resulting in a decrease in luminescence. The addition of rapamycin resulted in a 20-fold reduction in relative luminescence with the double fusion FRB-luc2-FKBP when compared to the control reactions (FIG. 20A). Therefore, in the presence of rapamycin, the two binding partners in the double fusion with luciferase associated, thereby restricting the luciferase enzyme so that it could not interact efficiently with the luciferin substrate. Conversely, with addition of increasing amounts of FK506, luminescence of the double fusion reaction increased in response to increasing amounts of FK506 (FIG. 20B).

B. Another Luciferase Modulator System

Materials and Methods

Figure 21A:
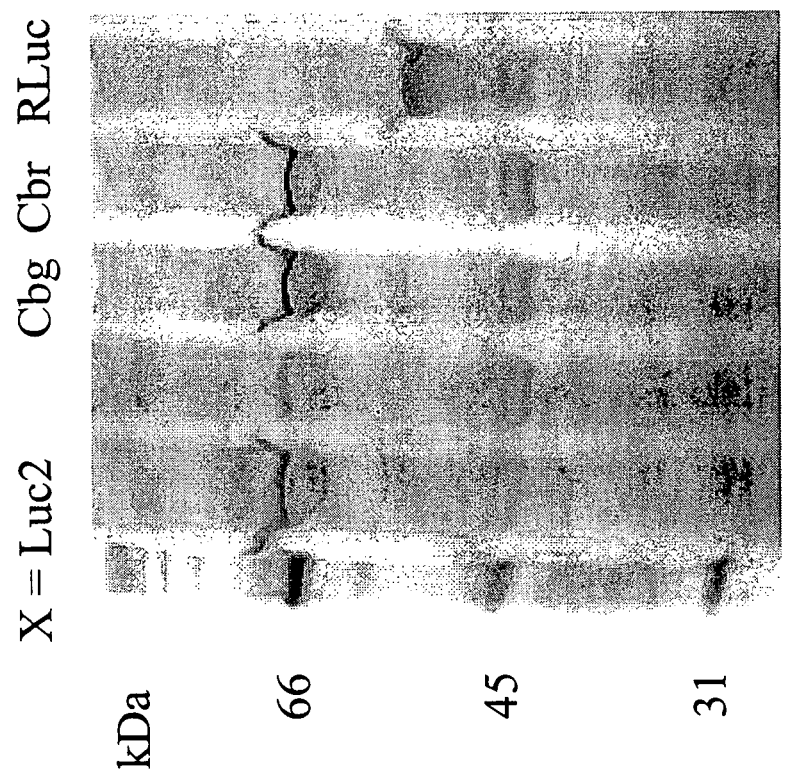
FIG. 21A. SDS-PAGE analysis of fusions of firefly luciferase (Luc2), click beetle luciferase (Cbg and Cbr) and Renilla (RLuc) luciferase with FRB and FKBP.

Cloning was performed as described above with the following exceptions. The red click beetle gene (cbr) was amplified out of pCBR-Basic (Promega Corporation) using the forward primer 5'ATGCGATATCGTGAAACGCGAAAA-GAACG3' (SEQ ID NO:71) and reverse primer 5'GCATA-GATCTTACCGCCGGCCTTCACCAAC3' (SEQ ID NO:72). An EcoRV site was engineered into the 5' end of the forward primer and a BglII was engineered into the 5' end of the reverse primer, and the corresponding amplified fragment subsequently cloned into the corresponding sites in pJLC 68. The green click beetle gene (cbg) was amplified out of pCBG68-Basic (Promega Corporation) using the forward primer 5'ATGCGATATCGTGAAACGCGAAAAGAACG3' (SEQ ID NO:73) and the reverse primer 5'GCATAGATCT-TGCCGCCAGCTTTTTCGAGGAGTTG3' (SEQ ID NO:74). The same restriction sites were engineered into these primers as for the red click beetle for cloning into the pJLC 68 vector. The *Renilla* luciferase gene (Rluc) was amplified from phRL-null (Promega Corporation) using the forward primer 5'ATGCTACGTAGCTTCCAAGGTGTACGACCCCG3' (SEQ ID NO:75) and the reverse primer 5'GCATAGATCT-TCTGCTCGTTCTTCAGCACGCG3' (SEQ ID NO:76). A SnaBI site was engineered into the 5' end of the forward primer and a BglII site was engineered into the 5' end of the reverse primer for cloning into the pJLC 68 vector on the EcoRV (blunt end ligation with SnaBI) and BglII. The cloning of cbg, cbr, and Rluc into pJLC 68 resulted in double fusions of the type FRB-luciferase-FKBP. Clones were verified for correct protein size (FIG. 21A). Double fusions were transcribed and translated and luminescence measured as described above, with the exception that for the rapamycin experiments only 0.2 μM rapamycin was used.

Results

To determine whether a similar modulation of the FRB and FKBP system that was seen with the firefly luciferase protein could also be seen with other species of luciferase, the firefly luciferase gene was replaced with two modified click beetle genes, red and green, from *Pyrophorus plagiophalam*, and the luciferase gene from *Renilla reniformis*. The cloning of cbg, cbr, and Rluc into pJLC 68 resulted in double fusions of FRB-luciferase-FKBP. Clones were verified for correct protein size (FIG. 21A). Double fusions were transcribed and translated, and luminescence measured, as described above.

Figure 21B:
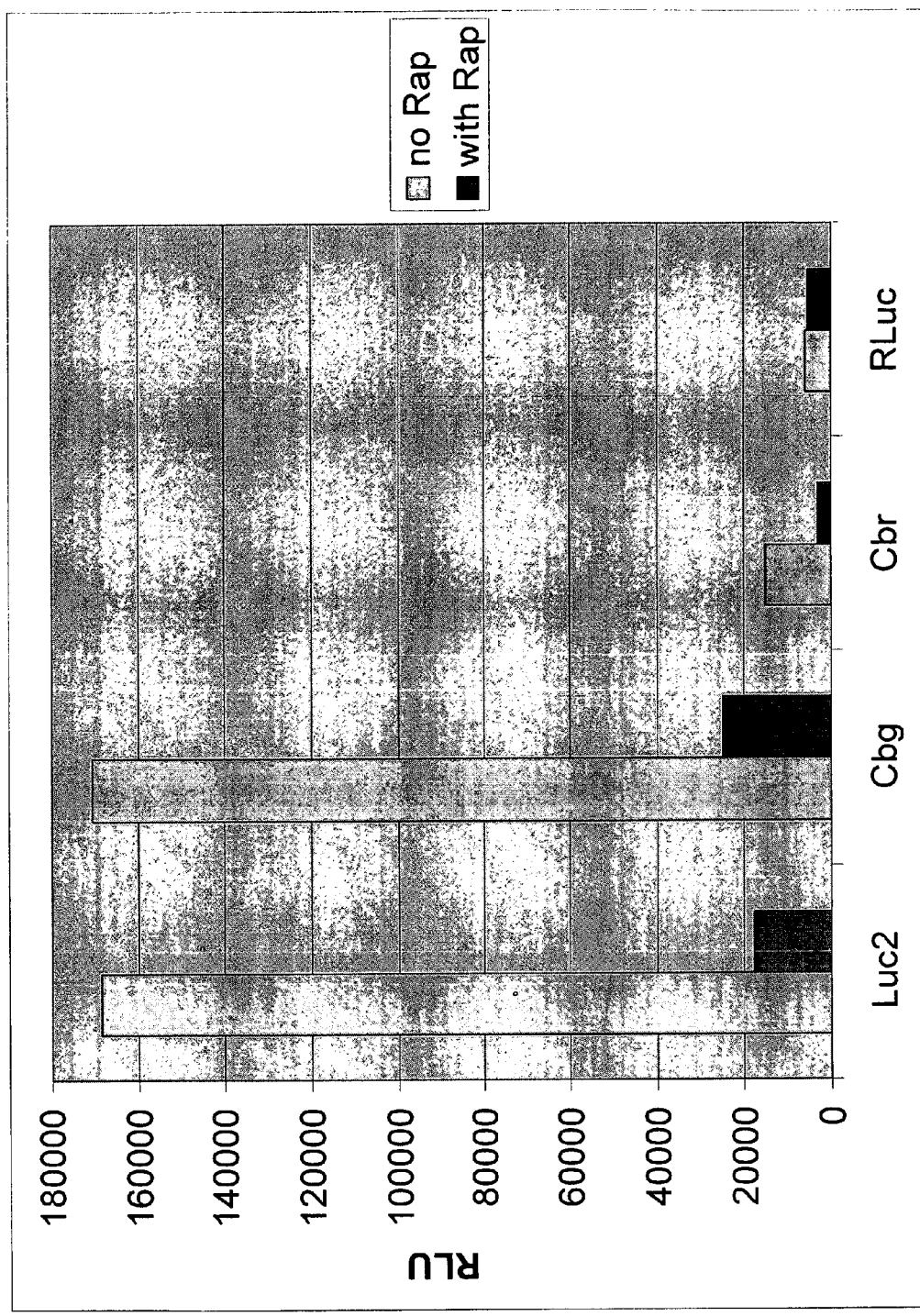
FIG. 21B. Luciferase activity of FRB and FKBP fusions with firefly luciferase, click beetle luciferases and Renilla luciferase, in the presence or absence of rapamycin.

As seen in FIG. 21B, both green and red click beetle double fusions showed the same relative effect when rapamycin was present when compared to the control (Luc2); luminescence decreased in response to rapamycin, whereas the *Renilla* luciferase did not respond to rapamycin.

C. In Vivo Demonstration of a Luciferase Modulator System

Using pJLC 68 from Example X.A as a template, the fragment for the N-terminal fusion of FRB with luciferase (FRB-Luc2), C-terminal fusion of luciferase with FKBP (Luc2-FKBP), or double fusion (FRB-Luc2-FKBP) were amplified following the PCR program of 95° C. for 2 minutes followed by 25 cycles of 95° C. for 30 seconds, 50° C. for 30 seconds and 72° C. for 2 minutes, with a final extension of 72° C. for 10 minutes. All forward primers for amplification were engineered to contain a NheI restriction endonuclease on the 5' end of the primer and all reverse primers were engineered to contain a BamHI restriction endocuclease site on the 5' end of the primer, thereby creating amplification fragments flanked on the 5' end by a NheI site and a BamHI site of the 3' end for cloning into the pBIND vector. Primers for amplification are as follows:

```
Luc2:
Forward Primer:
                                          (SEQ ID NO: 77)
ATGCGCTAGCCCGGGATATCGCCACCATGGATATCGCCAAAAAC

ATTAAG

Reverse Primer:
                                          (SEQ ID NO: 78)
GCATGGATCCTTATACGTAGATCTTGCCG FRB-Luc2:
Forward Primer:
                                          (SEQ ID NO: 79)
TGCGCTAGCCCGGGATATCGCCACCATGGTGGCCATCCTCTGGCA

TGAG

Reverse Primer:
                                          (SEQ ID NO: 80)
GCATGGATCCTTATACGTAGATCTTGCCG Luc 2-FKBP:
Forward Primer:
                                          (SEQ ID NO: 81)
ATGCGCTAGCCCGGGATATCGCCACCATGGATATCGCCAAAAAC

ATTAAG

Reverse Primer:
                                          (SEQ ID NO: 82)
GCATGGATCCTTATCATTCCAGTTTTAGAAGCTCCACATC FRP-Luc2-FKBP:
Forward Primer:
                                          (SEQ ID NO: 83)
TGCGCTAGCCCGGGATATCGCCACCATGGTGGCCATCCTCTGGCA

TGAG

Reverse Primer:
                                          (SEQ ID NO: 84)
GCATGGATCCTTATCATTCCAGTTTTAGAAGCTCCACATC
```

Figure 22:
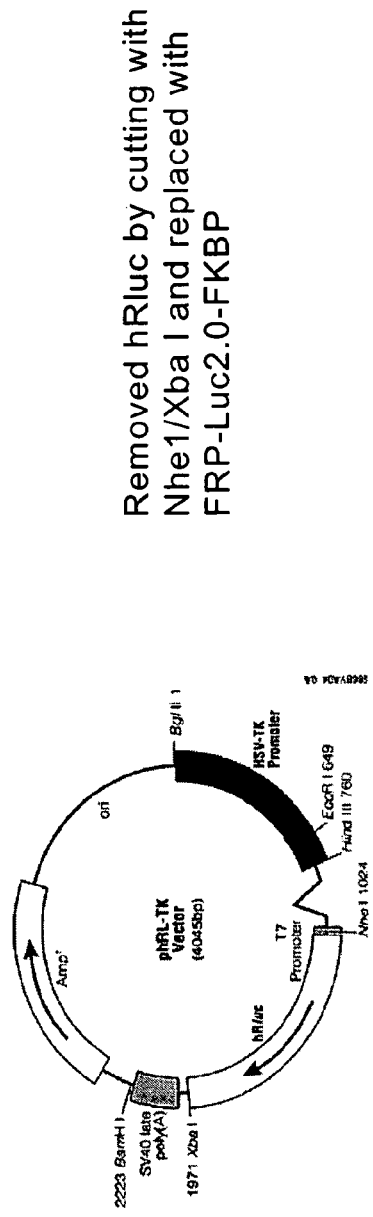
FIG. 22. Construct for expressing luciferase from a TK promoter.

Using the phRL-TK vector (Promega Corporation) as the source of the TK promoter and vector backbone (FIG. 22A), the *Renilla* luciferase found in the vector was removed and replaced with the FRB-Luc2-FKBP sequence amplified from the pBIND-FRB-Luc2-FKBP to generate a NheI restriction endonuclease on the 5' end of the fragment and a XbaI site on the 3' end of the fragment. The following primers generated the product for subsequent insertion into the phRL-TK vector using established molecular biological techniques (Sambrook et al., 1989).

```
TK FRP-Luc2-FKBP:
Forward Primer:
                                          (SEQ ID NO: 85)
TGCGCTAGCCCGGGATATCGCCACCATGGTGGCCATCCTCTGGCA

TGAG

Reverse Primer
                                          (SEQ ID NO: 86)
GCATTCTAGATTAATTCCAGTTTTAGAAGCTCC
```

The in vivo response of the FRB-FKBP interaction to rapamycin was studied using D293 cells (a subpopulation of the parent ATCC CRL-1573 HEK293 cells that were previously selected for their increased response to cAMP stimulation). For all in vivo experiments, D293 cells were seeded onto 96-well tissue culture plates at 5,000 cells/well prior to transfection and incubated at 37° C. and 10% $CO_2$ for at least 8 hours. The pBIND constructs and the TK double fusion construct were transfected into D293 cells using TransIT® LT1 Transfection Reagent (Mirus Corporation) as described in the protocol using 0.1 µg DNA/0.3 µl transfection reagent per/well of a 96-well plate. Approximately 24 hours after transfection (FIGS. 24-25), 10 µl of 50 mM of Luciferin EF (Promega Corporation, endotoxin free) was added to each well and cells were equilibrated for at least 15 minutes. An initial luminescent reading was measured from each sample (time point 0 minutes) and then 10 µl of a 0.2 µM rapamycin stock diluted in OptiMEM tissue culture media (Invitrogen) was added to the rapamycin tests wells, leaving control wells free of rapamycin. Plates were read following addition of rapamycin and approximately every 15 minutes after the addition of rapamycin up to one hour. For data shown in FIG. 24, FK506 was titered into reactions from 0-50 µM, and rapamycin was present at 1 µM. Luminescence was measured directly using the Veritas Luminometer.

Results

Figure 23:
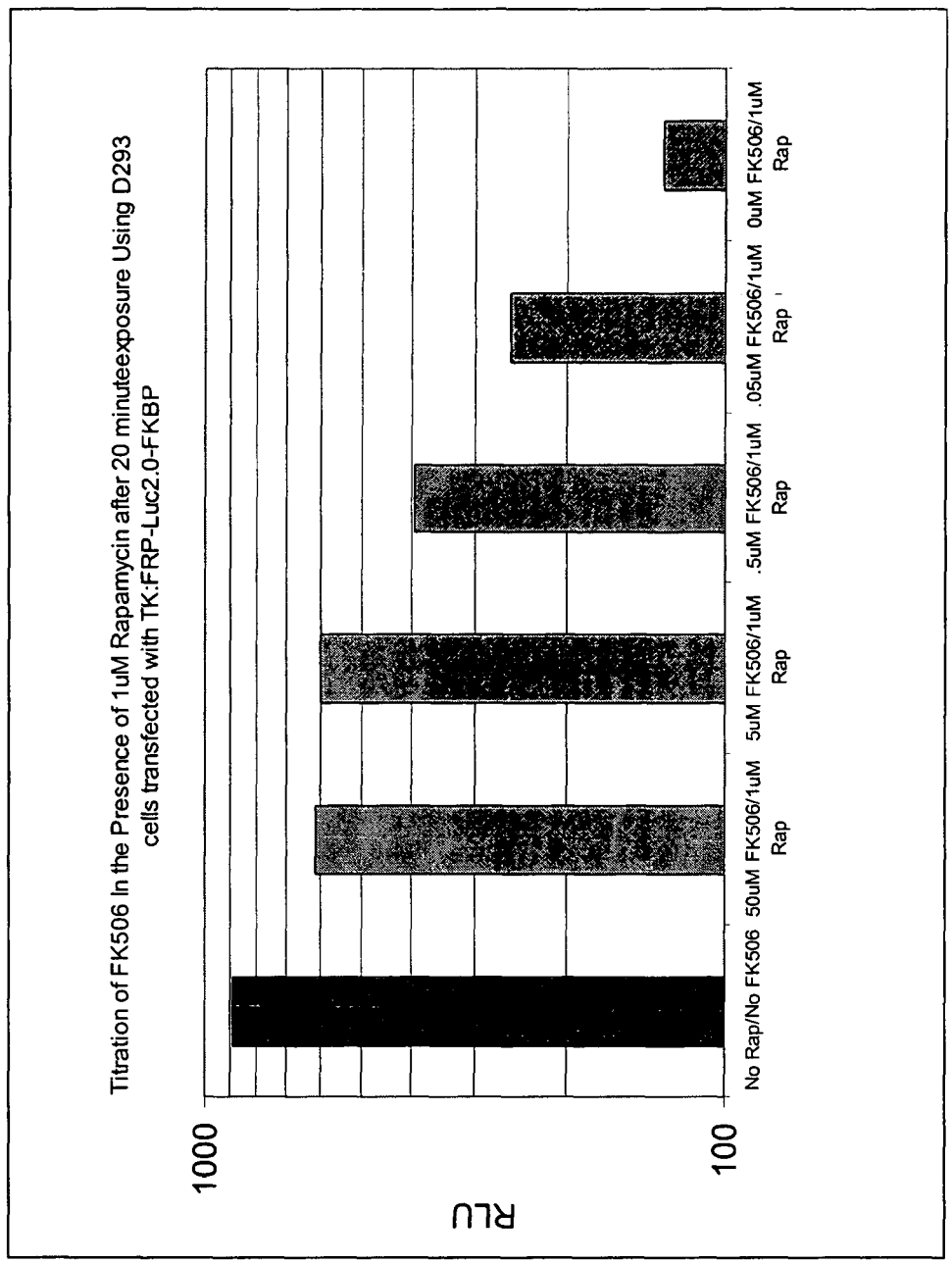
FIG. 23. Titration of FK506 in the presence of rapamycin in D293 cells transfected with luciferase fused to FRB and FKBP (FRB1-luc2-FKBP), demonstrating inhibition of rapamycin-mediated modulation by FK506.
Figure 24:
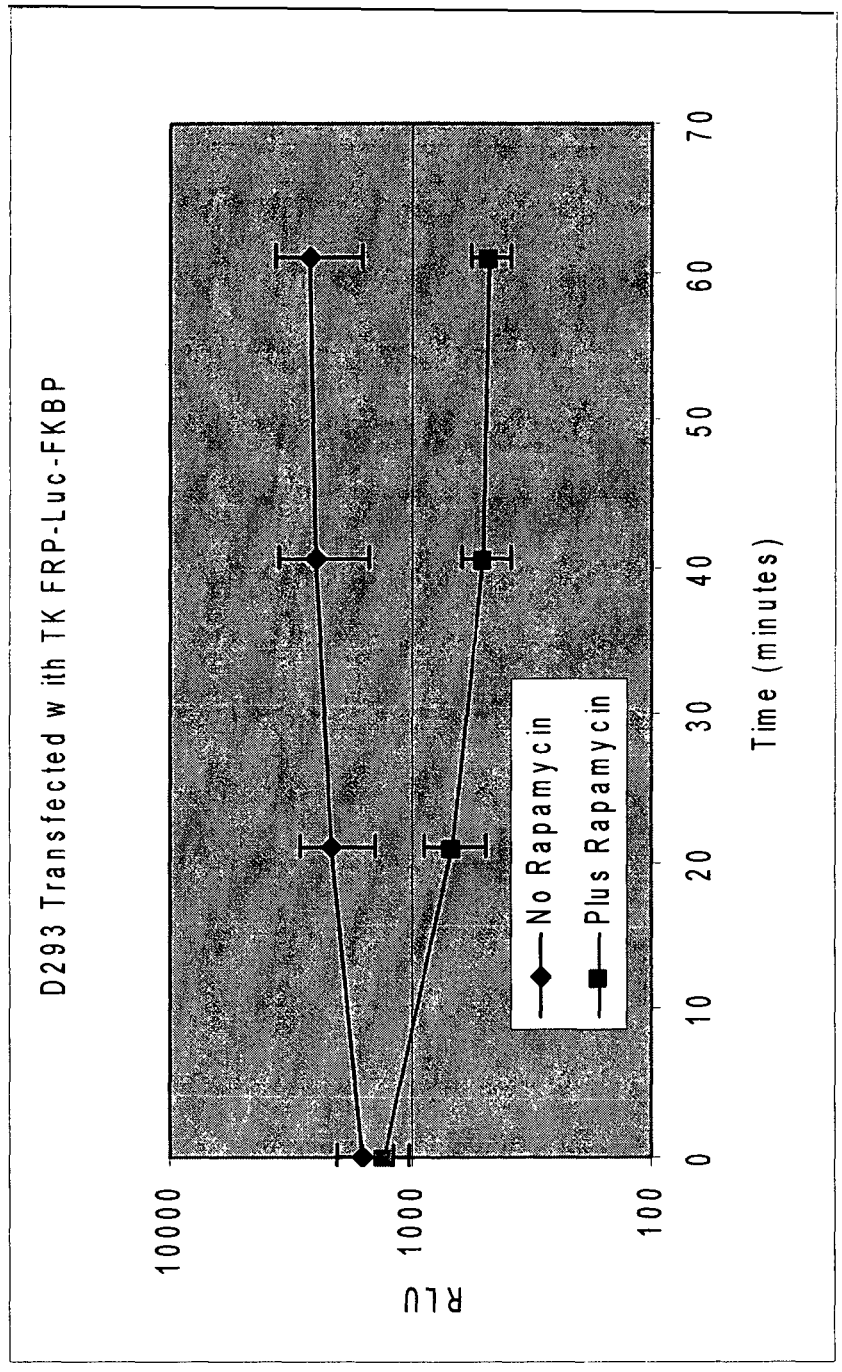
FIG. 24. Relative luminescence over time in D293 cells transfected with a construct with a TK promoter and a coding region for a FRB-luciferase-FKBP fusion, in the presence or absence of rapamycin.
Figure 25A:
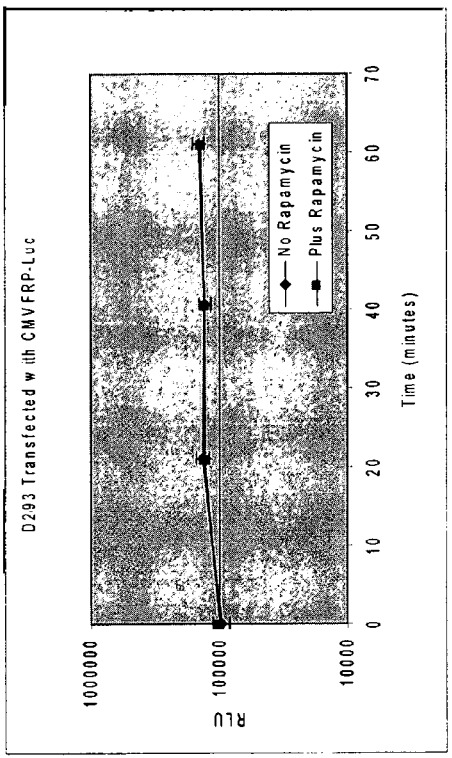
FIG. 25A-D. Relative luminescence over time in D293 cells transfected with a construct with a CMV promoter linked to a coding region for a FRB-luciferase-FKBP fusion (A), a FRB-luciferase fusion (B), luciferase (C), or a luciferase-FKBP fusion (D), in the presence or absence of rapamycin.
Figure 25B:
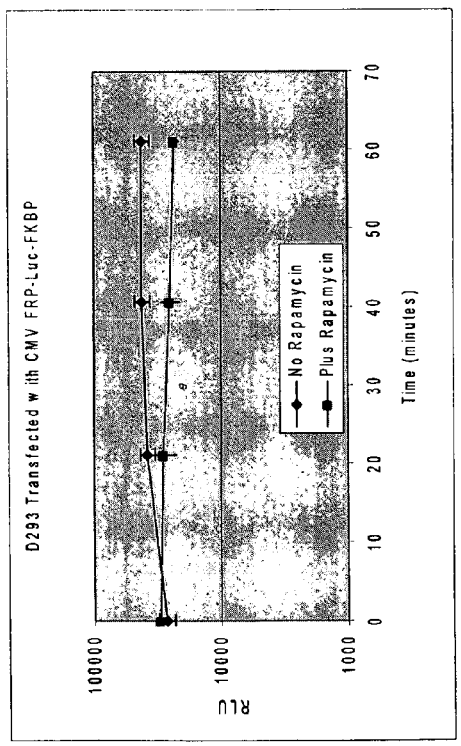
Figure 25C:
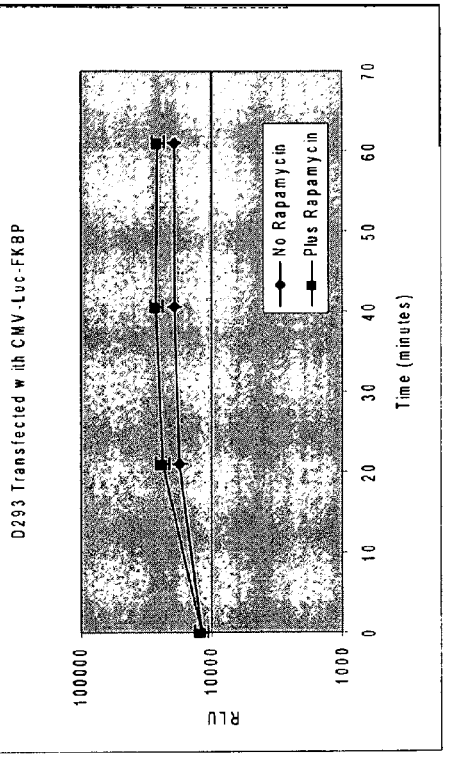
Figure 25D:
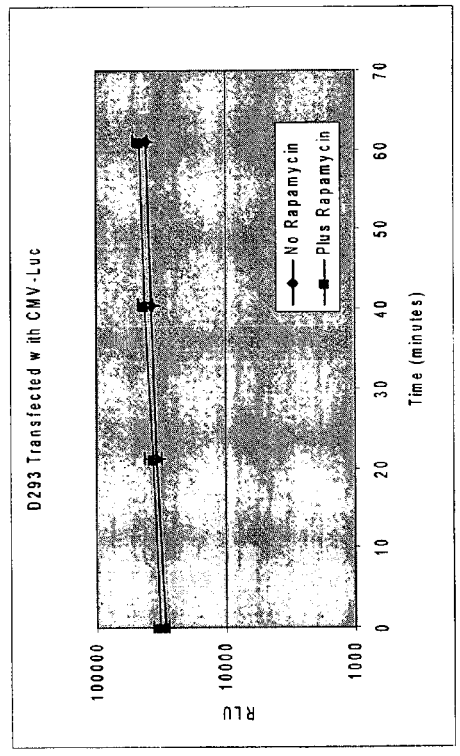
Figure 26:
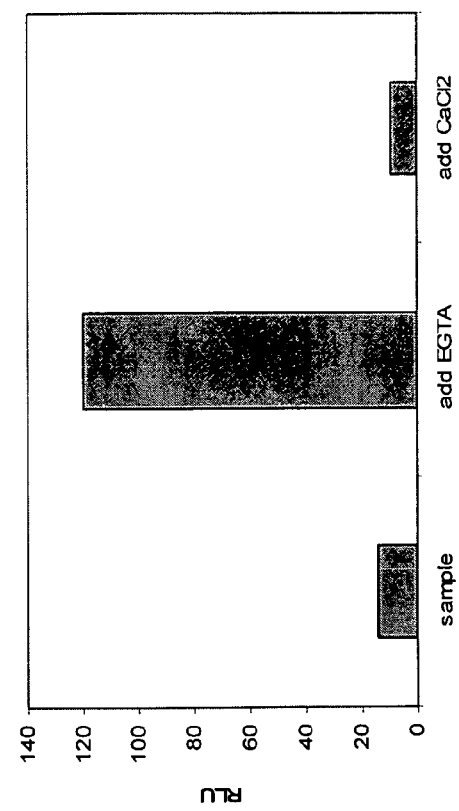
FIG. 26. Relative luminescence of a calmodulin-luciferase fusion in the presence of EGTA or $Ca^{2+}$.

Rapamycin-mediated modulation of FRB-luciferase-FKBP was observed in vivo (FIG. 23-25). Up to 5-fold and 2-fold decreases of luminescent signal were observed using the TK or CMV promoter systems, respectively. Control constructs did not show a response to rapamycin (FIGS. 25 B-D). Moreover, FK506, which competes with rapamycin for binding to FKBP, counteracts the effect of rapamycin in a titratable manner (FIG. 24).

EXAMPLE XI

In Vitro Experiments with a C-Terminal Modulated Luciferase Fusion System

In one embodiment, luciferase activity may be modulated by a fusion at either the N- or C-terminus of luciferase. For instance, a luciferase C-terminal fusion to calmodulin may be modulated by agents that modulate calmodulin.

Materials and Methods

The human calmodulin gene (CaM) was amplified from vector pOTB7 (ATCC® Global Resource Center, MGC-1447) using the forward primer 5'ATGCTACGTAGCTGAC-CAGCTGACTGAGGAGCAG3' (SEQ ID NO:87) and reverse primer 5'ATGCCTCGAGTCACTTTGCAGTCAT-CATCTGTAC3' (SEQ ID NO:88) following the program: 95° C. for 5 minutes followed by 20 cycles of 95° C. for 30 seconds, 60° C. for 30 seconds, 72° C. for 1 minute and 10 seconds. A SnaBI site was engineered onto the 5' end of the forward primer and a XhoI site was engineered onto the 5' end of the reverse primer. The CaM gene was cloned into the C-terminal end of the Luciferase T7 Control Vector with the Luc2 gene (as described above) on the SnaBI/XhoI sites, thereby creating the Luc2-CaM fusion construct. The fusion protein was expressed in vitro using the TnT® Coupled Reticulocyte Lysate System (Promega Corp.) according to the manufacturer's protocol. Luminescence was measured on a Turner 20/20 luminometer.

To assay modulation of the luciferase protein by the attached CaM protein, EGTA and $CaCl_2$ were sequentially added to the in vitro Luc2-CaM fusion protein lysate. Initially, 1 µl of the Luc2-CaM lysate from the TnT® reaction was added to 100 µl of Luciferase Assay Reagent (LAR, Promega Corp.) and 25 µl of the mixture was used to define baseline luminescence prior to addition of EGTA and $CaCl_2$. After initial luminescence was determined, 1 µl of a 75 mM EGTA solution (final concentration of 3 mM) was added to the lysate/LAR and luminescence was determined. Once luminescence in response to the addition of EGTA was determined, 1 µl of a 100 mM $CaCl_2$ solution was added to the lysate/LAR and luminescence was then determined. Therefore, there were three luminescent measurements of the Luc2-CaM fusion construct; 1) baseline, without addition of EGTA or $Ca^{+2}$, 2) after addition of EGTA, and 3) after addition of $Ca^{+2}$.

Results

The calmodulin protein undergoes large structural changes in response to calcium and thereby provides another possibility to modulate luciferase activity through a C-terminal fusion. Without the presence of either EGTA or $Ca^{+2}$, CaM limits the interaction between luciferase and its substrate (FIG. 27, "sample"). However, upon addition of EGTA this limitation is relieved (FIG. 27, "EGTA") and luminescence increases about 9-fold. This increase in luminescence can be reversed by the addition of $Ca^{+2}$ (FIG. 27, "$CaCl_2$"). Therefore, the conformation of CaM appeared to affect the luciferase activity in the Luc2-CaM fusion.

REFERENCES

Altschul et al., *J. Mol. Biol.*, 215:403 (1990).
Altschul et al., *Nuc. Acids Res.*, 25:3389 (1977).
Chong et al., *Gene*, 192:271 (1997).
Corpet et al., *Nucl. Acids Res.*, 16:1088 (1988).
Einbond et al., *FEBS Lett.*, 384:1 (1996).
Geysen et al., *Proc. Natl. Acad. Sci. USA*, 3998 (1984).
Hanks and Hunter, *FASEB J*, 9:576-595 (1995).
Henikoff & Henikoff, *Proc. Natl. Acad. Sci. USA*, 89:10915 (1989).
Higgins et al., *Gene*, 73:237 (1988).
Higgins et al., *LABIOS*, 5:157 (1989).
Huang et al., *LABIOS*, 8:155 (1992).
Ilsley et al., *Cell Signaling*, 14:183 (2002).
Karlin & Altschul, *Proc. Natl. Acad. Sci. USA*, 90:5873 (1993).
Lee et al., *Anal. Biochem.*, 316:162 (2003).
Liu et al., *Gene*, 237:153 (1999).
Mayer and Baltimore, *Trends Cell. Biol.*, 3:8 (1993).
Merrifield, *J. Am. Chem. Soc.*, 2149 (1963).
Mils et al., *Oncogene*, 19:1257 (2000).
Myers and Miller, *LABIOS*, 4:11 (1988).
Ozawa et al, *Analytical Chemistry*, 73:2516 (2001).
Paulmurugan et al., *PNAS*, 24:15603 (1999).
Pearson et al., *Methods Mol. Biol.*, 24:307 (1994).
Plainkum et al., *Nat. Struct. Biol.*, 10:115 (2003).
Sadowski, et al., *Mol. Cell. Bio.*, 6:4396 (1986).
Sadowski et al., *Nature*, 335:563 (1988).
Sala-Newby et al., *Biochem J.*, 279:727 (1991).
Sala-Newby et al., *FEBS*, 307:241 (1992).
Sambrook et al., In: *Molecular Cloning: A Laboratory Manual*, Cold Spring Harbor (1989).
Stewart et al., Solid Phase Peptide Synthesis, 2 ed., Pierce Chemical Co., Rockford, Ill., pp. 11-12).
Wang et al., *BBRC*, 282:28 (2001).
Waud et al, *BBA*, 1292:89 (1996).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

The invention claimed is:

1. A method to detect a molecule of interest in a cell, comprising:
   a) contacting a cell with a polynucleotide encoding a modified beetle luciferase, wherein the modified beetle luciferase comprises an internal insertion of a heterologous amino acid sequence which interacts with a molecule of interest, which insertion is at a residue or in a region in a beetle luciferase sequence which is tolerant to modification, wherein activity of the modified beetle luciferase is altered after the molecule of interest interacts with the insertion sequence relative to the activity before the interaction, wherein the modified beetle luciferase is a firefly or click beetle luciferase, wherein if the modified beetle luciferase is a firefly luciferase, the insertion is in a region corresponding to residue 116 to 126, residue 228 to 238, residue 262 to 272, residue 289 to 308, residue 356 to 366, or residue 535 to 546 of a firefly luciferase, and wherein if the modified beetle luciferase is a click beetle luciferase, the insertion is in a region corresponding to residue 15 to 30, residue 112 to 122, residue 352 to 362, residue 371 to 384, residue 393 to 414, or residue 485 to 495 of a click beetle luciferase; and
   b) detecting the activity of the modified beetle luciferase encoded by the polynucleotide, thereby detecting the presence of the molecule in the cell.

2. The method of claim 1, wherein the modified beetle luciferase further comprises a deletion of beetle luciferase sequences N-terminal and/or C-terminal to the insertion.

3. The method of claim 1, wherein the modified beetle luciferase further comprises a deletion of beetle luciferase sequences at sequences corresponding to the N-terminus and/or C-terminus of the unmodified beetle luciferase.

4. The method of claim 1, wherein the insertion is about 4 to about 50 amino acid residues.

5. The method of claim 1, wherein the insertion is in a hinge region of the luciferase.

6. The method of claim 1, wherein detecting the activity of the modified beetle luciferase further comprises determining the amount of the molecule in the cell.

7. A method to identify a moiety which interacts with a modified beetle luciferase, comprising:
   a) contacting a modified beetle luciferase with a library of compounds, wherein the modified beetle luciferase comprises an internal insertion of a heterologous amino acid sequence, which insertion is at a residue or in a region which is tolerant to modification, and wherein the activity of the modified beetle luciferase is detectable, wherein the modified beetle luciferase is a firefly or click beetle luciferase, wherein if the modified beetle luciferase is a firefly luciferase, the insertion is in a region corresponding to residue 116 to 126, residue 228 to 238, residue 262 to 272, residue 289 to 308, residue 356 to 366, or residue 535 to 546 of firefly luciferase, and wherein if the modified beetle luciferase is a click beetle luciferase, the insertion is in a region corresponding to residue 15 to 30, residue 112 to 122, residue 352 to 362, residue 371 to 384, residue 393 to 414, or residue 485 to 495 of click beetle luciferase; and
   b) identifying whether one or more compounds interact with the modified beetle luciferase relative to the unmodified beetle luciferase.

8. A method to identify a compound which interacts with a heterologous sequence in a modified beetle luciferase, comprising:
   a) contacting a modified beetle luciferase with one or more compounds, wherein the modified beetle luciferase comprises a first heterologous sequence comprising a domain at the N-terminus or the C-terminus of a fragment of a beetle luciferase having at least 10% the activity of a corresponding full-length functional beetle luciferase, wherein the domain noncovalently interacts with an exogenous agent, which interaction detectably alters luminescence of the modified beetle luciferase, wherein the heterologous sequence does not include a domain from the estrogen receptor, and wherein the interaction does not result in protein complementation or protein splicing, wherein the modified beetle luciferase is a firefly or click beetle luciferase; and
   b) detecting luminescence, thereby identifying whether one or more compounds alters the activity of the modified beetle luciferase.

9. A method to identify a compound which interacts with a heterologous sequence in a modified beetle luciferase, comprising:
   a) contacting the modified beetle luciferase with one or more compounds, wherein the modified beetle luciferase comprises a first heterologous sequence comprising a domain at the N-terminus and a second heterologous sequence comprising a domain at the C-terminus, wherein the domains of the first and second heterologous sequences noncovalently interact, wherein the noncovalent interaction detectably alters luminescence of the modified beetle luciferase, and wherein the noncovalent interaction is modulatable, wherein the modified beetle luciferase is a firefly or click beetle luciferase; and
   b) detecting luminescence, thereby identifying whether one or more compounds alters the activity of the modified beetle luciferase.

10. A method to detect in a sample the presence or amount of an exogenous agent which alters a noncovalent interaction, comprising:
    a) contacting the sample with a modified beetle luciferase, wherein the modified beetle luciferase comprises a first heterologous sequence comprising a domain at the N terminus and a second heterologous sequence comprising a domain at the C-terminus, wherein the domains of the first and second heterologous sequences noncovalently interact, wherein the noncovalent interaction detectably alters luminescence of the modified beetle luciferase, and wherein the noncovalent interaction is modulatable, wherein the modified beetle luciferase is a firefly or click beetle luciferase; and
    b) detecting luminescence, thereby detecting the presence of the exogenous agent in the sample.

11. The method of claim 10, wherein the modified beetle luciferase lacks one or more amino acids present at the N-terminus and/or C-terminus of the corresponding unmodified beetle luciferase.

12. The method of claim 10, wherein the noncovalent interaction is altered in the presence of a first exogenous agent.

13. The method of claim 12, wherein the alteration of the noncovalent interaction is inhibited by a second exogenous agent.

14. The method of claim 10, wherein each heterologous sequence has a different domain.

15. The method of claim 10, wherein each heterologous sequence has the same domain.

16. The method of claim 10, wherein the noncovalent interaction inhibits luminescence.

17. The method of claim 10, wherein detecting the luminescence further comprises determining the amount of the exogenous agent in the sample.

* * * * *

SEQUENCE LISTING

```
<160> NUMBER OF SEQ ID NOS: 118

<210> SEQ ID NO 1
<211> LENGTH: 5
<212> TYPE: PRT
<213> ORGANISM: Artificial Sequence
<220> FEATURE:
<223> OTHER INFORMATION: A synthetic affinity domain

<400> SEQUENCE: 1

His His His His His
1               5

<210> SEQ ID NO 2
```

```
<211> LENGTH: 6
<212> TYPE: PRT
<213> ORGANISM: Artificial Sequence
<220> FEATURE:
<223> OTHER INFORMATION: A synthetic affinity domain

<400> SEQUENCE: 2

His His His His His His
 1               5

<210> SEQ ID NO 3
<211> LENGTH: 10
<212> TYPE: PRT
<213> ORGANISM: Artificial Sequence
<220> FEATURE:
<223> OTHER INFORMATION: A synthetic affinity domain

<400> SEQUENCE: 3

Glu Gln Lys Leu Ile Ser Glu Glu Asp Leu
 1               5                  10

<210> SEQ ID NO 4
<211> LENGTH: 8
<212> TYPE: PRT
<213> ORGANISM: Artificial Sequence
<220> FEATURE:
<223> OTHER INFORMATION: A synthetic affinity domain

<400> SEQUENCE: 4

Asp Tyr Lys Asp Asp Asp Asp Lys
 1               5

<210> SEQ ID NO 5
<211> LENGTH: 8
<212> TYPE: PRT
<213> ORGANISM: Artificial Sequence
<220> FEATURE:
<223> OTHER INFORMATION: A synthetic affinity domain

<400> SEQUENCE: 5

Trp Ser His Pro Gln Phe Glu Lys
 1               5

<210> SEQ ID NO 6
<211> LENGTH: 9
<212> TYPE: PRT
<213> ORGANISM: Artificial Sequence
<220> FEATURE:
<223> OTHER INFORMATION: A synthetic affinity domain

<400> SEQUENCE: 6

Tyr Pro Tyr Asp Val Pro Asp Tyr Ala
 1               5

<210> SEQ ID NO 7
<211> LENGTH: 61
<212> TYPE: DNA
<213> ORGANISM: Artificial Sequence
<220> FEATURE:
<223> OTHER INFORMATION: A synthetic oligonucleotide

<400> SEQUENCE: 7
gaagggcgga aagatcgccg tggatgatga cgacaagatg aagacgcca aaaacataaa    60 g                                                                  61

<210> SEQ ID NO 8
<211> LENGTH: 17
```

```
<212> TYPE: PRT
<213> ORGANISM: Artificial Sequence
<220> FEATURE:
<223> OTHER INFORMATION: A synthetic affinity domain

<400> SEQUENCE: 8

Trp Glu Ala Ala Ala Arg Glu Ala Cys Cys Arg Glu Cys Cys Ala Arg
 1               5                  10                  15
Ala

<210> SEQ ID NO 9
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 9
ggctacgtaa acaatgtgga g                                          21

<210> SEQ ID NO 10
<211> LENGTH: 11
<212> TYPE: PRT
<213> ORGANISM: Artificial Sequence
<220> FEATURE:
<223> OTHER INFORMATION: A synthetic coronavirus protease site

<400> SEQUENCE: 10

Ser Thr Leu Gln Ser Gly Leu Arg Lys Met Ala
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: A synthetic HIV-1 protease site

<400> SEQUENCE: 11

Ser Gln Asn Tyr Pro Ile Val Gln
 1               5

<210> SEQ ID NO 12
<211> LENGTH: 10
<212> TYPE: PRT
<213> ORGANISM: Artificial Sequence
<220> FEATURE:
<223> OTHER INFORMATION: A synthetic HIV-1 protease site

<400> SEQUENCE: 12

Lys Ala Val Arg Leu Ala Glu Ala Met Ser
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: A synthetic HCV protease site

<400> SEQUENCE: 13

Ala Glu Asp Val Val Cys Cys Ser Met Ser Tyr Ser
 1               5                  10

<210> SEQ ID NO 14
<211> LENGTH: 7
<212> TYPE: PRT
```

```
<213> ORGANISM: Artificial Sequence
<220> FEATURE:
<223> OTHER INFORMATION: A synthetic  -secretase site for amyloid
      precursor protein

<400> SEQUENCE: 14

Val Lys Met Asp Ala Glu Phe
1               5

<210> SEQ ID NO 15

<400> SEQUENCE: 15

000

<210> SEQ ID NO 16
<211> LENGTH: 20
<212> TYPE: PRT
<213> ORGANISM: Artificial Sequence
<220> FEATURE:
<223> OTHER INFORMATION: A synthetic SARS virus protease site

<400> SEQUENCE: 16

Gln Thr Ser Ile Thr Ser Ala Val Leu Gln Ser Gly Phe Arg Lys Met
1               5                   10                  15

Ala Phe Pro Ser
            20

<210> SEQ ID NO 17
<211> LENGTH: 20
<212> TYPE: PRT
<213> ORGANISM: Artificial Sequence
<220> FEATURE:
<223> OTHER INFORMATION: A synthetic SARS virus protease site

<400> SEQUENCE: 17

Val Arg Gln Cys Ser Gly Val Thr Phe Gln Gly Lys Phe Lys Lys Ile
1               5                   10                  15

Val Lys Gly Thr
            20

<210> SEQ ID NO 18
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 18
gccactaaag aagcccgtcg acgatgatgg ctggctc                              37

<210> SEQ ID NO 19
<211> LENGTH: 10
<212> TYPE: PRT
<213> ORGANISM: Artificial Sequence
<220> FEATURE:
<223> OTHER INFORMATION: A synthetic SARS virus protease site

<400> SEQUENCE: 19

Thr Ser Ala Val Leu Gln Ser Gly Phe Arg
1               5                   10

<210> SEQ ID NO 20
<211> LENGTH: 65
<212> TYPE: DNA
<213> ORGANISM: Artificial Sequence
<220> FEATURE:
```

<223> OTHER INFORMATION: A synthetic linker

<400> SEQUENCE: 20

```
gagatcctca taaggccaag aagctcgaga tggttccatg ggccaaaaac ataaagaaag    60
gcccg                                                                65
```

<210> SEQ ID NO 21
<211> LENGTH: 12
<212> TYPE: PRT
<213> ORGANISM: Artificial Sequence
<220> FEATURE:
<223> OTHER INFORMATION: A synthetic peptide

<400> SEQUENCE: 21

Ala Asn Lys Ile Ser Tyr Gln Ser Ser Ser Thr Glu
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: A synthetic peptide

<400> SEQUENCE: 22

Ala Asn Lys Ala Ser Tyr Gln Ser Ala Ser Thr Glu
 1               5                  10

<210> SEQ ID NO 23
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 23

```
tcgaagctaa caaagcttcc taccagtctg cgtccaccga ac                       42
```

<210> SEQ ID NO 24
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 24

```
catggttcgg tggacgcaga ctggtaggaa gctttgttag ct                       42
```

<210> SEQ ID NO 25
<211> LENGTH: 8
<212> TYPE: PRT
<213> ORGANISM: Artificial Sequence
<220> FEATURE:
<223> OTHER INFORMATION: A synthetic peptide

<400> SEQUENCE: 25

Leu Glu Val Leu Phe Gln Gly Pro
 1               5

<210> SEQ ID NO 26
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 26
tcgagctgga agttctgttc cagggtccgg 30

<210> SEQ ID NO 27
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 27
catgccggac cctggaacag aacttccagc 30

<210> SEQ ID NO 28
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 28
agctaggatc cgatactgcg attttaagtg ttgttc 36

<210> SEQ ID NO 29
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 29
agctagaatt cttacggaat gatttgattg ccaaaaatag 40

<210> SEQ ID NO 30
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 30
gactagctag catggatact gcgattttaa gtgttgttc 39

<210> SEQ ID NO 31
<211> LENGTH: 49
<212> TYPE: DNA
<213> ORGANISM: Artificial Sequence
<220> FEATURE:
<223> OTHER INFORMATION: A synthetic primer

<400> SEQUENCE: 31
gtgaaccatc accatcacca tcacaatgtg gaggccacta aagaagccg 49

<210> SEQ ID NO 32
<211> LENGTH: 53
<212> TYPE: DNA
<213> ORGANISM: Artificial Sequence
<220> FEATURE:
<223> OTHER INFORMATION: A synthetic primer

<400> SEQUENCE: 32
tcgacggctt ctttagtggc ctccacattg tgatggtgat ggtgatggtt cac 53

<210> SEQ ID NO 33
<211> LENGTH: 55
<212> TYPE: DNA
<213> ORGANISM: Artificial Sequence
<220> FEATURE:
<223> OTHER INFORMATION: A synthetic primer

<400> SEQUENCE: 33
gtgaacgact ataaggacga cgacgacaag aatgtggagg ccactaaaga agccg        55

<210> SEQ ID NO 34
<211> LENGTH: 59
<212> TYPE: DNA
<213> ORGANISM: Artificial Sequence
<220> FEATURE:
<223> OTHER INFORMATION: A synthetic primer

<400> SEQUENCE: 34
tcgacggctt ctttagtggc ctccacattc ttgtcgtcgt cgtccttata gtcgttcac    59

<210> SEQ ID NO 35
<211> LENGTH: 43
<212> TYPE: DNA
<213> ORGANISM: Artificial Sequence
<220> FEATURE:
<223> OTHER INFORMATION: A synthetic primer

<400> SEQUENCE: 35
gtgaacgacg aggtcgacaa tgtggaggcc actaaagaag ccg                    43

<210> SEQ ID NO 36
<211> LENGTH: 47
<212> TYPE: DNA
<213> ORGANISM: Artificial Sequence
<220> FEATURE:
<223> OTHER INFORMATION: A synthetic primer

<400> SEQUENCE: 36
tcgacggctt ctttagtggc ctccacattg tcgacctcgt cgttcac                47

<210> SEQ ID NO 37
<211> LENGTH: 52
<212> TYPE: DNA
<213> ORGANISM: Artificial Sequence
<220> FEATURE:
<223> OTHER INFORMATION: A synthetic primer

<400> SEQUENCE: 37
gtgaacctgc gccgcgcctc cctgggtaat gtggaggcca ctaaagaagc cg          52

<210> SEQ ID NO 38
<211> LENGTH: 56
<212> TYPE: DNA
<213> ORGANISM: Artificial Sequence
<220> FEATURE:
<223> OTHER INFORMATION: A synthetic primer

<400> SEQUENCE: 38
tcgacggctt ctttagtggc ctccacatta cccagggagg cgcggcgcag gttcac      56

<210> SEQ ID NO 39
<211> LENGTH: 61
<212> TYPE: DNA
<213> ORGANISM: Artificial Sequence
<220> FEATURE:
<223> OTHER INFORMATION: A synthetic primer

<400> SEQUENCE: 39
gtaaacactt ctgctgttct gcagagtggt tttcgcaatg tggaggccac taaagaagcc  60
g                                                                 61

```
<210> SEQ ID NO 40
<211> LENGTH: 65
<212> TYPE: DNA
<213> ORGANISM: Artificial Sequence
<220> FEATURE:
<223> OTHER INFORMATION: A synthetic primer

<400> SEQUENCE: 40
tcgacggctt ctttagtggc ctccacattg cgaaaaccac tctgcagaac agcagaagtg    60
tttac                                                                65

<210> SEQ ID NO 41
<211> LENGTH: 61
<212> TYPE: DNA
<213> ORGANISM: Artificial Sequence
<220> FEATURE:
<223> OTHER INFORMATION: A synthetic primer

<400> SEQUENCE: 41
gtaaactctg gtgttacctt ccaaggtaag ttcaagaatg tggaggccac taaagaagcc    60
g                                                                    61

<210> SEQ ID NO 42
<211> LENGTH: 65
<212> TYPE: DNA
<213> ORGANISM: Artificial Sequence
<220> FEATURE:
<223> OTHER INFORMATION: A synthetic primer

<400> SEQUENCE: 42
tcgacggctt ctttagtggc ctccacattc ttgaacttac cttggaaggt aacaccagag    60
tttac                                                                65

<210> SEQ ID NO 43
<211> LENGTH: 34
<212> TYPE: DNA
<213> ORGANISM: Artificial Sequence
<220> FEATURE:
<223> OTHER INFORMATION: A synthetic primer

<400> SEQUENCE: 43
atgcgtcgac gtgaaacgcg aaaagaacgt gatc                                34

<210> SEQ ID NO 44
<211> LENGTH: 38
<212> TYPE: DNA
<213> ORGANISM: Artificial Sequence
<220> FEATURE:
<223> OTHER INFORMATION: A synthetic primer

<400> SEQUENCE: 44
atgcggatcc ttagttcacg tagcctttag agaccata                            38

<210> SEQ ID NO 45
<211> LENGTH: 38
<212> TYPE: DNA
<213> ORGANISM: Artificial Sequence
<220> FEATURE:
<223> OTHER INFORMATION: A synthetic primer

<400> SEQUENCE: 45
atgccatatg aatgtggagg ccactaaaga agccattg                            38
```

```
<210> SEQ ID NO 46
<211> LENGTH: 31
<212> TYPE: DNA
<213> ORGANISM: Artificial Sequence
<220> FEATURE:
<223> OTHER INFORMATION: A synthetic primer

<400> SEQUENCE: 46
agtctacgta gccgccagct ttttcgagga g                           31

<210> SEQ ID NO 47
<211> LENGTH: 34
<212> TYPE: DNA
<213> ORGANISM: Artificial Sequence
<220> FEATURE:
<223> OTHER INFORMATION: A synthetic primer

<400> SEQUENCE: 47
atgcgtcgac gtgaaacgcg aaaagaacgt gatc                        34

<210> SEQ ID NO 48
<211> LENGTH: 37
<212> TYPE: DNA
<213> ORGANISM: Artificial Sequence
<220> FEATURE:
<223> OTHER INFORMATION: A synthetic primer

<400> SEQUENCE: 48
atgcggatcc ttaagggtcg agagcgtgga tcaaacg                     37

<210> SEQ ID NO 49
<211> LENGTH: 33
<212> TYPE: DNA
<213> ORGANISM: Artificial Sequence
<220> FEATURE:
<223> OTHER INFORMATION: A synthetic primer

<400> SEQUENCE: 49
atgccatatg cgtgtgggta ctcaattgat ccc                         33

<210> SEQ ID NO 50
<211> LENGTH: 31
<212> TYPE: DNA
<213> ORGANISM: Artificial Sequence
<220> FEATURE:
<223> OTHER INFORMATION: A synthetic primer

<400> SEQUENCE: 50
agtctacgta gccgccagct ttttcgagga g                           31

<210> SEQ ID NO 51
<211> LENGTH: 51
<212> TYPE: DNA
<213> ORGANISM: Artificial Sequence
<220> FEATURE:
<223> OTHER INFORMATION: A synthetic primer

<400> SEQUENCE: 51
tcgaatccat cacctctgct gttctgcagt ccggtttccg taaaatggct c      51

<210> SEQ ID NO 52
<211> LENGTH: 51
<212> TYPE: DNA
<213> ORGANISM: Artificial Sequence
<220> FEATURE:
<223> OTHER INFORMATION: A synthetic primer

<400> SEQUENCE: 52
```

```
catggagcca ttttacggaa accggactgc agaacagcag aggtgatgga t          51
```

<210> SEQ ID NO 53
<211> LENGTH: 15
<212> TYPE: PRT
<213> ORGANISM: SARS virus

<400> SEQUENCE: 53

Ser Ile Thr Ser Ala Val Leu Gln Ser Gly Phe Arg Lys Met Ala
1 5 10 15

<210> SEQ ID NO 54
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 54
atgcatatca tatggcttcc aaggtgtacg acccc 35

<210> SEQ ID NO 55
<211> LENGTH: 80
<212> TYPE: DNA
<213> ORGANISM: Artificial Sequence
<220> FEATURE:
<223> OTHER INFORMATION: A synthetic oligonucleotide

<400> SEQUENCE: 55
atgcattaat gccaccggaa ccgccgccac cgctaccgcc gccaccgctg ccctgctcgt 60
tcttcagcac gcgctccacg 80

<210> SEQ ID NO 56
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 56
atgcatatca tatggtgaaa cgcgaaaaga acgt 34

<210> SEQ ID NO 57
<211> LENGTH: 79
<212> TYPE: DNA
<213> ORGANISM: Artificial Sequence
<220> FEATURE:
<223> OTHER INFORMATION: A synthetic oligonucleotide

<400> SEQUENCE: 57
atgcattaat gccaccggaa ccgccgccac cgctaccgcc gccaccgctg ccgccagctt 60
tttcgaggag ttgcttcag 79

<210> SEQ ID NO 58
<211> LENGTH: 9
<212> TYPE: PRT
<213> ORGANISM: Artificial Sequence
<220> FEATURE:
<223> OTHER INFORMATION: A synthetic peptide

<400> SEQUENCE: 58

Asp Asp Asp Asp Lys Gly Gly Asp Ile
1 5

<210> SEQ ID NO 59

<400> SEQUENCE: 59

000

<210> SEQ ID NO 60
<211> LENGTH: 51
<212> TYPE: DNA
<213> ORGANISM: Artificial Sequence
<220> FEATURE:
<223> OTHER INFORMATION: A synthetic primer

<400> SEQUENCE: 60
atgcgctagc ccggggatat cgccaccatg aagacgcca aaacataaa g        51

<210> SEQ ID NO 61
<211> LENGTH: 40
<212> TYPE: DNA
<213> ORGANISM: Artificial Sequence
<220> FEATURE:
<223> OTHER INFORMATION: A synthetic primer

<400> SEQUENCE: 61
gataaaaacc gttagtttag taaggcattc ctaggatcga        40

<210> SEQ ID NO 62
<211> LENGTH: 45
<212> TYPE: DNA
<213> ORGANISM: Artificial Sequence
<220> FEATURE:
<223> OTHER INFORMATION: A synthetic primer

<400> SEQUENCE: 62
atgcgctagc ccgggatatc gccaccatgg atactgcgat tttaa        45

<210> SEQ ID NO 63
<211> LENGTH: 44
<212> TYPE: DNA
<213> ORGANISM: Artificial Sequence
<220> FEATURE:
<223> OTHER INFORMATION: A synthetic primer

<400> SEQUENCE: 63
ttggcgcgcc ggatccttac acggcgatct ttccgcccctt cttg        44

<210> SEQ ID NO 64
<211> LENGTH: 45
<212> TYPE: DNA
<213> ORGANISM: Artificial Sequence
<220> FEATURE:
<223> OTHER INFORMATION: A synthetic primer

<400> SEQUENCE: 64
atgcgctagc ccgggatatc gccaccatgg aagacgccaa aaaca        45

<210> SEQ ID NO 65
<211> LENGTH: 44
<212> TYPE: DNA
<213> ORGANISM: Artificial Sequence
<220> FEATURE:
<223> OTHER INFORMATION: A synthetic primer

<400> SEQUENCE: 65
ttggcgcgcc ggatccttac acggcgatct ttccgcccctt cttg        44

<210> SEQ ID NO 66

<211> LENGTH: 1672
<212> TYPE: DNA
<213> ORGANISM: Artificial Sequence
<220> FEATURE:
<223> OTHER INFORMATION: A synthetic human codon optimized firefly luciferase gene (luc2.0)

<400> SEQUENCE: 66

| | | | | | |
|---|---|---|---|---|---|
| aaagccacca | tggaagatgc | caaaaacatt | aagaagggcc | cagcgccatt | ctacccactc | 60 |
| gaagacggga | ccgccggcga | gcagctgcac | aaagccatga | agcgctacgc | cctggtgccc | 120 |
| ggcaccatcg | cctttaccga | cgcacatatc | gaggtggaca | ttacctacgc | cgagtacttc | 180 |
| gagatgagcg | ttcggctggc | agaagctatg | aagcgctatg | ggctgaatac | aaaccatcgg | 240 |
| atcgtggtgt | gcagcgagaa | tagcttgcag | ttcttcatgc | ccgtgttggg | tgccctgttc | 300 |
| atcggtgtgg | ctgtggcccc | agctaacgac | atctacaacg | agcgcgagct | gctgaacagc | 360 |
| atgggcatca | gccagcccac | cgtcgtattc | gtgagcaaga | aagggctgca | aaagatcctc | 420 |
| aacgtgcaaa | agaagctacc | gatcatacaa | agatcatca | tcatggatag | caagaccgac | 480 |
| taccagggct | tccaaagcat | gtacaccttc | gtgacttccc | atttgccacc | cggcttcaac | 540 |
| gagtacgact | tcgtgcccga | gagcttcgac | cgggacaaaa | ccatcgccct | gatcatgaac | 600 |
| agtagtggca | gtaccggatt | gcccaagggc | gtagccctac | cgcaccgcac | cgcttgtgtc | 660 |
| cgattcagtc | atgcccgcga | ccccatcttc | ggcaaccaga | tcatccccga | caccgctatc | 720 |
| ctcagcgtgg | tgccatttca | ccacggcttc | ggcatgttca | ccacgctggg | ctacttgatc | 780 |
| tgcggctttc | gggtcgtgct | catgtaccgc | ttcgaggagg | agctattctt | gcgcagcttg | 840 |
| caagactata | agattcaatc | tgccctgctg | gtgcccacac | tatttagctt | cttcgctaag | 900 |
| agcactctca | tcgacaagta | cgacctaagc | aacttgcacg | agatcgccag | cggcggggcg | 960 |
| ccgctcagca | aggaggtagg | tgaggccgtg | gccaaacgct | tccacctacc | aggcatccgc | 1020 |
| cagggctacg | gcctgacaga | aacaaccagc | gccattctga | tcacccccga | aggggacgac | 1080 |
| aagcctggcg | cagtaggcaa | ggtggtgccc | ttcttcgagg | ctaaggtggt | ggacttggac | 1140 |
| accggtaaga | cactgggtgt | gaaccagcgc | ggcgagctgt | gcgtccgtgg | ccccatgatc | 1200 |
| atgagcggct | acgttaacaa | ccccgaggct | acaaacgctc | tcatcgacaa | ggacggctgg | 1260 |
| ctgcacagcg | gcgacatcgc | ctactgggac | gaggacgagc | acttcttcat | cgtggaccgg | 1320 |
| ctgaagagcc | tgatcaaata | caagggctac | caggtagccc | cagccgaact | ggagagcatc | 1380 |
| ctgctgcaac | accccaacat | cttcgacgcc | ggggtcgccg | gcctgcccga | cgacgatgcc | 1440 |
| ggcgagctgc | ccgccgcagt | cgtcgtgctg | aacacggta | aaaccatgac | cgagaaggag | 1500 |
| atcgtggact | atgtggccag | ccaggttaca | accgccaaga | agctgcgcgg | tggtgttgtg | 1560 |
| ttcgtggacg | aggtgcctaa | aggactgacc | ggcaagttgg | acgcccgcaa | gatccgcgag | 1620 |
| attctcatta | aggccaagaa | gggcggcaag | atcgccgtgt | aataattcta | ga | 1672 |

<210> SEQ ID NO 67
<211> LENGTH: 64
<212> TYPE: DNA
<213> ORGANISM: Artificial Sequence
<220> FEATURE:
<223> OTHER INFORMATION: A synthetic primer

<400> SEQUENCE: 67

| | | | | | |
|---|---|---|---|---|---|
| atgcaagctt | ggatccgttt | aaacgccacc | atggatatcg | ccaaaaacat | taagaagggc | 60 |
| ccag | | | | | | 64 |

```
<210> SEQ ID NO 68
<211> LENGTH: 45
<212> TYPE: DNA
<213> ORGANISM: Artificial Sequence
<220> FEATURE:
<223> OTHER INFORMATION: A synthetic primer

<400> SEQUENCE: 68
gagctcgcgg ccgcctcgag ttatacgtag atcttgccgc ccttc          45

<210> SEQ ID NO 69
<211> LENGTH: 302
<212> TYPE: DNA
<213> ORGANISM: Artificial Sequence
<220> FEATURE:
<223> OTHER INFORMATION: A synthetic gene for FRB1

<400> SEQUENCE: 69
ccatggtggc catcctctgg catgagatgt ggcatgaagg cctggaagag gcatctcgtt    60
tgtactttgg ggaaaggaac gtgaaaggca tgtttgaggt gctggagccc ttgcatgcta   120
tgatggaacg gggcccccag actctgaagg aaacatcctt taatcaggcc tatggtcgag   180
atttaatgga ggcccaagag tggtgcagga agtacatgaa atcagggaat gtcaaggacc   240
tcacccaagc ctgggacctc tattatcatg tgttccgacg aatctcaggt ggcggagata   300
tc                                                                  302

<210> SEQ ID NO 70
<211> LENGTH: 347
<212> TYPE: DNA
<213> ORGANISM: Artificial Sequence
<220> FEATURE:
<223> OTHER INFORMATION: A synthetic gene for FKBP

<400> SEQUENCE: 70
tacgtaggtg gagtgcaggt ggaaaccatc tccccaggag acgggcgcac cttccccaag    60
cgcggccaga cctgcgtggt gcactacacc gggatgcttg aagatggaaa gaaatttgat   120
tcctcccggg acagaaacaa gccctttaag tttatgctag caagcagga ggtgatccga    180 ggctgggaag aaggggttgc ccagatgagt gtgggtcaga gagccaaact gactatatct   240
ccagattatg cctatggtgc cactgggcac ccaggcatca tcccaccaca tgccactctc   300
gtcttcgatg tggagcttct aaaactggaa tgactcgagg cggccgc              347

<210> SEQ ID NO 71
<211> LENGTH: 29
<212> TYPE: DNA
<213> ORGANISM: Artificial Sequence
<220> FEATURE:
<223> OTHER INFORMATION: A synthetic primer

<400> SEQUENCE: 71
atgcgatatc gtgaaacgcg aaaagaacg                                      29

<210> SEQ ID NO 72
<211> LENGTH: 30
<212> TYPE: DNA
<213> ORGANISM: Artificial Sequence
<220> FEATURE:
<223> OTHER INFORMATION: A synthetic primer

<400> SEQUENCE: 72
gcatagatct taccgccggc cttcaccaac                                     30
```

```
<210> SEQ ID NO 73
<211> LENGTH: 29
<212> TYPE: DNA
<213> ORGANISM: Artificial Sequence
<220> FEATURE:
<223> OTHER INFORMATION: A synthetic primer

<400> SEQUENCE: 73
atgcgatatc gtgaaacgcg aaaagaacg                                     29

<210> SEQ ID NO 74
<211> LENGTH: 35
<212> TYPE: DNA
<213> ORGANISM: Artificial Sequence
<220> FEATURE:
<223> OTHER INFORMATION: A synthetic primer

<400> SEQUENCE: 74
gcatagatct tgccgccagc tttttcgagg agttg                              35

<210> SEQ ID NO 75
<211> LENGTH: 32
<212> TYPE: DNA
<213> ORGANISM: Artificial Sequence
<220> FEATURE:
<223> OTHER INFORMATION: A synthetic primer

<400> SEQUENCE: 75
atgctacgta gcttccaagg tgtacgaccc cg                                 32

<210> SEQ ID NO 76
<211> LENGTH: 32
<212> TYPE: DNA
<213> ORGANISM: Artificial Sequence
<220> FEATURE:
<223> OTHER INFORMATION: A synthetic primer

<400> SEQUENCE: 76
gcatagatct tctgctcgtt cttcagcacg cg                                 32

<210> SEQ ID NO 77
<211> LENGTH: 50
<212> TYPE: DNA
<213> ORGANISM: Artificial Sequence
<220> FEATURE:
<223> OTHER INFORMATION: A synthetic primer

<400> SEQUENCE: 77
atgcgctagc ccgggatatc gccaccatgg atatcgccaa aaacattaag              50

<210> SEQ ID NO 78
<211> LENGTH: 29
<212> TYPE: DNA
<213> ORGANISM: Artificial Sequence
<220> FEATURE:
<223> OTHER INFORMATION: A synthetic primer

<400> SEQUENCE: 78
gcatggatcc ttatacgtag atcttgccg                                     29

<210> SEQ ID NO 79
<211> LENGTH: 49
<212> TYPE: DNA
<213> ORGANISM: Artificial Sequence
<220> FEATURE:
<223> OTHER INFORMATION: A synthetic primer

<400> SEQUENCE: 79
```
tgcgctagcc cgggatatcg ccaccatggt ggccatcctc tggcatgag         49

<210> SEQ ID NO 80
<211> LENGTH: 29
<212> TYPE: DNA
<213> ORGANISM: Artificial Sequence
<220> FEATURE:
<223> OTHER INFORMATION: A synthetic primer

<400> SEQUENCE: 80
gcatggatcc ttatacgtag atcttgccg                              29

<210> SEQ ID NO 81
<211> LENGTH: 50
<212> TYPE: DNA
<213> ORGANISM: Artificial Sequence
<220> FEATURE:
<223> OTHER INFORMATION: A synthetic primer

<400> SEQUENCE: 81
atgcgctagc ccgggatatc gccaccatgg atatcgccaa aaacattaag        50

<210> SEQ ID NO 82
<211> LENGTH: 40
<212> TYPE: DNA
<213> ORGANISM: Artificial Sequence
<220> FEATURE:
<223> OTHER INFORMATION: A synthetic primer

<400> SEQUENCE: 82
gcatggatcc ttatcattcc agttttagaa gctccacatc                   40

<210> SEQ ID NO 83
<211> LENGTH: 49
<212> TYPE: DNA
<213> ORGANISM: Artificial Sequence
<220> FEATURE:
<223> OTHER INFORMATION: A synthetic primer

<400> SEQUENCE: 83
tgcgctagcc cgggatatcg ccaccatggt ggccatcctc tggcatgag         49

<210> SEQ ID NO 84
<211> LENGTH: 40
<212> TYPE: DNA
<213> ORGANISM: Artificial Sequence
<220> FEATURE:
<223> OTHER INFORMATION: A synthetic primer

<400> SEQUENCE: 84
gcatggatcc ttatcattcc agttttagaa gctccacatc                   40

<210> SEQ ID NO 85
<211> LENGTH: 49
<212> TYPE: DNA
<213> ORGANISM: Artificial Sequence
<220> FEATURE:
<223> OTHER INFORMATION: A synthetic primer

<400> SEQUENCE: 85
tgcgctagcc cgggatatcg ccaccatggt ggccatcctc tggcatgag         49

<210> SEQ ID NO 86
<211> LENGTH: 33
<212> TYPE: DNA
<213> ORGANISM: Artificial Sequence

```
<220> FEATURE:
<223> OTHER INFORMATION: A synthetic primer

<400> SEQUENCE: 86
gcattctaga ttaattccag ttttagaagc tcc                                33

<210> SEQ ID NO 87
<211> LENGTH: 34
<212> TYPE: DNA
<213> ORGANISM: Artificial Sequence
<220> FEATURE:
<223> OTHER INFORMATION: A synthetic primer

<400> SEQUENCE: 87
atgctacgta gctgaccagc tgactgagga gcag                               34

<210> SEQ ID NO 88
<211> LENGTH: 34
<212> TYPE: DNA
<213> ORGANISM: Artificial Sequence
<220> FEATURE:
<223> OTHER INFORMATION: A synthetic primer

<400> SEQUENCE: 88
atgcctcgag tcactttgca gtcatcatct gtac                               34

<210> SEQ ID NO 89
<211> LENGTH: 542
<212> TYPE: PRT
<213> ORGANISM: Artificial Sequence
<220> FEATURE:
<223> OTHER INFORMATION: A synthetic peptide

<400> SEQUENCE: 89
```

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

```
His Gln Asn Ile Cys Val Arg Leu Ile His Ala Leu Asp Pro Arg Val
            210                 215                 220

Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
                275                 280                 285

Ile Leu Phe Leu Ser Lys Ser Pro Leu Val Asp Lys Tyr Asp Leu Ser
            290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
                340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
            450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
                500                 505                 510

Val Arg Phe Val Asp Ser Ile Pro Arg Asn Val Thr Gly Lys Ile Thr
            515                 520                 525

Arg Lys Glu Leu Leu Lys Gln Leu Leu Glu Lys Ala Gly Gly
530                 535                 540

<210> SEQ ID NO 90
<211> LENGTH: 12
<212> TYPE: PRT
<213> ORGANISM: Click beetle

<400> SEQUENCE: 90

Tyr Val Asn Asn Val Glu Ala Thr Lys Glu Ala Ile
1               5                   10

<210> SEQ ID NO 91
<211> LENGTH: 12
<212> TYPE: PRT
<213> ORGANISM: Artificial Sequence
<220> FEATURE:
```

<223> OTHER INFORMATION: A synthetic peptide

<400> SEQUENCE: 91

Tyr Val Asn Asn Val Glu Ala Thr Lys Glu Ala Val
1               5                   10

<210> SEQ ID NO 92
<211> LENGTH: 18
<212> TYPE: PRT
<213> ORGANISM: Artificial Sequence
<220> FEATURE:
<223> OTHER INFORMATION: A synthetic peptide

<400> SEQUENCE: 92

Tyr Val Asn His His His His His His Asn Val Glu Ala Thr Lys Glu
1               5                   10                  15

Ala Val

<210> SEQ ID NO 93
<211> LENGTH: 20
<212> TYPE: PRT
<213> ORGANISM: Artificial Sequence
<220> FEATURE:
<223> OTHER INFORMATION: A synthetic peptide

<400> SEQUENCE: 93

Tyr Val Asn Asp Tyr Lys Asp Asp Asp Lys Asn Val Glu Ala Thr
1               5                   10                  15

Lys Glu Ala Val
            20

<210> SEQ ID NO 94
<211> LENGTH: 16
<212> TYPE: PRT
<213> ORGANISM: Artificial Sequence
<220> FEATURE:
<223> OTHER INFORMATION: A synthetic peptide

<400> SEQUENCE: 94

Tyr Val Asn Asp Glu Val Asp Asn Val Glu Ala Thr Lys Glu Ala Val
1               5                   10                  15

<210> SEQ ID NO 95
<211> LENGTH: 19
<212> TYPE: PRT
<213> ORGANISM: Artificial Sequence
<220> FEATURE:
<223> OTHER INFORMATION: A synthetic peptide

<400> SEQUENCE: 95

Tyr Val Asn Leu Arg Arg Ala Ser Leu Gly Asn Val Glu Ala Thr Lys
1               5                   10                  15

Glu Ala Val

<210> SEQ ID NO 96
<211> LENGTH: 8
<212> TYPE: PRT
<213> ORGANISM: Artificial Sequence
<220> FEATURE:
<223> OTHER INFORMATION: A synthetic peptide

<400> SEQUENCE: 96

Tyr Ala Ile Ala Ser Leu Asn Val
1               5

```
<210> SEQ ID NO 97
<211> LENGTH: 17
<212> TYPE: PRT
<213> ORGANISM: Artificial Sequence
<220> FEATURE:
<223> OTHER INFORMATION: A synthetic peptide

<400> SEQUENCE: 97

Tyr Ser Ile Thr Ser Ala Val Leu Gln Ser Gly Phe Arg Lys Met Ala
1               5                   10                  15

Val

<210> SEQ ID NO 98
<211> LENGTH: 12
<212> TYPE: PRT
<213> ORGANISM: Artificial Sequence
<220> FEATURE:
<223> OTHER INFORMATION: A synthetic peptide

<400> SEQUENCE: 98

Tyr Thr Ser Ala Val Leu Gln Ser Gly Phe Arg Val
1               5                   10

<210> SEQ ID NO 99
<211> LENGTH: 22
<212> TYPE: PRT
<213> ORGANISM: Artificial Sequence
<220> FEATURE:
<223> OTHER INFORMATION: A synthetic peptide

<400> SEQUENCE: 99

Tyr Val Asn Thr Ser Ala Val Leu Gln Ser Gly Phe Arg Asn Val Glu
1               5                   10                  15

Ala Thr Lys Glu Ala Val
            20

<210> SEQ ID NO 100
<211> LENGTH: 17
<212> TYPE: PRT
<213> ORGANISM: Artificial Sequence
<220> FEATURE:
<223> OTHER INFORMATION: A synthetic peptide

<400> SEQUENCE: 100

Tyr Gln Cys Ser Gly Val Thr Phe Gln Gly Lys Phe Lys Lys Ile Val
1               5                   10                  15

Val

<210> SEQ ID NO 101
<211> LENGTH: 12
<212> TYPE: PRT
<213> ORGANISM: Artificial Sequence
<220> FEATURE:
<223> OTHER INFORMATION: A synthetic peptide

<400> SEQUENCE: 101

Tyr Ser Gly Val Thr Phe Gln Gly Lys Phe Lys Val
1               5                   10

<210> SEQ ID NO 102
<211> LENGTH: 22
<212> TYPE: PRT
<213> ORGANISM: Artificial Sequence
<220> FEATURE:
<223> OTHER INFORMATION: A synthetic peptide

<400> SEQUENCE: 102
```

Tyr Val Asn Ser Gly Val Thr Phe Gln Gly Lys Phe Lys Asn Val Glu
1               5                   10                  15

Ala Thr Lys Glu Ala Val
            20

<210> SEQ ID NO 103
<211> LENGTH: 550
<212> TYPE: PRT
<213> ORGANISM: Artificial Sequence
<220> FEATURE:
<223> OTHER INFORMATION: A synthetic peptide

<400> SEQUENCE: 103

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

```
Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Pro Phe
            355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
            485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ile Ala Val
545                 550

<210> SEQ ID NO 104
<211> LENGTH: 5
<212> TYPE: PRT
<213> ORGANISM: Artificial Sequence
<220> FEATURE:
<223> OTHER INFORMATION: A synthetic affinity domain

<400> SEQUENCE: 104

Arg Tyr Ile Arg Ser
1               5

<210> SEQ ID NO 105
<211> LENGTH: 4
<212> TYPE: PRT
<213> ORGANISM: Artificial Sequence
<220> FEATURE:
<223> OTHER INFORMATION: A synthetic affinity domain

<400> SEQUENCE: 105

Phe His His Thr
1

<210> SEQ ID NO 106
<211> LENGTH: 4
<212> TYPE: PRT
<213> ORGANISM: Artificial Sequence
<220> FEATURE:
<223> OTHER INFORMATION: A synthetic peptide

<400> SEQUENCE: 106

Asp Glu Val Asp
1
```

<210> SEQ ID NO 107
<211> LENGTH: 7
<212> TYPE: PRT
<213> ORGANISM: Artificial Sequence
<220> FEATURE:
<223> OTHER INFORMATION: A synthetic peptide

<400> SEQUENCE: 107

Leu Arg Arg Ala Ser Leu Gly
1               5

<210> SEQ ID NO 108
<211> LENGTH: 6
<212> TYPE: PRT
<213> ORGANISM: Artificial Sequence
<220> FEATURE:
<223> OTHER INFORMATION: A synthetic peptide

<400> SEQUENCE: 108

Leu Val Pro Arg Glu Ser
1               5

<210> SEQ ID NO 109
<211> LENGTH: 36
<212> TYPE: DNA
<213> ORGANISM: Artificial Sequence
<220> FEATURE:
<223> OTHER INFORMATION: A synthetic primer

<400> SEQUENCE: 109
agctacatat ggatactgcg attttaagtg ttgttc                              36

<210> SEQ ID NO 110
<211> LENGTH: 40
<212> TYPE: DNA
<213> ORGANISM: Artificial Sequence
<220> FEATURE:
<223> OTHER INFORMATION: A synthetic primer

<400> SEQUENCE: 110
agctaggatc cttacggaat gatttgattg ccaaaaatag                          40

<210> SEQ ID NO 111
<211> LENGTH: 61
<212> TYPE: DNA
<213> ORGANISM: Artificial Sequence
<220> FEATURE:
<223> OTHER INFORMATION: A synthetic oligonucleotide

<400> SEQUENCE: 111
gaagggcgga aagatcgccg tggacgaagt tgacggtatg aagacgcca aaacataaa     60 g                                                                    61

<210> SEQ ID NO 112
<211> LENGTH: 11
<212> TYPE: PRT
<213> ORGANISM: Artificial Sequence
<220> FEATURE:
<223> OTHER INFORMATION: A synthetic peptide

<400> SEQUENCE: 112

Gly Gly Gly Asp Asp Asp Lys Gly Gly Gly
1               5                   10

<210> SEQ ID NO 113

```
<211> LENGTH: 17
<212> TYPE: PRT
<213> ORGANISM: Artificial Sequence
<220> FEATURE:
<223> OTHER INFORMATION: A synthetic peptide

<400> SEQUENCE: 113

Pro Gly Pro Gly Gly Gly Asp Asp Asp Asp Lys Gly Gly Gly Pro Gly
1               5                   10                  15
Pro

<210> SEQ ID NO 114
<211> LENGTH: 5
<212> TYPE: PRT
<213> ORGANISM: Artificial Sequence
<220> FEATURE:
<223> OTHER INFORMATION: A synthetic peptide

<400> SEQUENCE: 114

Asp Asp Asp Asp Lys
1               5

<210> SEQ ID NO 115
<211> LENGTH: 15
<212> TYPE: PRT
<213> ORGANISM: Artificial Sequence
<220> FEATURE:
<223> OTHER INFORMATION: A synthetic peptide

<400> SEQUENCE: 115

Gly Gly Ser Gly Gly Gly Gly Ser Gly Gly Gly Gly Ser Gly Gly
1               5                   10                  15

<210> SEQ ID NO 116
<211> LENGTH: 5
<212> TYPE: PRT
<213> ORGANISM: Artificial Sequence
<220> FEATURE:
<223> OTHER INFORMATION: A synthetic peptide

<400> SEQUENCE: 116

Asp Glu Val Asp Gly
1               5

<210> SEQ ID NO 117
<211> LENGTH: 5
<212> TYPE: PRT
<213> ORGANISM: Artificial Sequence
<220> FEATURE:
<223> OTHER INFORMATION: A synthetic peptide

<400> SEQUENCE: 117

Asp Asp Asp Asp Gly
1               5

<210> SEQ ID NO 118
<211> LENGTH: 6
<212> TYPE: PRT
<213> ORGANISM: Artificial Sequence
<220> FEATURE:
<223> OTHER INFORMATION: A synthetic peptide

<400> SEQUENCE: 118

Asn Leu Tyr Phe Gln Gly
1               5
```